United States Patent
Fogel et al.

(10) Patent No.: US 12,138,065 B2
(45) Date of Patent: Nov. 12, 2024

(54) DEMENTIA DETECTION

(71) Applicant: QUANTALX NEUROSCIENCE LTD, Beit Dagan (IL)

(72) Inventors: Hilla Fogel, Beit Dagan (IL); Iftach Dolev, Zur Moshe (IL)

(73) Assignee: QUANTALX NEUROSCIENCE LTD, Beit Dagan (IL)

( * ) Notice: Subject to any disclaimer, the term of this patent is extended or adjusted under 35 U.S.C. 154(b) by 0 days.

(21) Appl. No.: 18/080,033

(22) Filed: Dec. 13, 2022

(65) Prior Publication Data

US 2023/0113681 A1  Apr. 13, 2023

Related U.S. Application Data

(63) Continuation of application No. 17/274,196, filed as application No. PCT/IL2019/050991 on Sep. 5, 2019.
(Continued)

(51) Int. Cl.
*A61B 5/377* (2021.01)
*A61B 5/00* (2006.01)
(Continued)

(52) U.S. Cl.
CPC .............. *A61B 5/374* (2021.01); *A61B 5/383* (2021.01); *A61B 5/4088* (2013.01);
(Continued)

(58) Field of Classification Search
None
See application file for complete search history.

(56) References Cited

U.S. PATENT DOCUMENTS

| | | |
|---|---|---|
| 4,177,817 A | 12/1979 | Bevilacqua |
| 2002/0095080 A1 | 7/2002 | Cory et al. |

(Continued)

FOREIGN PATENT DOCUMENTS

| | | |
|---|---|---|
| CA | 3021208 A1 | 11/2017 |
| CN | 106139405 A | 11/2016 |

(Continued)

OTHER PUBLICATIONS

Cash, Robin FH, et al. "Characterization of glutamatergic and GABAA-mediated neurotransmission in motor and dorsolateral prefrontal cortex using paired-pulse TMS-EEG." Neuropsychopharmacology 42.2 (2017): 502-511. (Year: 2017).*
(Continued)

*Primary Examiner* — Jacqueline Cheng
*Assistant Examiner* — Jairo H Portillo
(74) *Attorney, Agent, or Firm* — Dorsey & Whitney LLP

(57) ABSTRACT

Apparatus and methods are described including driving a coil to apply a magnetic stimulation to a subject's brain, and receiving a magnetic-stimulation-evoked-potential signal from electrodes that are placed in contact with the subject's head. A slope of a late portion of a curve of the magnetic-stimulation-evoked-potential signal is measured. At least partially in response to detecting an indication that the slope of the late portion of the curve of the magnetic-stimulation-evoked-potential signal is below a given threshold, an output is generated that is indicative of the subject being at risk of dementia. Other applications are also described.

16 Claims, 34 Drawing Sheets

Related U.S. Application Data

(60) Provisional application No. 62/730,542, filed on Sep. 13, 2018.

(51) Int. Cl.

| | | |
|---|---|---|
| A61B 5/374 | (2021.01) | |
| A61B 5/383 | (2021.01) | |
| G06N 20/10 | (2019.01) | |
| G16H 20/10 | (2018.01) | |
| G16H 20/40 | (2018.01) | |
| G16H 30/40 | (2018.01) | |
| G16H 40/60 | (2018.01) | |
| G16H 50/20 | (2018.01) | |
| G16H 50/30 | (2018.01) | |

(52) U.S. Cl.
CPC ........... *A61B 5/7267* (2013.01); *G06N 20/10* (2019.01); *G16H 20/10* (2018.01); *G16H 20/40* (2018.01); *G16H 30/40* (2018.01); *G16H 40/60* (2018.01); *G16H 50/20* (2018.01); *G16H 50/30* (2018.01); *A61B 2560/02* (2013.01)

(56) References Cited

U.S. PATENT DOCUMENTS

| | | |
|---|---|---|
| 2007/0066914 A1 | 3/2007 | Le et al. |
| 2009/0105576 A1 | 4/2009 | Do et al. |
| 2009/0198305 A1 | 8/2009 | Rotstein et al. |
| 2010/0113959 A1 | 5/2010 | Pascual-Leone et al. |
| 2010/0324441 A1 | 12/2010 | Hargrove et al. |
| 2011/0118620 A1 | 5/2011 | Scheib |
| 2011/0118661 A1 | 5/2011 | Pless et al. |
| 2011/0119212 A1 | 5/2011 | De et al. |
| 2011/0224571 A1 | 9/2011 | Pascual-Leone et al. |
| 2011/0301683 A1 | 12/2011 | Axelgaard |
| 2012/0041296 A1 | 2/2012 | Garstka et al. |
| 2014/0058189 A1 | 2/2014 | Stubbeman |
| 2014/0235928 A1 | 8/2014 | Zangen et al. |
| 2015/0054838 A1 | 2/2015 | Koo |
| 2015/0065838 A1 | 3/2015 | Wingeier et al. |
| 2017/0291038 A1 | 10/2017 | Midorikawa et al. |
| 2017/0332934 A1 | 11/2017 | Dolev et al. |
| 2018/0236255 A1 | 8/2018 | Etkin |
| 2019/0201708 A1 | 7/2019 | Hathaway |
| 2020/0038676 A1 | 2/2020 | Rogachefsky et al. |
| 2020/0139113 A1 | 5/2020 | Shin et al. |
| 2020/0164218 A1 | 5/2020 | Glik et al. |

FOREIGN PATENT DOCUMENTS

| | | |
|---|---|---|
| DE | 4238744 A1 | 5/1994 |
| EP | 1008365 A1 | 6/2000 |
| JP | 2012125546 A | 7/2012 |
| WO | 2006122349 A1 | 11/2006 |
| WO | 2009044271 A2 | 4/2009 |
| WO | 2013175468 A2 | 11/2013 |
| WO | 2015034981 A1 | 3/2015 |
| WO | 2016016888 A1 | 2/2016 |
| WO | 2016093213 A1 | 6/2016 |
| WO | 2017189757 A1 | 11/2017 |
| WO | 2017196971 A1 | 11/2017 |
| WO | 2023177907 A1 | 9/2023 |
| WO | 2024127206 A1 | 6/2024 |
| WO | 2024134614 A1 | 6/2024 |

OTHER PUBLICATIONS

Dubovik, Sviatlana, et al. "Adaptive reorganization of cortical networks in Alzheimer's disease." Clinical neurophysiology 124.1 (2013): 35-43. (Year: 2013).*

Ferreri, Florinda, et al. "Sensorimotor cortex excitability and connectivity in Alzheimer's disease: A TMS-EEG co-registration study." Human brain mapping 37.6 (2016): 2083-2096. (Year: 201).*

Oral Proceedings for European Patent Application No. 16746238.1 mailed Feb. 8, 2023.

Baroncelli, et al., "Brain Plasticity and Disease: A Matter of Inhibition", Hindawi Publishing Corporation Neural Plasticity vol. 2011, Article ID 286073. doi:10.1155/2011/286073, May 4, 2011, 11 pages.

Bassett, et al., "Efficient Physical Embedding of Topologically Complex Information Processing Networks in Brains and Computer Circuits", PLoS Comput Biol vol. 6 Issue 4, e1000748. doi:10.1371/journal.pcbi.1000748, Apr. 22, 2010, pp. 1-14.

Bonato, et al., "Transcranial Magnetic Stimulation and Cortical Evoked Potentials: A TMS/EEG Co-Registration Study", Clinical Neurophysiology vol. 117, May 5, 2006, pp. 1699-1707.

Bowyer, "Coherence a Measure of the Brain Networks: Past and Present", Neuropsychiatric Electrophysiology vol. 2 No. 1. DOI 10.1186/s40810-015-0015-7, 2016, pp. 1-12.

Casarotto, et al., "EEG Responses to TMS Are Sensitive to Changes in the Perturbation Parameters and Repeatable over Time", PLoS ONE, vol. 5, Issue 4, e10281. doi:10.1371/journal.pone.0010281, Apr. 22, 2010, pp. 1-10.

Casula, et al., "Low-Frequency rTMS Inhibitory Effects in the Primary Motor Cortex: Insights from TMS-Evoked Potentials", NeuroImage. http://dx.doi.org/10.1016/j.neuroimage.2014.04.065, Sep. 2014, pp. 1-8.

Chen, "Depression of Motor Cortex Excitability by Low-Frequency Transcranial Magnetic Stimulation", Neurology 48. DOI 10.1212/WNL.48.5.1398, 1997, pp. 1398-1403.

Cherry, "Multimodality Imaging: Beyond PET/CT and SPECT/CT", Seminars in Nuclear Medicine vol. 39. doi:10.1053/j.semnuclmed.2009.03.001, Sep. 2009, pp. 348-353.

Corthout, et al., "Transcranial Magnetic Stimulation. Which Part of the Current Waveform Causes the Stimulation?", Exp Brain Res vol. 141. DOI 10.1007/s002210100860, Sep. 2001, pp. 128-132.

Dipasquale, et al., "Network Functional Connectivity and Whole-Brain Functional Connectomics to Investigate Cognitive Decline in Neurodegenerative Condition", Functional Neurology vol. 31 Issue 4, 2016, pp. 191-203.

Du, et al., "TMS Evoked N100 Reflects Local GABA and Glutamate Balance", Brain Stimul. vol. 11 No. 5. doi:10.1016/j.brs.2018.05.002, 2018, pp. 1071-1079.

Eguíluz, et al., "Scale-Free Brain Functional Networks", Physical Review Letters 94, 018102. DOI: 10.1103/PhysRevLett.94.018102, Jan. 14, 2005, 018102-1-018102-4.

Ferrarelli, et al., "Breakdown in Cortical Effective Connectivity During Midazolam-Induced Loss of Consciousness", PNAS vol. 107 No. 6. www.pnas.org/cgi/doi/10.1073/pnas.0913008107, Feb. 9, 2010, pp. 2681-2686.

Fitzgerald, et al., "A Comprehensive Review of the Effects of rTMS on Motor Cortical Excitability and Inhibition", Clinical Neurophysiology 117. doi:10.1016/j.clinph.2006.06.712, Aug. 4, 2006, pp. 2584-2596.

Frederiksen, "Corpus Callosum Atrophy in Patients with Mild Alzheimer's Disease", Neurodegenerative Diseases 2011; 8. DOI: 10.1159/000327753, Jun. 9, 2011, pp. 476-482.

Fregni, et al., "A Sham-Controlled Trial of a 5-Day Course of Repetitive Transcranial Magnetic Stimulation of the Unaffected Hemisphere in Stroke Patients", Stroke, Journal of the American Heart Association 2006; 37. doi: 10.1161/01.STR.0000231390.58967.6b, Jun. 29, 2006, pp. 2115-2122.

Garcia-Toro, et al., "High (20-Hz) and Low (1-Hz) Frequency Transcranial Magnetic Stimulation as Adjuvant Treatment in Medication-Resistant Depression", Psychiatry Research: Neuroimaging 146. doi:10.1016/j.pscychresns.2004.08.005, 2006, pp. 53-57.

Gore, et al., "Principles and Practice of Functional MRI of the Human Brain", The Journal of Clinical Investigation vol. 112 No. 1. doi:10.1172/JCI200319010, Jul. 2003, pp. 4-9.

Grant, et al., "Using Lithium in Children and Adolescents with Bipolar Disorder: Efficacy, Tolerability, and Practical Considerations", Pediatr Drugs 20. https://doi.org/10.1007/s40272-018-0289-x, Apr. 12, 2018, pp. 303-314.

(56) References Cited

OTHER PUBLICATIONS

Hallett, "Transcranial Magnetic Stimulation: A Primer", Neuron 55. DOI 10.1016/j.neuron.2007.06.026, Jul. 19, 2007, pp. 187-199.

Ilmoniemi, et al., "Methodology for Combined TMS and EEG", Brain Topogr 22. DOI 10.1007/s10548-009-0123-4, Dec. 10, 2009, pp. 233-248.

Ilmoniemi, et al., "Neuronal Responses to Magnetic Stimulation Reveal Cortical Reactivity and Connectivity", NeuroReport 8, Oct. 17, 1997, pp. 3537-3540.

Johnston, et al., "Plasticity in the Developing Brain: Implications for Rehabilitation", Developmental Disabilities Research Reviews 15, 2009, pp. 94-101.

Komssi, et al., "Ipsi- and Contralateral EEG Reactions to Transcranial Magnetic Stimulation", Clinical Neurophysiology 113, 2002, pp. 175-184.

Komssi, et al., "The Novelty Value of the Combined use of Electroencephalography and Transcranial Magnetic Stimulation for Neuroscience Research", Brain Research Reviews 52, Mar. 20, 2006, pp. 183-192.

Kugiumtzis, et al., "Direct Causal Networks for the Study of Transcranial Magnetic Stimulation Effects on Focal Epileptiform Discharges", International Journal of Neural Systems, vol. 25, No. 5 DOI: 10.1142/S0129065715500069, Mar. 12, 2015, 1550006-1-1550006-18.

Legon, et al., "Altered Prefrontal Excitation/Inhibition Balance and Prefrontal Output: Markers of Aging in Human Memory Networks", Cerebral Cortex. doi: 10.1093/cercor/bhv200, Sep. 22, 2015, pp. 1-12.

Lioumis, et al., "Reproducibility of TMS—Evoked EEG Responses", Human Brain Mapping 30. DOI: 10.1002/hbm.20608, Jun. 6, 2008, pp. 1387-1396.

Maeda, et al., "Modulation of Corticospinal Excitability by Repetitive Transcranial Magnetic Stimulation", Clinical Neurophysiology 111, 2000, pp. 800-805.

Mansur, et al., "A Sham Stimulationcontrolled Trial of rTMS of the Unaffected Hemisphere in Stroke Patients", Neurology 64, Jan. 27, 2005, pp. 1802-1804.

Mormino, et al., "Relationships between Beta-Amyloid and Functional Connectivity in Different Components of the Default Mode Network in Aging", Cerebral Cortex, vol. 21, Issue 10. doi:10.1093/cercor/bhr025, Oct. 2011, pp. 2399-2407.

Muellbacher, et al., "Effects of Low-Frequency Transcranial Magnetic Stimulation on Motor Excitability and Basic Motor Behavior", Clinical Neurophysiology 111, 2000, pp. 1002-1007.

Peinemann, et al., "Long-lasting Increase in Corticospinal Excitability After 1800 Pulses of Subthreshold 5 Hz Repetitive TMS to the Primary Motor Cortex", Clinical Neurophysiology 115. doi: 10.1016/j.clinph.2004.02.005, Mar. 14, 2004, pp. 1519-1526.

Premoli, et al., "TMS-EEG Signatures of GABAergic Neurotransmission in Human Cortex", The Journal of Neuroscience, vol. 34 No. 16. DOI:10.1523/JNEUROSCI.5089-13.2014, Apr. 16, 2014, pp. 5603-5612.

Radhu, et al., "Evidence for Inhibitory Deficits in the Prefrontal Cortex in Schizophrenia", Brain 138, Dec. 18, 2014, pp. 483-497.

Ragazzoni, et al., "Vegetative Versus Minimally Conscious States: A Study Using TMS-EEG, Sensory and Event-Related Potentials", Plos One vol. 8 Issue 2 e57069. doi:10.1371/journal.pone.0057069, Feb. 27, 2013, 11 pages.

Rogasch, et al., "Comparison of the Inhibitory Response to Tendon and Cutaneous Afferent Stimulation in the Human Lower Limb", J Neurophysiol 107. doi:10.1152/jn.00751.2011, Oct. 23, 2011, pp. 564-572.

Salanti, et al., "Impact of Placebo Arms on Outcomes in Impact of Placebo Arms on Outcomes in Antidepressant Trials: Systematic Review and Meta-Regression Analysis", Eur J Neurosci vol. 35 No. 6. doi: 10.1093/ije/dyy076, 2018, pp. 805-825.

Shafi, et al., "Exploration and Modulation of Brain Network Interactions with Exploration and Modulation of Brain Network Interactions with Neuroimaging", Eur J Neurosci. Vol. 35 No. 6. doi:10.1111/j.1460-9568.2012.08035.x, Mar. 2012, pp. 805-825.

Teipel, et al., "Measuring Cortical Connectivity in Alzheimer's Disease as a Brain Neural Network Pathology: Toward Clinical Applications", Journal of the International Neuropsychological Society 22. doi:10.1017/S1355617715000995, 2016, pp. 138-163.

Tremblay, et al., "Clinical Utility and Prospective of TMS-EEG", Clinical Neurophysiology vol. 130, Issue 5. https://doi.org/10.1016/j.clinph.2019.01.001, May 2019, pp. 802-844.

Veltman, et al., "Inflammatory Markers and Cortisol Parameters Across Depressive Subtypes in an Older Cohort", Journal of Affective Disorders, vol. 234. https://doi.org/10.1016/j.jad.2018.02.080, Jul. 2018, pp. 54-58.

Wray, et al., "NMDAR-Independent, cAMP-Dependent Antidepressant Actions of Ketamine", Molecular Psychiatry. https://doi.org/10.1038/s41380-018-0083-8, Jun. 18, 2018, 11 pages.

Advisory Action for U.S. Appl. No. 15/325,819 mailed Dec. 18, 2020.

Advisory Action for U.S. Appl. No. 15/325,819 mailed Feb. 16, 2021.

Communication Pursuant to Article 94(3) EPC for EP Patent Application No. 16746238.1 mailed May 27, 2021.

Communication Pursuant to Article 94(3) EPC for EP Patent Application No. 16746239.9 mailed May 28, 2021.

Examination Report European Patent Application No. 16746238.1 mailed Mar. 30, 2022.

Examination Report for European Patent Application No. 16746239.9 mailed Mar. 30, 2022.

Extended European Search Report for EP Patent Application No. 16746239.9 mailed Jan. 18, 2019.

Extended European Search Report for EP16746238.1 mailed Jan. 23, 2018.

Extended European Search Report for EP19860160.1 mailed Oct. 15, 2021.

Final Office Action for U.S. Appl. No. 15/325,819 mailed Oct. 8, 2020.

International Search Report and Written Opinion from International Application No. PCT/IL2016/050123 mailed May 22, 2016.

International Search Report and Written Opinion from International Application No. PCT/IL2016/050124 mailed May 22, 2016.

International Search Report and Written Opinion from International Application No. PCT/IL2019/050991 mailed Dec. 25, 2019.

International Search Report from International Application No. PCT/IL2015/050720 mailed Dec. 20, 2015.

Non-Final Office Action for U.S. Appl. No. 15/325,819 mailed Mar. 26, 2020.

Non-Final Office Action for U.S. Appl. No. 15/325,819 mailed May 26, 2021.

Notice of Allowance for U.S. Appl. No. 15/325,819 mailed Jan. 10, 2022.

Supplemental Notice of Allowability for U.S. Appl. No. 15/325,819 mailed Jan. 25, 2022.

U.S. Appl. No. 15/325,819, filed Jan. 12, 2017.

U.S. Appl. No. 17/274,196 to Fogel filed Mar. 8, 2021.

U.S. Appl. No. 62/730,542, filed Sep. 13, 2018.

Written Opinion from International Application No. PCT/IL2015/050720 mailed Dec. 15, 2015.

Alschuler, "Identifying Electrode Bridging From Electrical Distance Distributions: A Survey of Publicly-Available EEG Data Using a New Method", Clinical Neurophysiology, 2014, pp. 484-490.

Brunoni, et al., "Clinical research with transcranial direct current stimulation (tDCS): Challenges and future directions", Brain Stimulation, vol. 5, Issue 3, pp. 175-195, Jul. 2012.

Eigner, et al., "Repetitive Transcranial Magnetic Stimulation For the Treatment of Depress, Pain and Spasticity—Correlations with Neurochemical Parameters", Brain Stimulation, Jul. 2008, p. 247.

Hassan, et al., "Impaired long-term depression in schizophrenia: A cathodal tDCS pilot study", Brain Stimulation, vol. 5, Issue 4, pp. 475-483, Oct. 2012.

Miranda, et al., "What does the ratio of injected current to electrode area tell us about current density in the brain during tDCS?", Clinical Neurophysiology, vol. 120, Issue 6, pp. 1183-1187, Jun. 2009.

(56) References Cited

OTHER PUBLICATIONS

Nitsche, et al., "Excitability Changes Induced in the Human Motor Cortex by Weak Transcranial Direct Current Stimulation", Journal of Physiology, May 2000, pp. 633-639.

Pascual-Marqui, et al., "Low Resolution Brain Electromagnetic Tomography (LORETA) Functional Imaging in Acute, Neuropleptic-Naive, First Episode, Productive Schizophrenia", Psychiatry Research: Neuroimaging Section 90, Jan. 1999, pp. 169-179.

Paulus, "Transcranial Brain Stimulation: Potential and Limitations", e-Neuroforum, Jun. 2014, pp. 29-36.

Pilato, et al., "Synaptic Plasticity in Neurodegenerative Diseases Evaluated and Modulated by In Vivo Neurophysiological Techniques", Molecular Neurobiology, Jul. 2012, pp. 563-571.

Rossini, et al., "Non-Invasive Electrical and Magnetic Stimulation of the Brain, Spinal Cord, Roots and Peripheral Nerves: Basic Principles and Procedures for Routine Clinical and Research Application. An Updated Report from an I.F.C.N. Committee", Clinical Neurophysiology, Jun. 2015, pp. 1071-1107.

Schetatsky, et al., "Simultaneously EEG Monitoring During Transcranial Direct Current Stimulation", Journal of Visualized Experiments, Jun. 2013, pp. 1-11.

Extended European Search Report for EP Patent Application No. 16746239.9 mailed Jan. 19, 2018.

Summons to Oral Proceedings for European Application No. 16746239.9 mailed Dec. 22, 2022.

Non-Final Office Action for U.S. Appl. No. 17/274,196 mailed Dec. 21, 2023.

Office Action for Israel Application No. 281350 mailed Sep. 26, 2023.

Ferreri, et al., "Sensorimotor Cortex Excitability and Connectivity in Alzheimer's Disease: A TMS-EEG Co-Registration Study", Human Brain Mapping 37, 2016, 2083-2096.

Examination Report for European Application No. 19860160.1 mailed Feb. 26, 2024.

International Search Report and Written Opinion from International Application No. PCT/IB2023/062468 mailed Mar. 28, 2024.

International Search Report and Written Opinion from International Application No. PCT/IB2023/063172 mailed Jun. 4, 2024.

Lapitskaya, et al., "Corticospinal Excitability in Patients with Anoxic, Traumatic, and Non-Traumatic Diffuse Brain Injury", El Sevier—Brain Stimulation 6, 2013, pp. 130-137.

Röricht, et al., "Callosal and corticospinal tract function in patients with hydrocephalus: a morphometric and transcranial magnetic stimulation study", J Neurol, May 1998, pp. 280-288.

Sikka, et al., "Corticospinal excitability in idiopathic normal pressure hydrocephalus: a transcranial magnetic stimulation study", Fluids Barriers CNS, 17(1), Feb. 17, 2020, pp. 1-10.

\* cited by examiner

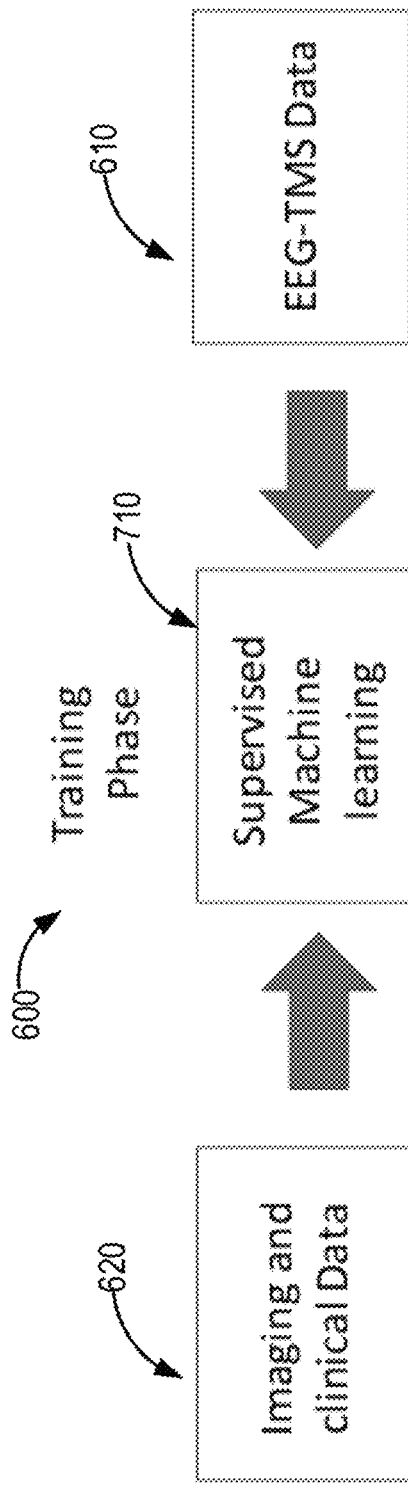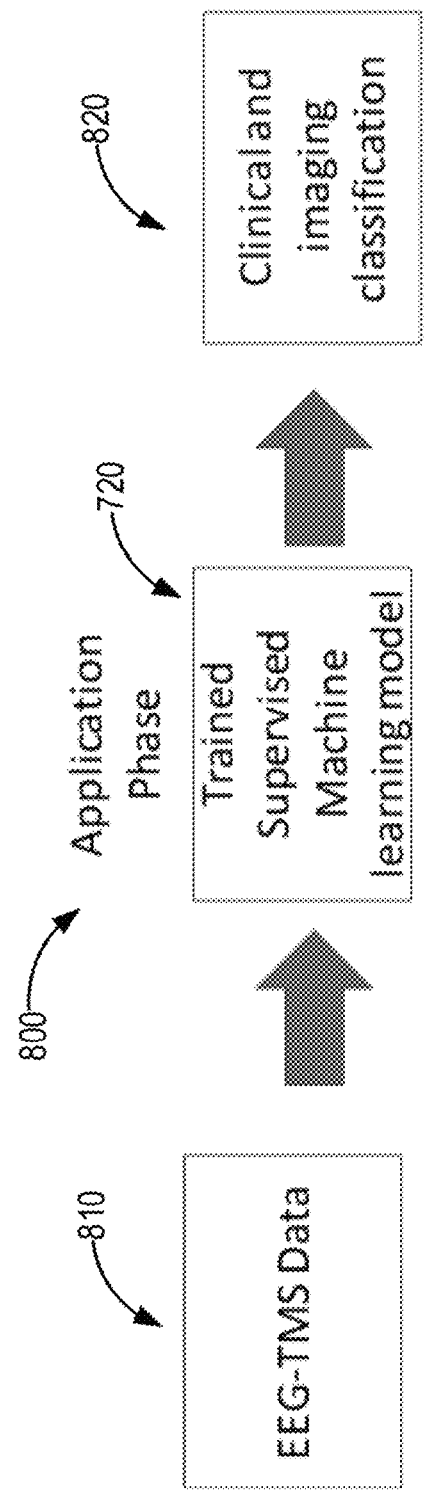

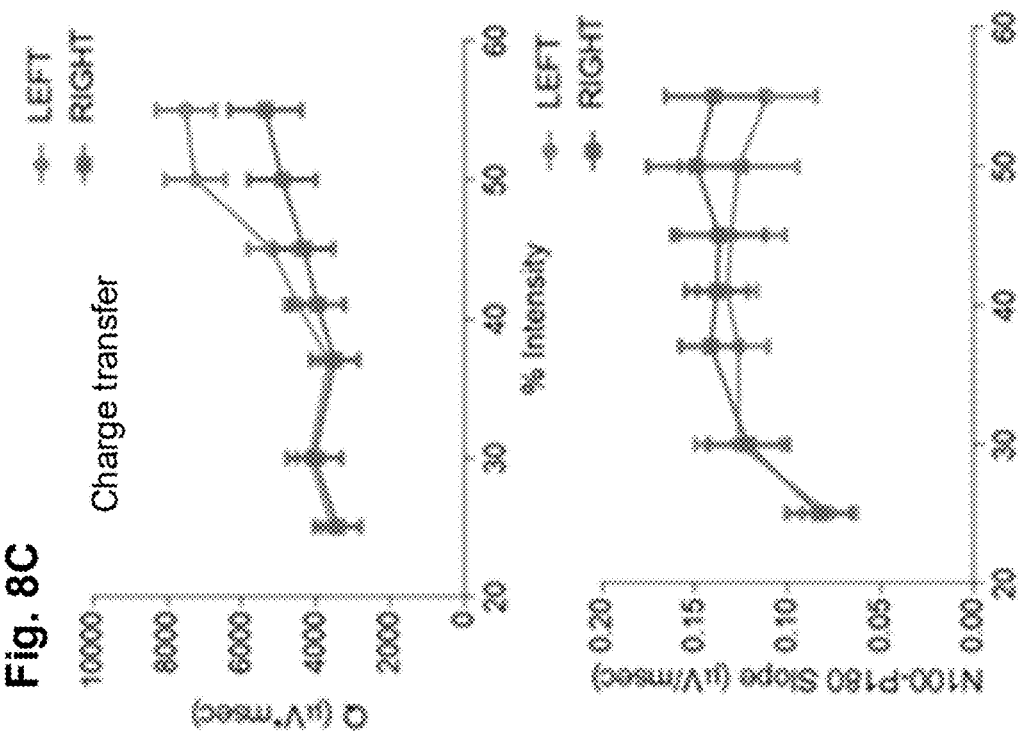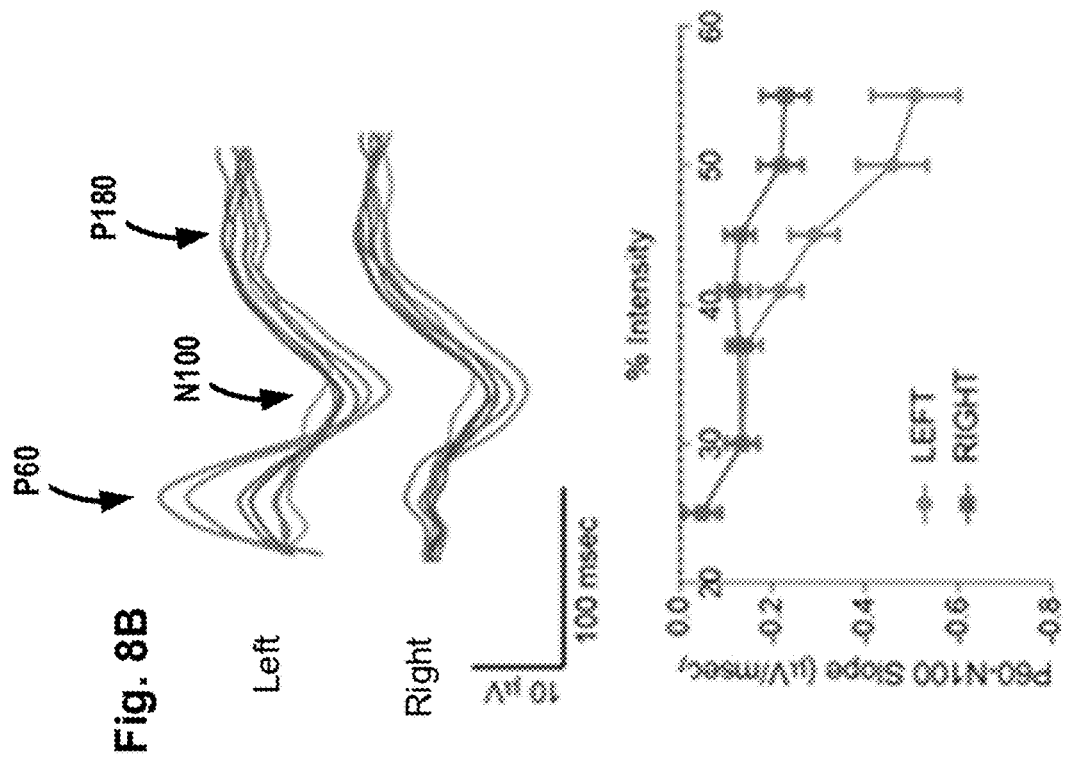

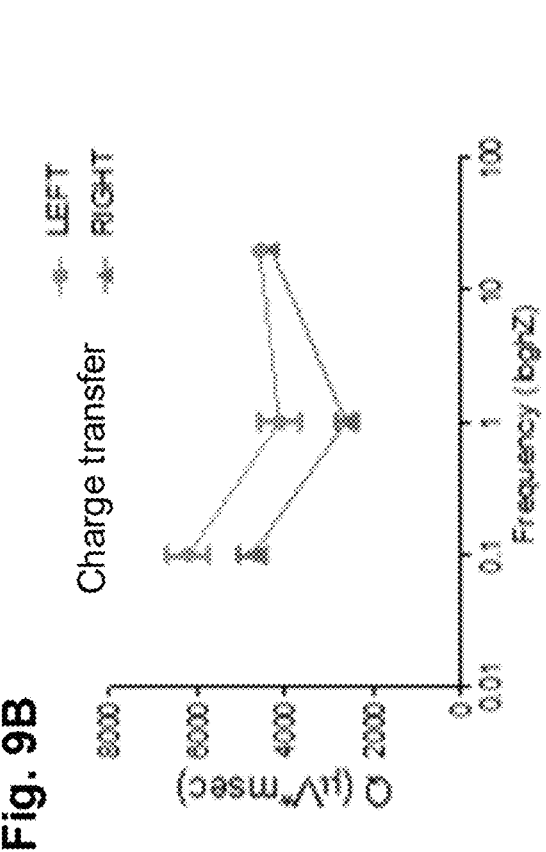
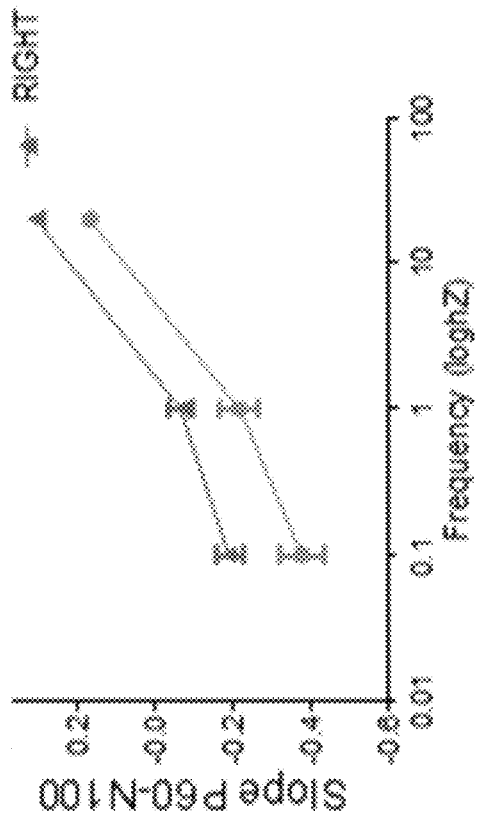
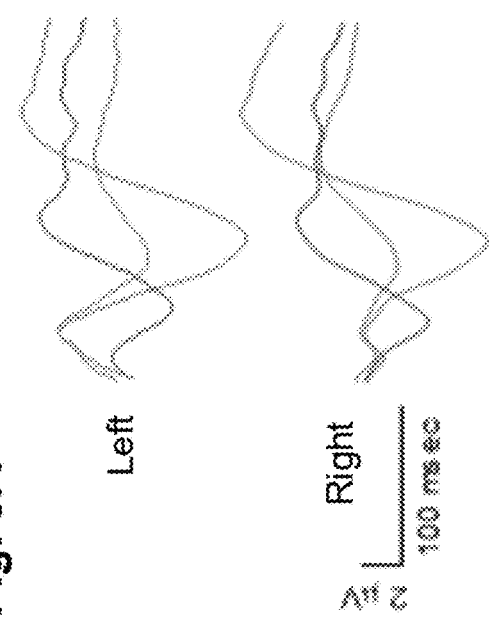
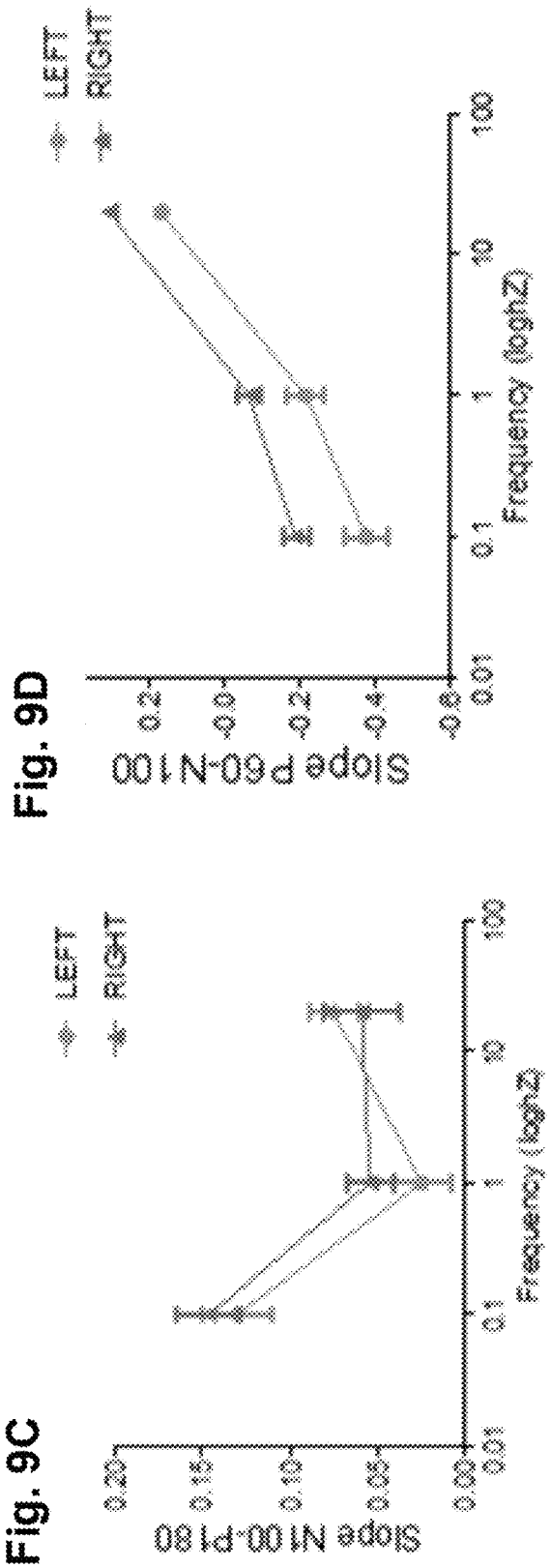

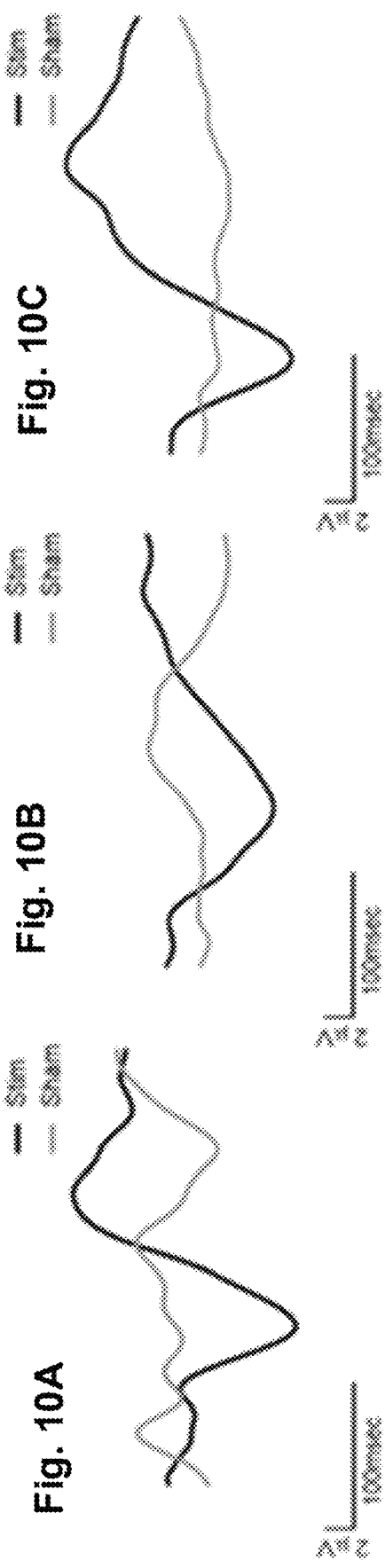
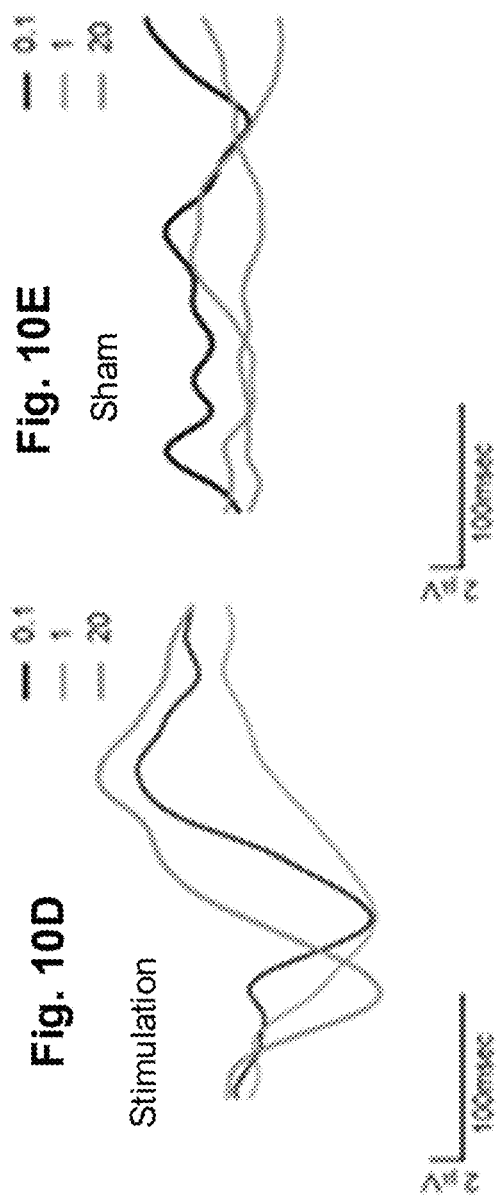

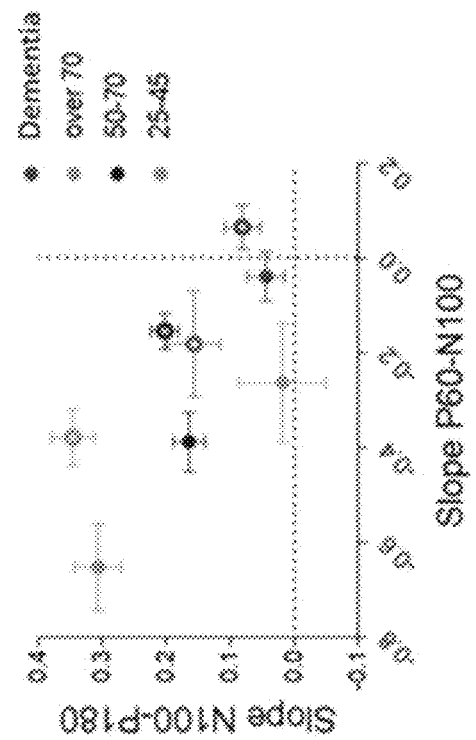
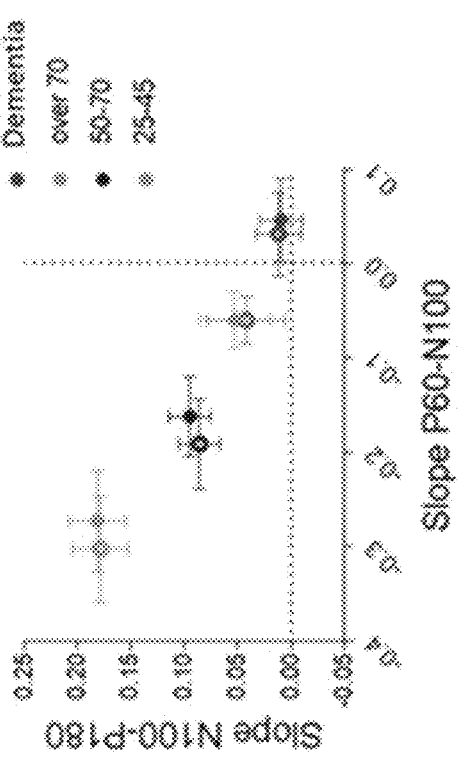
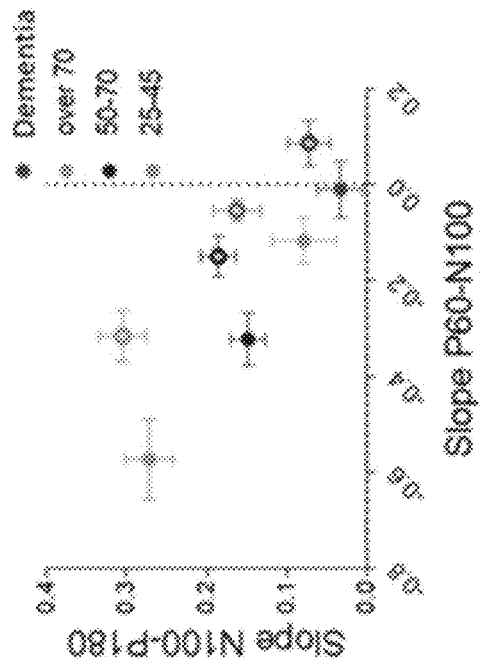
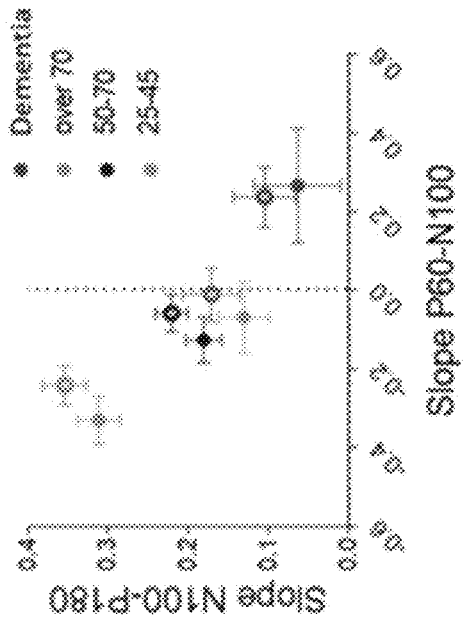

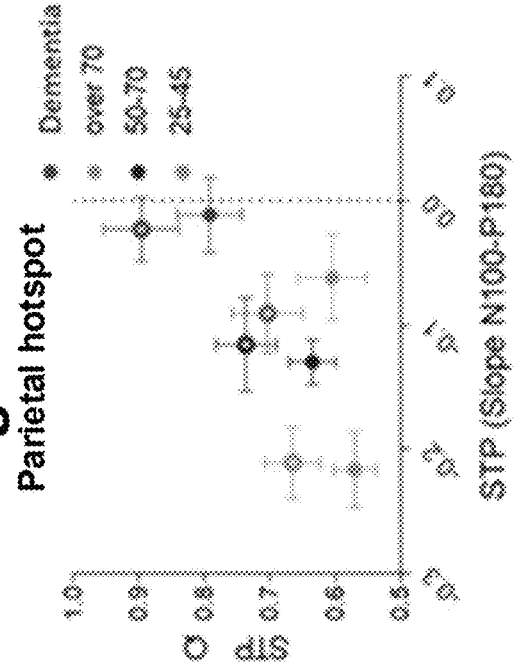
Fig. 15A Temporal hotspot
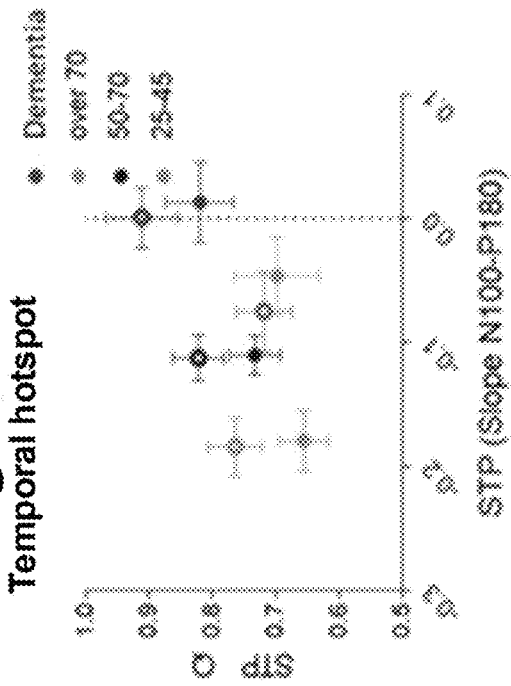
Fig. 15B Parietal hotspot
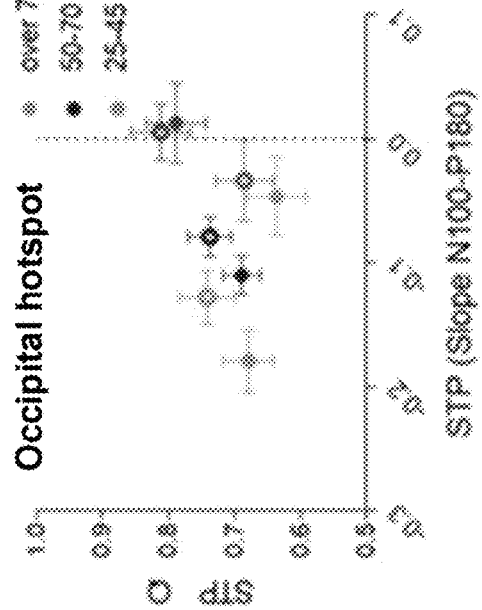
Fig. 15C Frontal hotspot
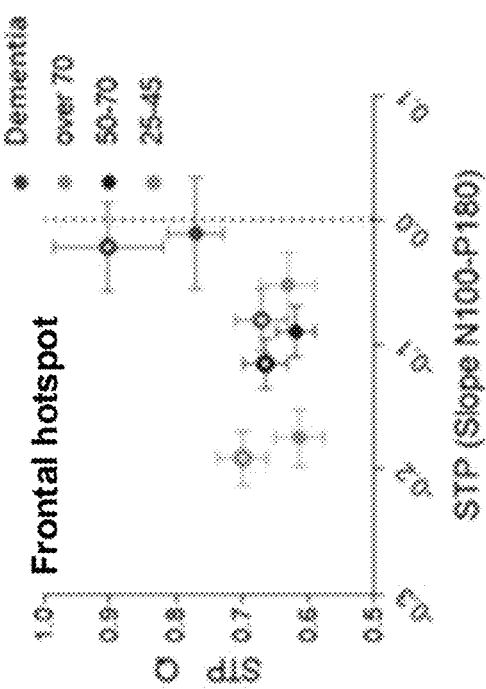
Fig. 15D Occipital hotspot

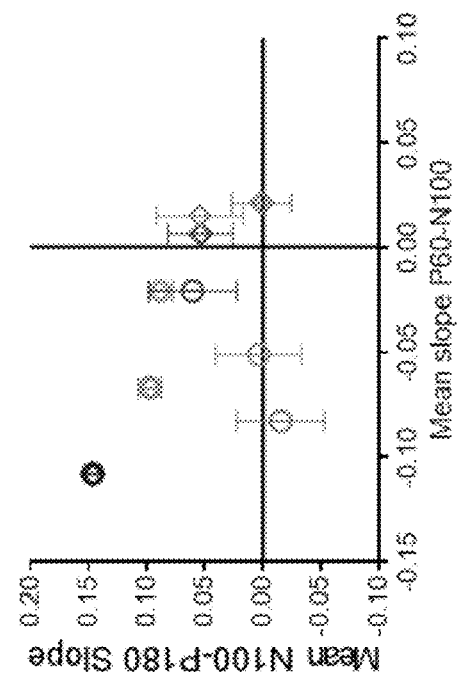

Fig. 16B

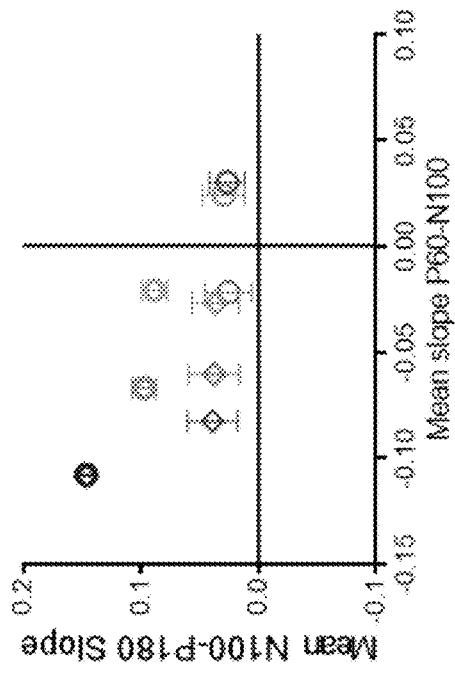

Fig. 16A

- ○ Healthy age 25-45 right hotspot
- ◇ Healthy age 25-45 left hotspot
- ○ Healthy age 50-70 right hotspot
- ◇ Healthy age 50-70 left hotspot
- ○ Healthy age over 70 right hotspot
- ◇ Healthy age over 70 left hotspot
- ○ CVA – Left corticospinal track injury right hotspot
- ◇ CVA – Left corticospinal track injury left hotspot
- ○ CVA – Left frontal lobe injury right hotspot
- ◇ CVA – Left frontal lobe injury left hotspot
- ○ CVA – Left temporal lobe injury right hotspot
- ◇ CVA – Left temporal lobe injury right hotspot

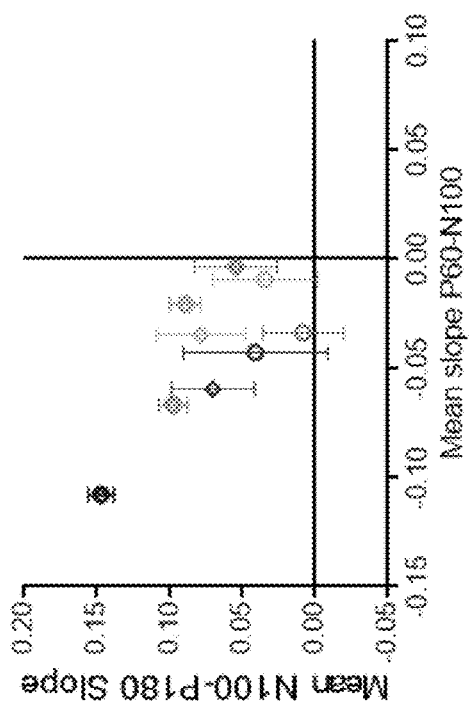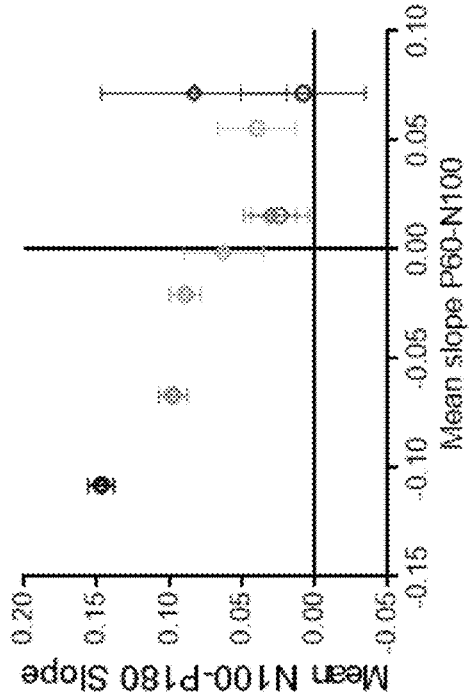

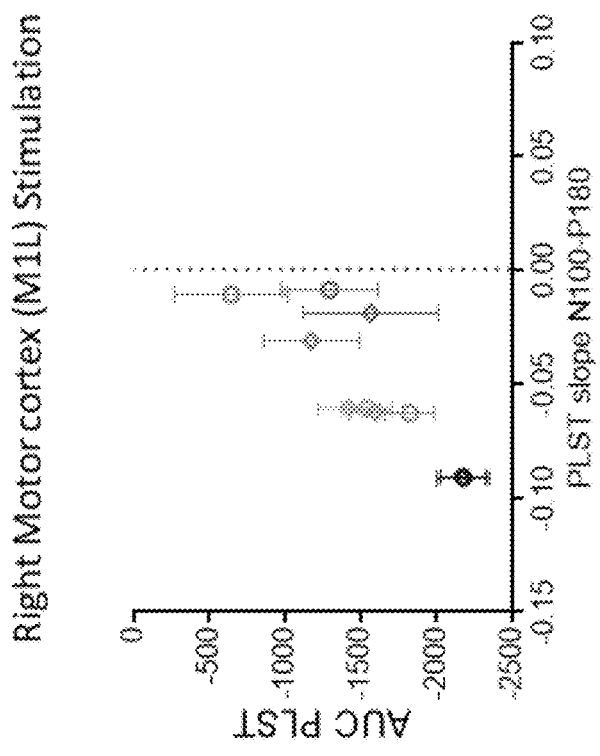
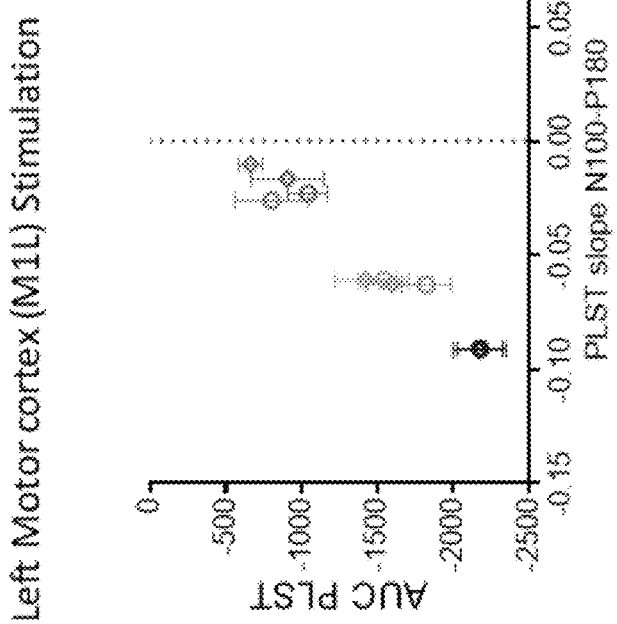
Fig. 21A
Fig. 21B

Fig. 23C        Fig. 23D
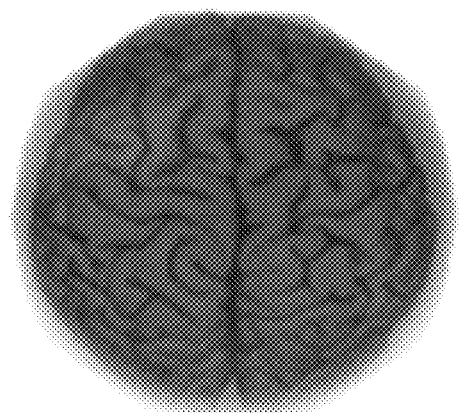 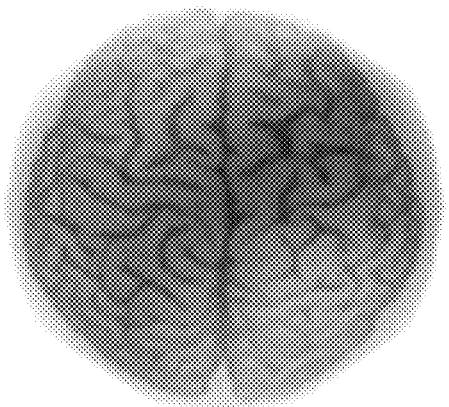 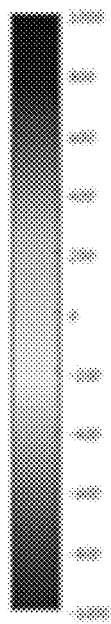
Age 38        Age 58
 
Age 75        Age 71, early dementia
Fig. 23E        Fig. 23F

Age 38
  Age 58
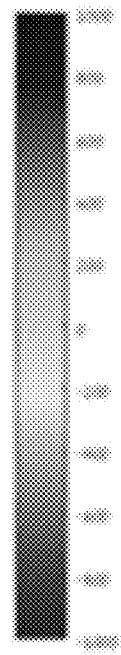
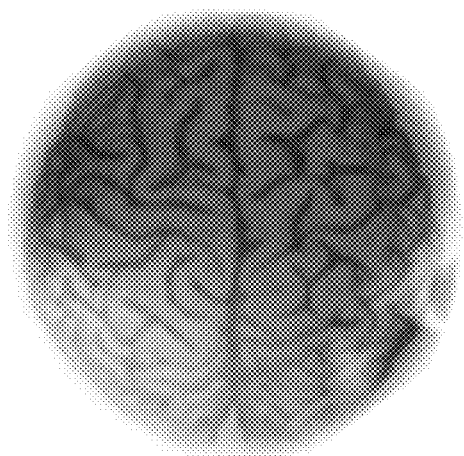 Age 75
Fig. 24E
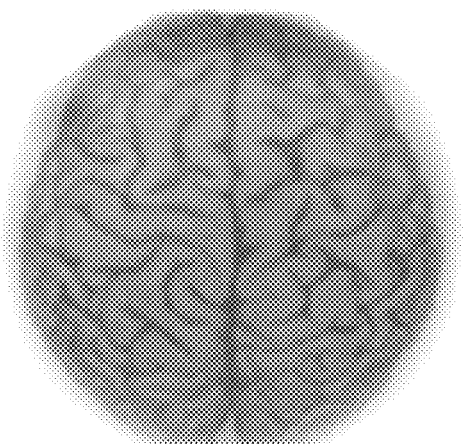 Age 71, early dementia
Fig. 24F

DEMENTIA DETECTION

CROSS REFERENCES TO RELATED APPLICATIONS

This application is a continuation of U.S. Ser. No. 17/274,196 to Fogel, filed Mar. 8, 2021 (published as US 2021/0353205), which is a US National Phase of International Application PCT/IL2019/050991 to Fogel (published as WO 2020/053849), filed Sep. 5, 2019, which claims priority from U.S. Provisional Patent Application No. 62/730,542 filed Sep. 13, 2018.

BACKGROUND OF THE INVENTION

The ability to deal with a challenge is limited by the tools one has to diagnose, evaluate and monitor the impact of the challenge. In the neuropsychiatric world, the ability to deal with the expanding risk of age associated brain disorders, such as Alzheimer's disease (AD), and other neurodegenerative-psychiatric disorders, an impact of which cannot be overstated, is limited by the lack of any tools which enable the evaluation and monitoring of brain health status. Current available technologies such as magnetic resonance imaging (MRI) or computed tomography (CT) scans provide high resolution images of the structural topology of the network but lack the ability to directly monitor brain functionality. Advanced technologies like, functional MRI (fMRI), or positron emission tomography (PET-CT) use indirect measurement as blood flow which correlates highly with regional changes in the level of activity but cannot be used for the direct evaluation of the logical topology of the network (Gore et al, *J Clin Invest.* 2003 July; Simon R et al, *Seminars in Nuclear Medicine*, September 2009). Moreover, these tools do not provide any valuable insights when evaluating brain health during normal aging or age-related pathological deterioration, such as mild cognitive impairment or early dementia, paradoxically, leaving the most prevalent brain related deterioration to be diagnosed and monitored by a subjective physician assessment, or cognitive evaluation at best.

The world of clinical neurology and psychiatry have some robust treatment tools such as brain directed pharmacological agents, for example Lithium (Grant B et al., *Paediatr Drugs.* 2018 August) and Ketamine (Wray N H et al, *Mol Psychiatry.* 2018 June) or electro convulsive treatment (ECT, Veltman E M et al, *J ECT* 2018 May). Still, most conditions do not have any specific proven treatment. Moreover, the actual effect of many brain directed drugs, (antidepressants for example), remains a matter of controversy (Salanti G et al, *Int J Epidemiol* 2018) due to the lack of any reliable, direct and objective tools for diagnosis, evaluation, and monitoring of brain functional status.

Electrophysiology is a well-established and important for evaluating brain network functionality. The use of electrophysiological measurements to characterize and monitor brain network activity has been used extensively over the last seven decades. From Hebb's pioneering work describing brain organization and synaptic plasticity (Hebb, D. O. (1949). *The Organization of Behavior.* New York: Wiley & Sons). Bliss and Lomo's work describing long term potentiation (LTP) (Lomo T, 2003 April *Philos Trans R Soc Lond B Biol Sci*), the breakthrough discoveries of Wiesel et al. on brain plasticity in the visual system (Wiesel, T. N. et al. (1963) *J. Neurophysiol*) and other discoveries lead the significant advancements in world of neuroscience research.

However, despite the understanding that electrophysiology is an important tool for understanding brain functionality in health and disease, there is still a need for a tool that enables an easy and safe electrophysiological measurement of brain network functionality, in the clinical practice.

Electrophysiological measurements can be generally divided into two groups of parameters: network integrity (meaning its connectivity and coherence), and network plasticity. The functional network connectivity depends on the synchronous activation of neurons and is used to determine the functional network integrity. Network coherence refers to the level of synchrony between two or more brain regions and is used to determine the strength of connectivity between specific brain regions (Bowyer et al. *Neuropsychiatric Electrophysiology,* 2016). Neuroplasticity, or brain plasticity, is an ability of the brain, to continuously adapt its functional and structural organization to changing requirements (Baroncelli et al. 2011, *Neuronla plasticity*). Neuronal plasticity allows the brain to reorganize neuronal networks in response to environmental stimulation, to remember information and to recover from brain and spinal cord injuries (Johnston, *Developmental Disabilities Research Reviews*, June 2009). Neuronal plasticity is essential to the establishment and maintenance of brain circuitry. Therefore, in order to enable a personalized clinical evaluation of brain health, there is a need for a reliable, reproducible and adaptable electrophysiological method to assess the functional network integrity and plasticity across each individual's lifespan.

Transcranial magnetic stimulation (TMS) is a non-invasive brain stimulation method that allows the study of human cortical function in vivo (Corthout et al. *Experimental Brain Research,* 2001 (Hallett, 2007; Rossini et al., 2015). Using TMS for examining human cortical functionality is enhanced by combining TMS with simultaneous registration of an electroencephalograph (EEG). EEG provides an opportunity to directly measure the cerebral response to TMS, measuring the cortical TMS evoked potential (TEP), and is used to assess cerebral reactivity across wide areas of neocortex (Casula et al. *NeuroImage*, September 2014). Studies integrating TMS with EEG (TMS-EEG) have shown that TMS produces waves of activity that reverberate throughout the cortex and that are reproducible and reliable (Casarotto et al., 2010; Lioumis et al., 2009), thus providing direct information about cortical excitability and connectivity with excellent time resolution (Thut et al. *Brain Topography,* 2010; Ilmoniemi, *Brain topography,* 2010). By evaluating the propagation of evoked activity in different behavioural states and in different tasks, TMS-EEG has been used to causally probe the dynamic effective connectivity of human brain networks (Kugiumtzis and Kimiskidis, 2015; Shafi et al., 2012).

An important feature of TEP topography is that even though only one cortical hemisphere is stimulated, bi-hemispheric EEG responses are evoked with different features. TMS-evoked activity propagates from the stimulation site ipsilaterally via association fibers, contralaterally via transcallosal fibers, and to subcortical structures via projection fibers. A single TMS pulse delivered over the primary motor cortex (M1) results in a sequence of positive and negative EEG peaks at specific latencies (i.e., N45, P60, N100, and P180; namely negative peaks at 45 mSec (N45) and 100 mSec (N100) after stimulation, positive peaks at 60 mSec (P60) and 180 mSec (P180) after stimulation).

This pattern of response indicates synaptic activity, specifically the Glutamate-excitatory and Gamma-aminobutyric acid (GABA)-inhibitory transmission balance (Du X,

*Brain Stimul.* 2018 September). It is believed that the N45 peak represents activity of α1-subunit-containing GABA-A receptors, whereas the N100 represents activity of GABA-B receptors (Premoli, *Journal of Neuroscience* 16 Apr. 2014). These TMS-evoked cortical potentials last for up to 300 mSec in both the vicinity of the stimulation, as well as in remote interconnected brain areas that reflect long term changes in cortical network excitation-inhibition balance, referred to as brain network plasticity (Ilmoniemi et al., 1997; Bonato et al., 2006; Lioumis et al., 2009; Premoli et al.).

Changes in this TMS evoked plasticity measurements provide important insights into cortical processing both in health (Massimini et al., 2005; Ferrarelli et al., 2010) and disease (Rosanova et al., *Neuronal network analysis: concepts and experimental approaches*. Totowa, NJ: Humana Press; 2012. p. 435e57; Ragazzoni et al., 2013) such as major depression and schizophrenia (Farzan et al.; Radhu et al, 2015). Thus, developing a bed side tool, based on the combinations of TMS and EEG technologies, has the potential to monitor pathological changes and therapy-induced modifications in cortical circuits (Premoli et al.).

SUMMARY OF THE INVENTION

According to some embodiments of the invention a new computer implemented method is provided configured for classifying a brain status of a subject, from a neural activity response of the subject to an induced TMS stimulation; the method comprising:

constructing a machine learning classifier (MLC) configured to classify a subject's brain status;

training the MLC using a training set, the training set comprising pairs of training output-classification vectors and their corresponding training input vectors, all extracted from a database of subjects with known brain status classifications, wherein:

each training output-classification vector is determined based on at least one of a database-subject's known: MRI readings, physician/s classification, cognitive testis evaluation, and any combination thereof;

each training input vector comprises features extracted from a database-subject's brain neural activity response to the induced TMS stimulation;

applying the trained MLC on an input vector comprising features extracted from a tested-subject's brain neural activity response to the induced TMS stimulation, to obtain an output classification vector for the tested-subject's brain status.

According to some embodiments, each output classification vector and accordingly each training output classification vector comprise features selected from:

physical status selected from: healthy/not healthy, the brain's evaluated age, neurological disorders, neurodegenerative disease, Alzheimer, Dementia, small vessels disease, Psychiatric disorders, depression, chronic pain, physical injury, pathophysiological abnormalities, structural damage of the grey matter, structural damage of the white matter, functional damage, internal bleeding, balance between excitation and inhibition in the regional cortical network, intra-cranial pressure, Cerebrovascular Accident (CVA), Basal ganglia injury, brain stem injury, corticospinal track injury, frontal lobe injury, temporal lobe injury, any combination thereof;

brain MRI-T1—gray matter and white matter volume and/or surface of cortical and subcortical areas;

diffused tensor MRI imaging (MRI-DWI)—white matter measures of fractional anisotropy (FA) and mean diffusivity (MD); and and any combination thereof.

According to some embodiments, the method further comprising a step of determining each training output-classification vector, based on at least one of a database-subject's known features.

According to some embodiments, the MLC comprises at least one module selected from:

a multi layered MLC;

a classification module, configured for separation of the extracted features into discrete classification groups, selected from:

support vector machine (SVM), decision trees, and

K-nearest neighbors;

registration module configured for continuous data prediction, selected from:

linear and/or non-linear regression, artificial neural network (NN), and adaptive fuzzy logic learning; and any combination thereof.

According to some embodiments, each of the input vectors and accordingly each of the training input vectors further comprises at least one feature selected from: age, gender, known medical status, drug treatment, blood pressure, and any combination thereof.

According to some embodiments, the TMS simulation frequency is selected from:

below 0.5 Hz, for a neural response, which does not depend upon stimulations history; and above 0.5 Hz, such that a neural response to pulses are affected by the previously provided pulses, thereby indicating short term plasticity.

According to some embodiments, the method further comprising steps of:

receiving, via an EEG device, a neural activity response of a subject's brain to the induced TMS stimulation to one or more predetermined brain regions of a subject; and extracting response features from the subject's neural activity response, as elements for an input vectors or a training input vector.

According to some embodiments, the step of extracting is at least based on positive and negative peaks at the neural activity response, and wherein the response features comprise at least one of the response's:

signal amplitudes;

amplitude latencies;

principle component analysis (PCA) and/or independent component analysis (ICA);

slopes between positive and negative peaks;

charge transfer;

lag of signal phase from healthy signal;

signal correlation to a healthy subject signal model;

ratio between segments in the signal of the same sensor, when TMS induced frequency is above 0.5 Hz;

coherence between the signal of different sensors;

brain connectivity; and any combination thereof.

According to some embodiments, the step of extracting comprises determining the positive and negative peaks, at time steps selected from a group consisting of: about 60 mSec, about 100 mSec, about 180 mSec and any combination thereof.

According to some embodiments, the step of extracting comprises determining the positive and negative peaks, at time steps selected from a group consisting of: about 45 mSec, about 120 mSec, about 180 mSec, 300 mSec and any combination thereof.

According to some embodiments, the extracted slopes are provided between determined positive and negative signal peaks, which are adjacent, thereby extracting peaks' relation. According to some embodiments, the extracted slopes are provided between determined peaks, which may not be adjacent.

According to some embodiments, the step of extracting features further comprises comparing the slope of the 60 mSec peak with the 100 mSec peak (60-100 slope), versus the slope of 100 mSec peak with 180 mSec peak (100-180 slope).

According to some embodiments, the step of extracting features further comprises comparing the slope of the 45 mSec peak with the 120 mSec peak (45-120 slope), versus the slope of 180 mSec peak with 300 mSec peak (180-300 slope).

According to some embodiments, the TMS is induced in several sequential stimulations, each at different intensity.

According to some embodiments, the TMS stimulated brain region is selected from a group consisting: frontal, parietal, temporal, occipital (right and left hemispheres) and any combination thereof.

According to some embodiments, a new apparatus is provided configured to evaluate brain state of a subject, the apparatus comprising:
- a directed inspective/diagnostic stimulation unit, configured to induce TMS diagnostic stimulation to a predetermined brain region of the subject;
- a brain activity EEG sensor, configured to measure a neural activity response to the diagnostic stimulation induced by the directed brain stimulation unit; and
- a processing circuitry and at least one memory unit, in wired or wireless communication with the brain activity sensor, the processing circuitry is configured to execute the method steps of any one of the preceding method steps for classifying a brain status of a subject, from a neural activity response of the subject to an induced TMS stimulation.

According to some embodiments, a new transient and/or non-transient computer readable medium (CRM) is provided that, when loaded into a memory of a computing device and executed by at least one processor of the computing device, configured to execute the steps of the computer implemented method according to any one of the preceding method steps for classifying a brain status of a subject, from a neural activity response of the subject to an induced TMS stimulation.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 5A and 5B schematically demonstrate MLC method phases: Training (FIG. 5A) and Application (FIG. 5B), according to some embodiments of the invention;

FIGS. 8A, 8B, 8C, 8D and 8E demonstrate intensity dependent TMS evoked response, in young healthy subjects (FIGS. 8B-8E), according to some embodiments of the invention;

FIGS. 9A, 9B, 9C and 9D demonstrate frequency dependent TMS evoked response in young healthy subjects, according to some embodiments of the invention;

FIGS. 10A, 10B, 10C, 10D and 10E demonstrate Sham Controlled TMS evoked stimulation in healthy subjects, according to some embodiments of the invention;

FIGS. 13A, 13B, 13C and 13D demonstrate representative N100-P180 slope vs. P60-N100 slope, according to some embodiments of the invention;

FIG. 14A for healthy subject and its average 14B; FIG. 14C for abnormal subject, according to some embodiments of the invention;

FIGS. 15A, 15B, 15C and 15D demonstrate representative short term plasticity of charge transfer as a function of short term plasticity of N100-P180 Slope, according to some embodiments of the invention;

FIGS. 16A and 16B demonstrate connectivity differences between healthy intact brain and specific brain injuries in left side, according to some embodiments of the invention;

FIGS. 18A and 18B demonstrate connectivity differences between healthy intact brain and specific brain injuries at the right side, according to some embodiments of the invention;

FIGS. 21A and 21B demonstrate short term plasticity differences between healthy intact brain and specific brain injuries in right side, according to some embodiments of the invention;

FIGS. 23A, 23B, 23C, 23D, 23E, and 23F demonstrate age dependent changes, and brain health change in brain network functionality and connectivity feature of early 60-100 slope and late 100-180 slope, according to some embodiments of the invention;

FIGS. 24A, 24B, 24C, 24D, 24E and 24F demonstrate age dependent changes and brain health change in network short term plasticity, according to some embodiments of the invention;

Figure 1:
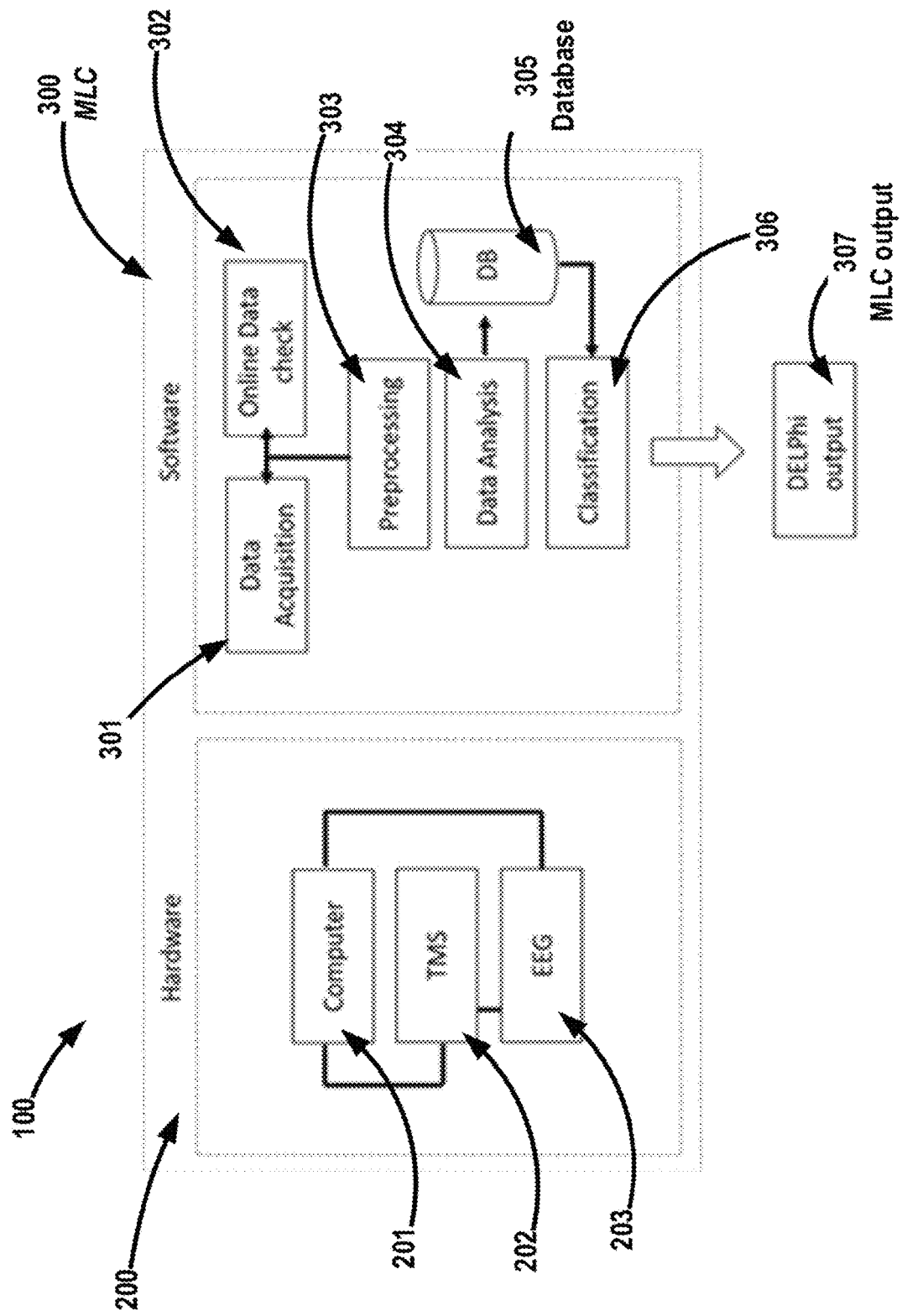
FIG. 1 schematically demonstrates modules of the DELPhi system, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The term "slope" as used herein, refers to the linear coefficient "a", where a x+b is the linear equation. According to some embodiments, the linear equation is determined by connecting two dots (two measurements). Alternatively, according to some embodiments, the linear equation is determined by linear regression of plurality of dots (plurality of measurements).

As used herein, in one embodiment the term "about" refers to ±10%. In another embodiment, the term "about" refers to ±9%. In another embodiment, the term "about" refers to ±8%. In another embodiment, the term "about" refers to ±7%. In another embodiment, the term "about" refers to ±6%. In another embodiment, the term "about" refers to ±5%. In another embodiment, the term "about" refers to ±4%. In another embodiment, the term "about" refers to ±3%. In another embodiment, the term "about" refers to ±2%. In another embodiment, the term "about" refers to ±1%.

The term "balance" as used herein, refers according to some embodiments, to the ability to maintain the ratio between excitation and inhibition (balance). Balance is an important physiological characteristic of brain plasticity.

The term "hotspot" as used herein, refers to a selected group of sensors that together represent a specific brain area.

The currently provided invention deals with a Direct Electro-Physiological Imaging (DELPhi) technology. DELPhi combines TMS-EEG and their robust scientific infrastructure into one complete automated acquisition and analysis system, making the critical neuro-physiological biomarkers clinically accessible.

The evidence described in the following supports DELPhi as the first clinically available tool for the successful evaluation, monitoring and diagnosis of age dependent brain conditions and disorders in a non-invasive, safe, easy to use and cost-effective manner.

Reference is now made to FIG. 1, which demonstrates the DELPHI system architecture 100. The system comprises customized integrated hardware device 200, comprising: TMS unit 202, an EEG unit 203 and a computer 201 comprising at least one processor.

The hardware unit 200 is configured for an automated data acquisition and for analysis via its software 300. According to some embodiments, the hardware section 200 of the DELPhi system for evaluating brain state of a subject comprises:

a directed inspective/diagnostic stimulation unit 202, configured to induce TMS diagnostic stimulation to a predetermined brain region of the subject;

a brain activity EEG sensor 203, configured to measure a neural activity response to the diagnostic stimulation induced by the directed brain stimulation unit; and a processing circuitry 201 in wired or wireless communication with the brain activity sensor, the processing circuitry is configured to evaluate a neuroplasticity and/or excitability of neural-structures in the predetermined brain region based on the neural activity response to the diagnostic stimulation;

as also demonstrated in WO2016/016888 (specifically in FIG. 1).

Figure 8A:
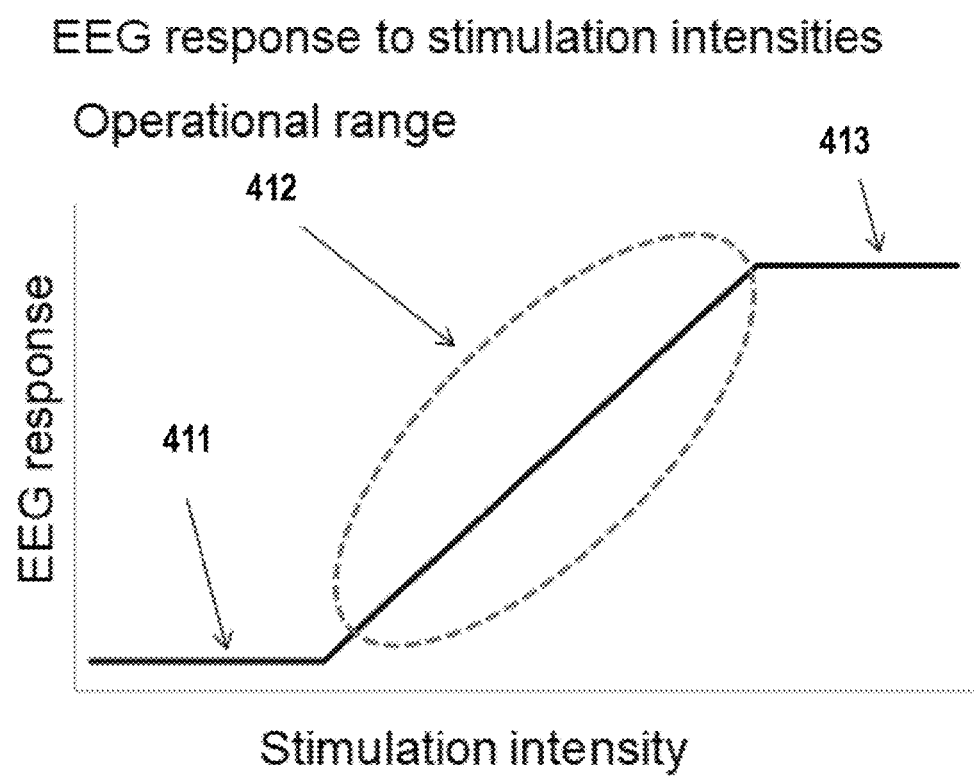

According to some embodiments, the inspective/diagnostic stimulation unit comprises a magnetically induced stimulation device and a controller thereof, configured to provide transcranial magnetic stimulation (TMS) pulses to the region of the brain of the subject. According to some embodiments, the intensity of the provided TMS pulses is within a range (FIG. 8A, 412), in which the subject's brain neural activity response is reactive to a change of the TMS pulse intensity. FIG. 8A schematically illustrates a stimulation intensity operational range 402, according to some embodiments. As illustrated, the EEG response to low stimulation intensities is relatively unchanged 411, until the stimulation intensity surpasses a certain value (lower threshold), then the EEG response reacts/increases as the stimulation intensity increases 412, until the stimulation intensity reaches another value (upper threshold) in which the EEG response no longer responds to increases in the stimulation intensity 413.

The currently provided evaluation of neuro-physiological properties, as network strength and plasticity, enables the characterization of age dependent brain functional changes. Moreover, the DELPhi acquisition and analysis system provide clinicians with a noninvasive, direct and objective tool for evaluating and monitoring brain health throughout aging, and enable an early detection of abnormal physiological changes leading to neurodegeneration, as for the case of mild cognitive impairment (MCI).

According to some embodiments, DELPHI's software architecture 300 comprises five layers or modules, as outlined in FIG. 1:

i. Data acquisition module 301: configured for automated data collection. A fixed stimulation protocol of TMS in varying intensities and frequencies, introduced to specific pre-determined locations on the skull, ensuring accuracy of the acquired TEP data;

ii. Online data check module 302: configured for automated and continuous evaluation of the collected data quality for optimal collection at minimum acquisition time. The online data check ensures a continuous online feedback of data quality;

iii. Data pre-processing module 303: configured for automated rapid cleaning of data following acquisition;

iv. Data analysis and features extraction module 304: configured to provide measured signal features, which are extracted and calculated for determining the relevant electrophysiological parameters of DELPHI physiological profiling; according to some embodiments, the analyzed data, the extracted features and optionally classification results are stored in a database 305 for further use; according to some embodiments, the database is configured to store and provide the analyzed data, the extracted features and the classification results data collected from the analysis of plurality of subjects "database subjects".

v. Classification of population subgroups module 306, configured to provide at least one of: numerical output data, color coded images and classification features of clinical conditions.

According to some embodiments, DELPHI's electrophysiological parameters constitute the subject network physiological profiling, which is displayed as numeric raw values. In order to enable disease classification, all clinical and DELPHI extracted features are uploaded into an anonymized cloud-based database 305 as part of the evaluation, this enables constant growth of DELPHI database and refinement of subgroups. Supervised machine learning algorithms enable incorporation of neurophysiological profile and clinical health status. The reliability of DELPHI as a state and disease classification tool increases with the growth in the quantity of collected neuro-physiological biomarkers data.

Figure 2:
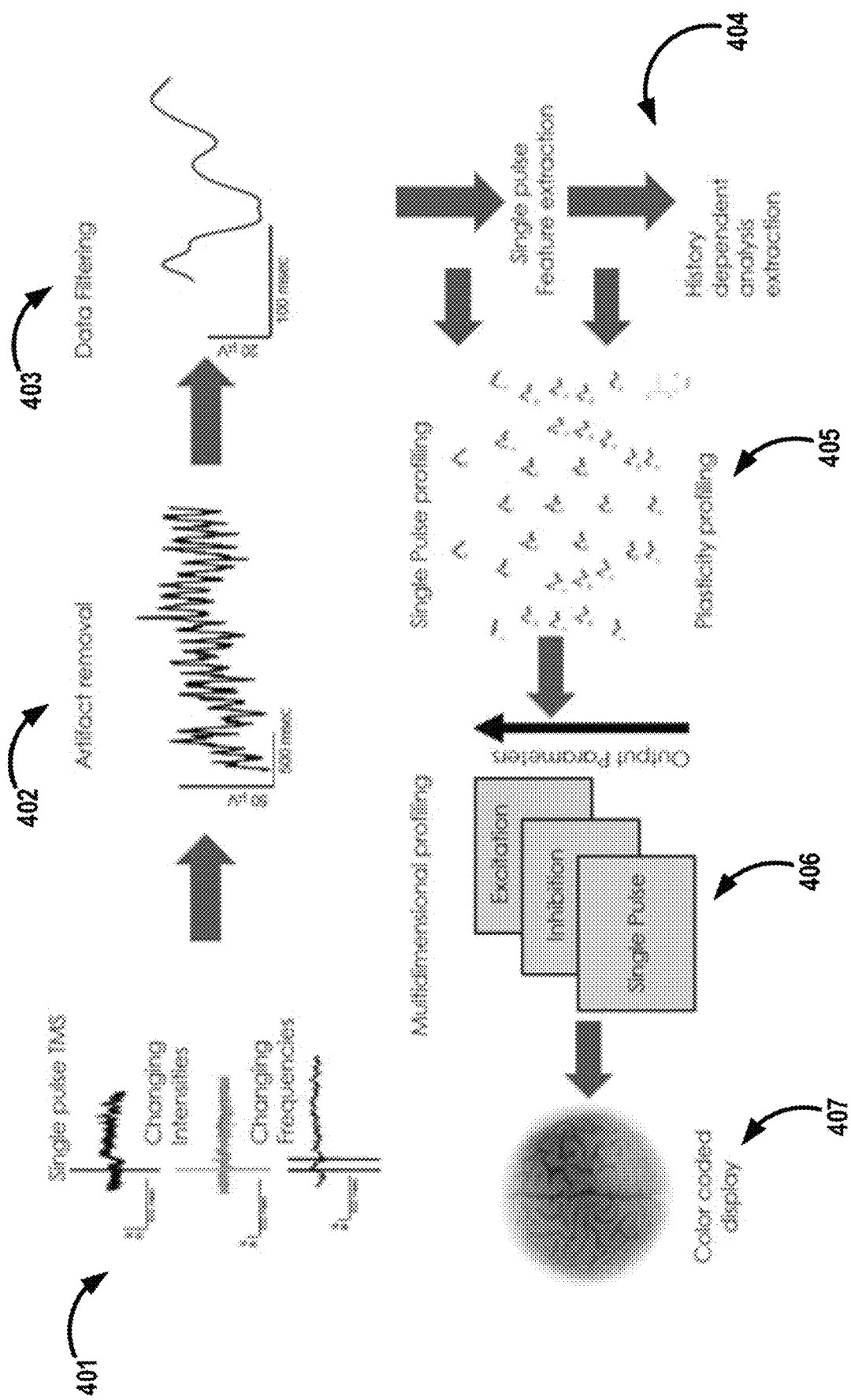
FIG. 2 schematically demonstrates a flow chart for extracting at least part of the input features to a machine learning classifier (MLC), according to some embodiments of the invention.

Reference is now made to FIG. 2, demonstrating a flow chart for extracting at least part of the input feature elements, according to some embodiments of the invention. The flow chart is demonstrating that data acquisition is performed automatically by introducing a sequence of stimuli in changing intensities and frequencies 401, followed by a bilayer data cleaning step of TMS artifact removal 402 and data filtering 403. In the following, average response features of charge transfer (area under the curve of sensor signal), slopes and latencies are extracted 404, providing the single pulse and plasticity profile of network functionality 405. These physiological parameters are unified into one multi-dimensional neuro-physiological DELPHI profile of brain network functionality 406. Cortical network values may be translated into pseudo-colored coded image describing brain network functionality 407.

Figure 3:
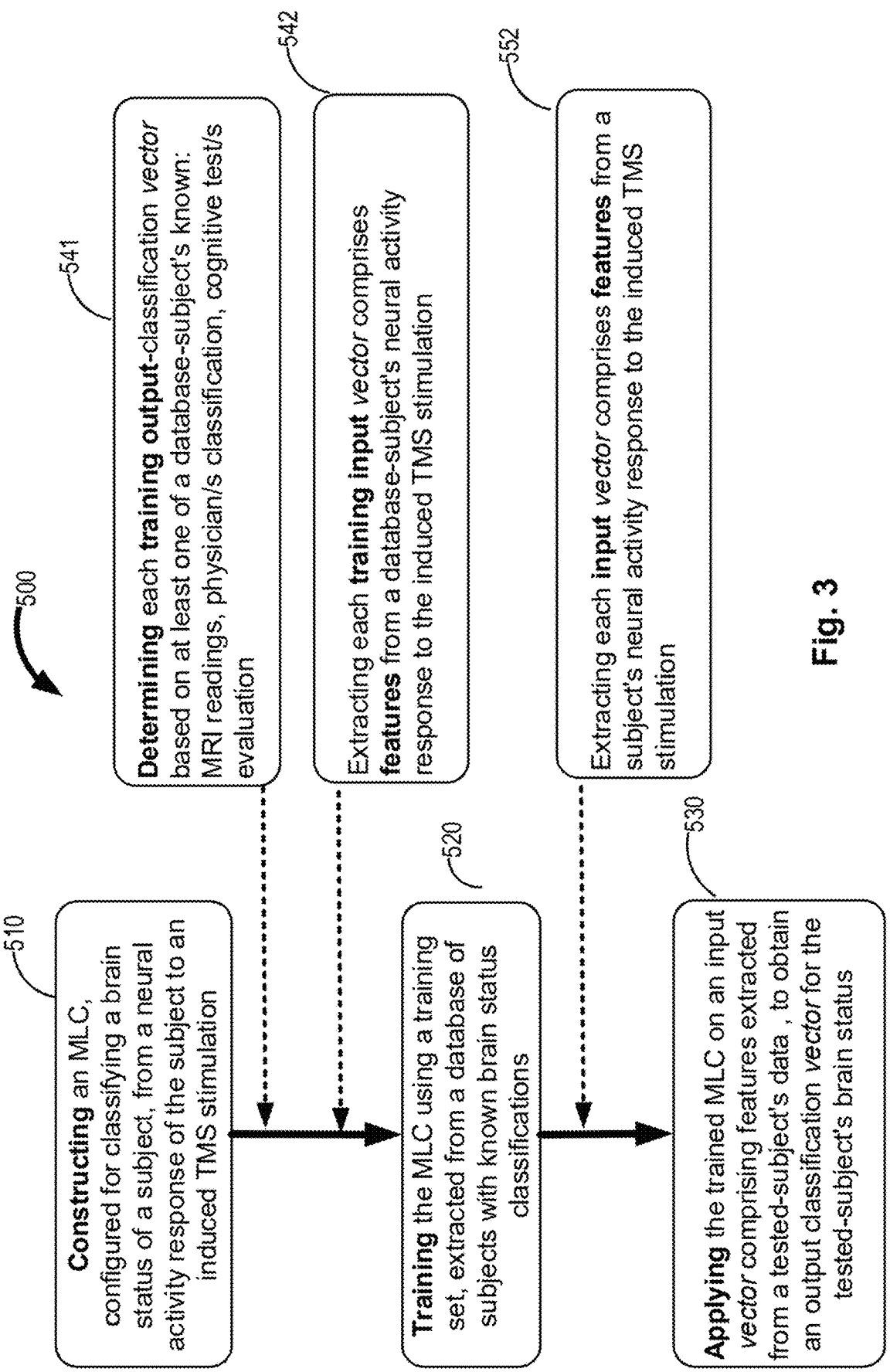
FIG. 3 schematically demonstrates a computer implemented method, configured for classifying a brain status of a subject, from a neural activity response of the subject to an induced TMS stimulation.

According to some embodiments, and as demonstrated in FIG. 3 a new computer implemented method 500 is provided, configured for classifying a brain status of a subject, from a neural activity response of the subject to an induced TMS stimulation. The method comprising:

constructing 510 at least one machine learning classifier (MLC) configured to classify a subject's brain status;

training 520 the MLC using a training set, the set comprising pairs of training output-classification vectors and their corresponding training input vectors, all extracted from a database of subjects with known brain status classifications, wherein:

each training output-classification vector is determined 541 based on at least one of a database-subject's known: MRI readings, physician/s classification, cognitive test/s evaluation, and any combination thereof;

each training input vector comprises features extracted from a database-subject's brain neural activity response to the induced TMS stimulation, the response is measured by an EEG device;

applying 530 the trained MLC on an input vector comprising features extracted from a tested-subject's neural activity response to the induced TMS stimulation, to obtain an output classification vector for the tested-subject's brain status.

According to come embodiments, the terms "brain State" and/or "brain status" refer to at least one selected from: brain's health, connectivity between the brain's areas, the brain's ability to process information, brain's plasticity, brain's activity and any combination thereof.

According to some embodiments, each output classification vector and accordingly each training output classification vector comprise features selected from:

brain MRI-T1: Gray matter and White matter volume and/or surface of cortical and subcortical areas; referred as vector "V1";

MRI-DWI (diffused tensor imaging): White matter measures of Fractional anisotropy (FA) and Mean diffusivity (MD); referred as vector "V2";

physical status selected from: healthy/not healthy, the brain's evaluated age, neurological disorders, neurodegenerative disease, Alzheimer, chronic pain, Dementia, small vessels disease, Psychiatric disorders, depression, physical injury, pathophysiological abnormalities, structural damage of the grey matter, structural damage of the white matter, functional damage, internal bleeding, balance between excitation and inhibition in the regional cortical network, intra-cranial pressure, cerebro-vascular accident (CVA), Basal ganglia injury, brain stem injury, corticospinal track injury, frontal lobe injury, temporal lobe injury, other brain area injuries, diabetes, hypertension and any combination thereof; referred as vector "V3";

and any combination thereof.

According to some embodiments, the method 500 further comprising a step of determining each training output-classification vector, based on at least one of a database-subject's known: MRI readings, physician/s classification, cognitive test/s evaluation.

According to some embodiments, the MLC comprises at least one module selected from:

a multi layered MLC;

a classification module (for categorization), configured for separation of the extracted features into discrete classification groups performed by, at least one selected from:

support vector machine (SVM), decision trees, and

Figure 4:
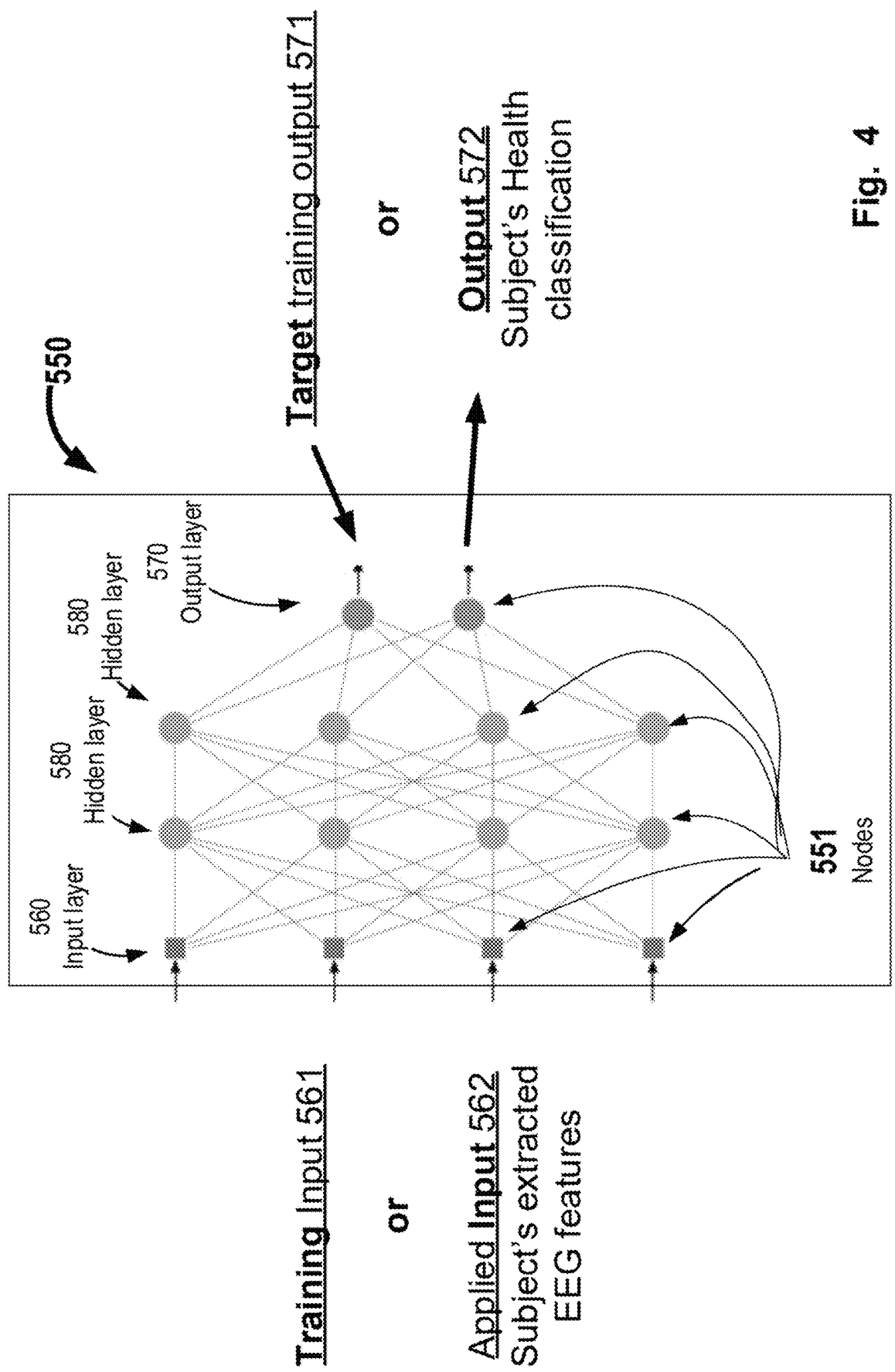
FIG. 4 schematically demonstrates an example for an MLC comprising a multi layered neural network (NN), according to some embodiments of the invention.

K-nearest neighbors;

a registration module, configured for continuous data prediction, selected from:

linear and/or non-linear regression, artificial neural network (NN), as demonstrated in FIG. 4, and adaptive fuzzy logic learning;

any combination thereof.

According to some embodiments, and as demonstrated in FIG. 4 the MLC 550 comprises a multi layered neural network (NN) comprising plurality of nodes 551, configured as: an input layer 560 for the training input 561 or applied input 562 extracted from subject's EEG features; an output layer for the target training output 571 or output 572 for the subject's health classification; and hidden layers 580.

According to some embodiments, each of the input vectors and accordingly each of the training input vectors further comprises at least one feature selected from: age, gender, known medical status, drug treatment, blood pressure, and any combination thereof.

According to some embodiments, the TMS simulation frequency is selected from:

below 0.5 Hz; noted herein as "single pulse" for a neural response, which does not depend upon stimulations history; and above 0.5 Hz; noted herein as "a paired pulse", where the neural response to pulses are affected by the previously provided pulses, which indicates short term plasticity.

According to some embodiments, the TMS simulation frequency is selected between 0.1 Hz and 20 Hz.

According to some embodiments, the method 500 further comprising steps of:

receiving, via an EEG device, a neural activity response of a subject's brain to the induced TMS stimulation to one or more predetermined brain regions of a subject; according to some embodiment, eight location are being sensed, four at each side (right/left), and extracting response features 542,552 from the subject's neural activity response, as elements for an input vectors or a training input vector.

According to some embodiments, the step of extracting 542,552 is at least based on positive and negative peaks at the neural activity response, measured, for example, in the range of 25-300 milliseconds after the TMS stimulation is provided; and wherein the response features comprise at least one of the response's:

signal amplitudes;

amplitude latencies;

signal components analysis, such as principle component analysis (PCA), and independent component analysis (ICA);

slopes between positive and negative peaks;

charge transfer (area under the curve of sensor signal);

lag of signal phase from healthy signal;

signal correlation to a healthy subject signal model;

ratio between segments in the signal of the same sensor, when TMS induced frequency is above 0.5 Hz ("paired");

coherence between the signal of different sensors;

brain connectivity; and any combination thereof.

According to some embodiments, connectivity and plasticity are determined in different ways. For example, measuring short term plasticity by comparing one pulse response to another for example. According to some embodiments, connectivity is determined by examining response latencies and coherence between electrodes.

According to some embodiments, the step of extracting comprises determining the positive- and negative-peaks, at time steps selected from a group consisting of: about 60 milli-seconds (mSec), about 100 mSec, about 180 mSec, and any combination thereof. According to some embodiments, the determining of the positive- and the negative-peaks, can be selected at other predetermined time steps.

According to some embodiments, the extracted slopes are provided between determined positive and negative signal peaks, which are adjacent, thereby extracting peaks' relation. According to some embodiments, the extracted slopes are provided between the determined peaks, which may not be adjacent.

According to some embodiments, the step of extracting features further comprises comparing the slope of the 60 mSec peak with the 100 mSec peak (60-100 slope), versus the slope of 100 mSec peak with 180 mSec peak (100-180 slope).

According to some embodiments, the step of extracting features further comprises comparing the 60-100 slope with the 100-180 slop.

According to some embodiments, the TMS is induced in several sequential stimulations, each at different intensity.

According to some embodiments, the stimulated brain region is selected from a group consisting: frontal, parietal, temporal, occipital (right and left hemispheres) and any combination thereof.

According to some embodiments, the terms "early slope" and/or "early phase deflection (EPD)" refer to a slope of early response component, for example a component measured at 60-100 mSec after the TMS stimulation. According to some embodiments, the terms "late slope" and/or "late phase deflection (LPD)" refer to a slope of late response component, for example a component measured at 100-180 mSec after the TMS stimulation. According to some embodiments, the terms "correlation to ideal signal" and/or "wave form adherence (WFA)" refer to correlation of a signal from a sensor to healthy ideal form. According to some embodiments, the term "short term inhibitory plasticity" refers to the relation between a neural response to a first TMS pulse and a neural response to a second TMS pulse, during inhibitory TMS stimulation protocol, meaning TMS stimulation frequency ranging between 1 Hz to 5 Hz. According to some embodiments, the term "short term excitatory plasticity" refers to the relation between a neural response to a first TMS pulse and a neural response to a second TMS pulse, during excitatory TMS stimulation protocol, meaning TMS stimulation frequency provided above 10 Hz. According to some embodiments, the term "charge transfer" refers to the area under the curve of sensor signal. According to some embodiments, the term "signal lag" refers to the lag of signal phase from healthy ideal signal.

According to some embodiments, the input vectors and accordingly each of the training input vectors comprise at least one feature extracted from the neural response to the TMS stimulation, the feature is selected from:

early slope/late slope*correlation to ideal signal; for a TMS frequency below 0.5 Hz (single pulse); referred as "DELPhi_feature1";

coherence between individual sensors; for a TMS frequency below 0.5 Hz (single pulse); referred as "DELPhi_feature2";

short term inhibitory plasticity/short term excitatory plasticity; for a TMS frequency above 0.5 Hz (paired pulse); referred as "DELPhi_feature3";

charge transfer*signal lag (from ideal); for a TMS frequency below 0.5 Hz (single pulse); referred as "DELPhi_feature4"; and any combination thereof.

Figure 6A:
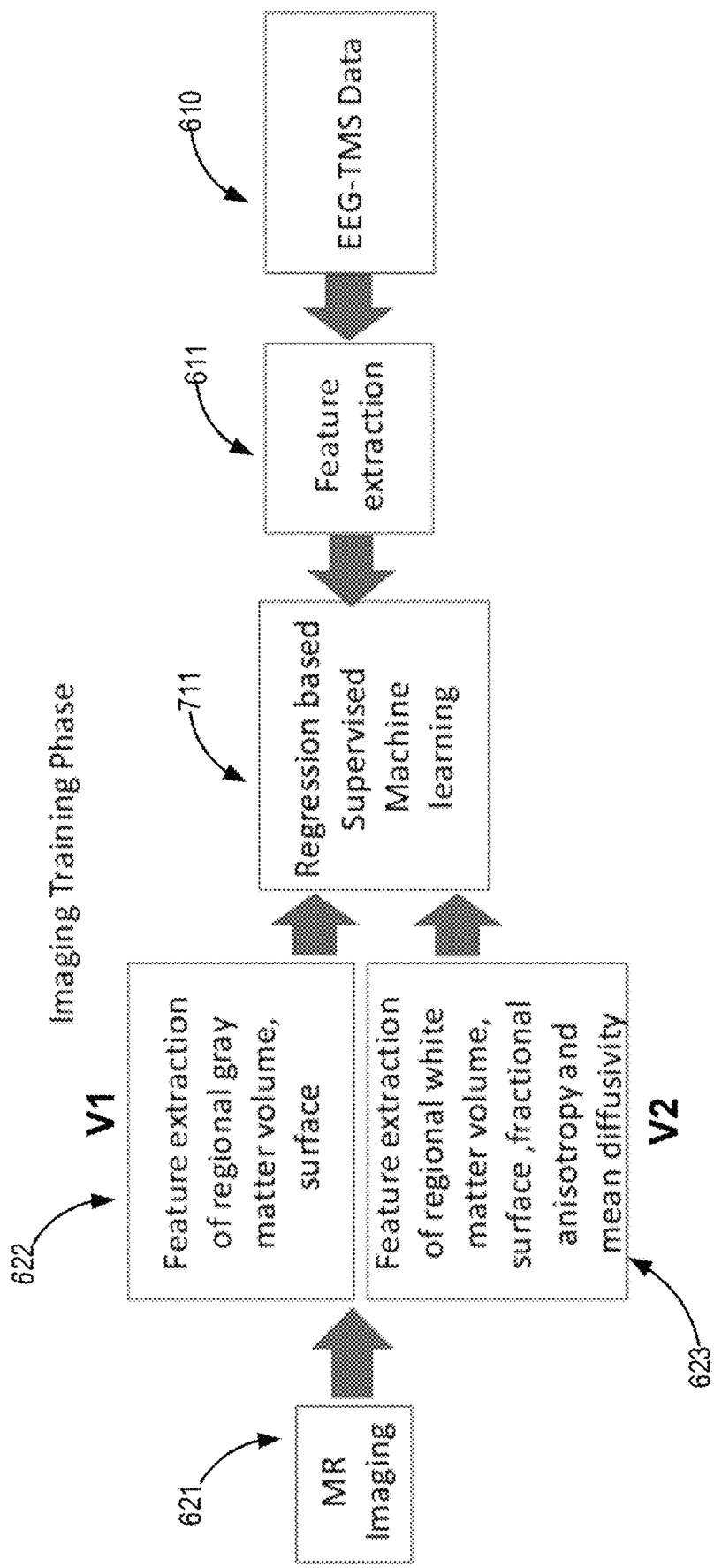
FIGS. 6A, 6B and 6C schematically demonstrate examples for different training phases, according to some embodiments of the invention.
Figure 6B:
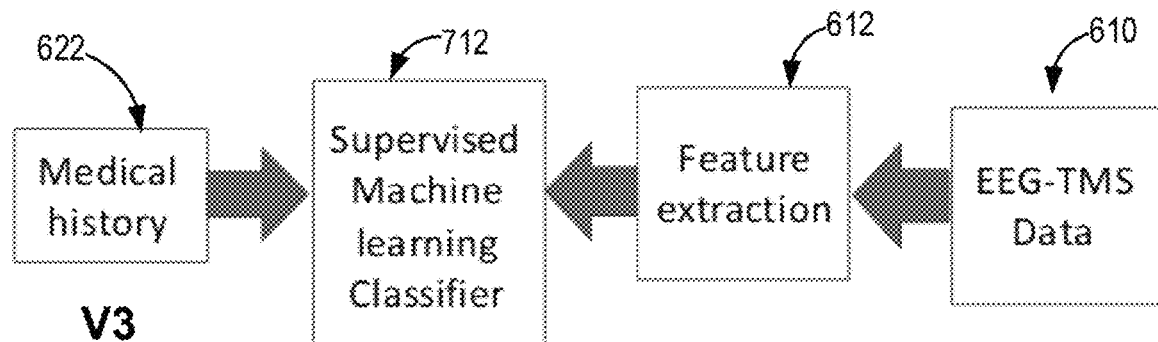

According to some embodiments, the MLC training method is according to at least one method selected from:

each database-subject's DELPhi_feature1 and DEL-Phi_feature2 are provided as training inputs, and their respective vectors V1 and V2 are provided as training outputs (demonstrated in FIG. 6A);

each database-subject's DELPhi_feature4 is as training input, and their respective output vector V3 is provided as training output (demonstrated in FIG. 6B);

each database-subject's DELPhi_feature3 together with subject's known medication/drug treatment are provided as training inputs, and their respective vector V3 provided as training output (demonstrated in FIG. 6C); and any combination thereof.

Reference is now made to FIGS. 5A and 5B schematically, which demonstrate the two MLC use phases: Training (FIG. 5A) and Application (FIG. 5B), according to some embodiments of the invention. At the Training phase 600, the supervised MLC 710 is provided with:

features extracted from the EEG signals 610 (measured after providing TMS stimulation/s) of database subjects, provided as training inputs; and the database-subjects' known imaging information and clinical data, provided as training outputs.

At the Application phase 800, the trained supervised MLC 720 is provided with EEG signals 810 of a subject (a new subject with no identified classifications), measured after providing TMS stimulation/s, provided as an input to obtain an output of evaluated imaging information and/or clinical data.

Figure 6C:
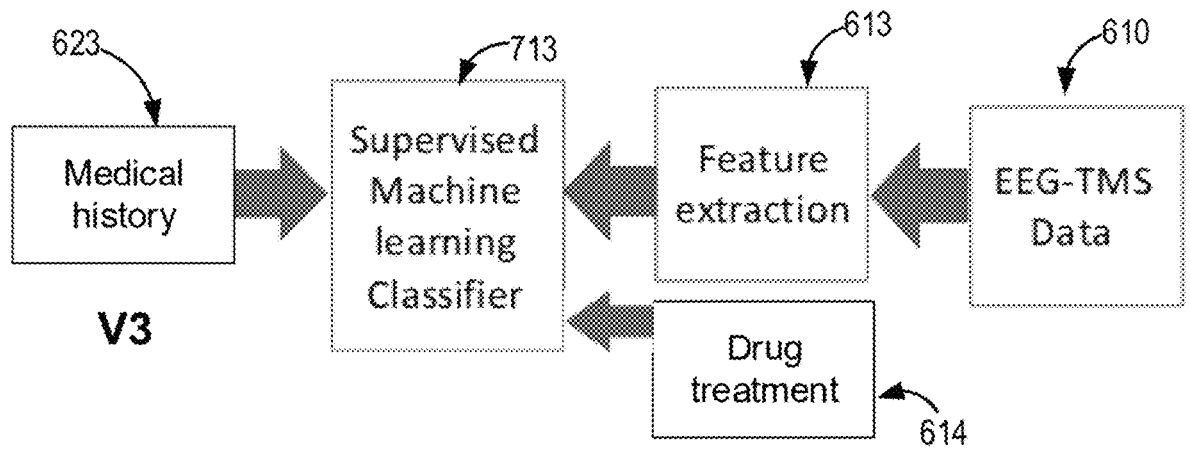

Reference is now made to FIGS. 6A, 6B and 6C schematically demonstrating examples for different Training phases, according to some embodiments of the invention.

According to some embodiments, and as demonstrated in FIG. 6A, the MLC comprises a registration based supervised MLC 711 provided with:

features 611 extracted from the EEG signals 610 (measured after providing TMS stimulation/s) of database subjects, provided as training inputs; and the brain MRI-T1: Gray matter and White matter volume or surface of cortical and subcortical areas, referred as vector "V1" 622, and the brain MRI-DWI (diffused tensor imaging): White matter measures of Fractional anisotropy (FA) and Mean diffusivity (MD), referred as vector "V2" 623; all extracted from the database subjects' known MR imaging information 621, and provided as the MLC training outputs.

According to some embodiments, and as demonstrated in FIG. 6B, the MLC comprises a supervised MLC 712 provided with:

features 612 extracted from the EEG signals 610 (measured after providing TMS stimulation/s) of database subjects, provided as training inputs; and database subjects known medical history and classifications 622, provided as the MLC training outputs.

According to some embodiments, and as demonstrated in FIG. 6C, the MLC comprises a supervised MLC 713 provided with:

features 613 extracted from the EEG signals 610 (measured after providing TMS stimulation/s) of database subjects together the database subjects' known medication/drug treatment 614, provided as training inputs; and database subjects known medical history and classifications 623, provided as the MLC training outputs.

Figure 7A:
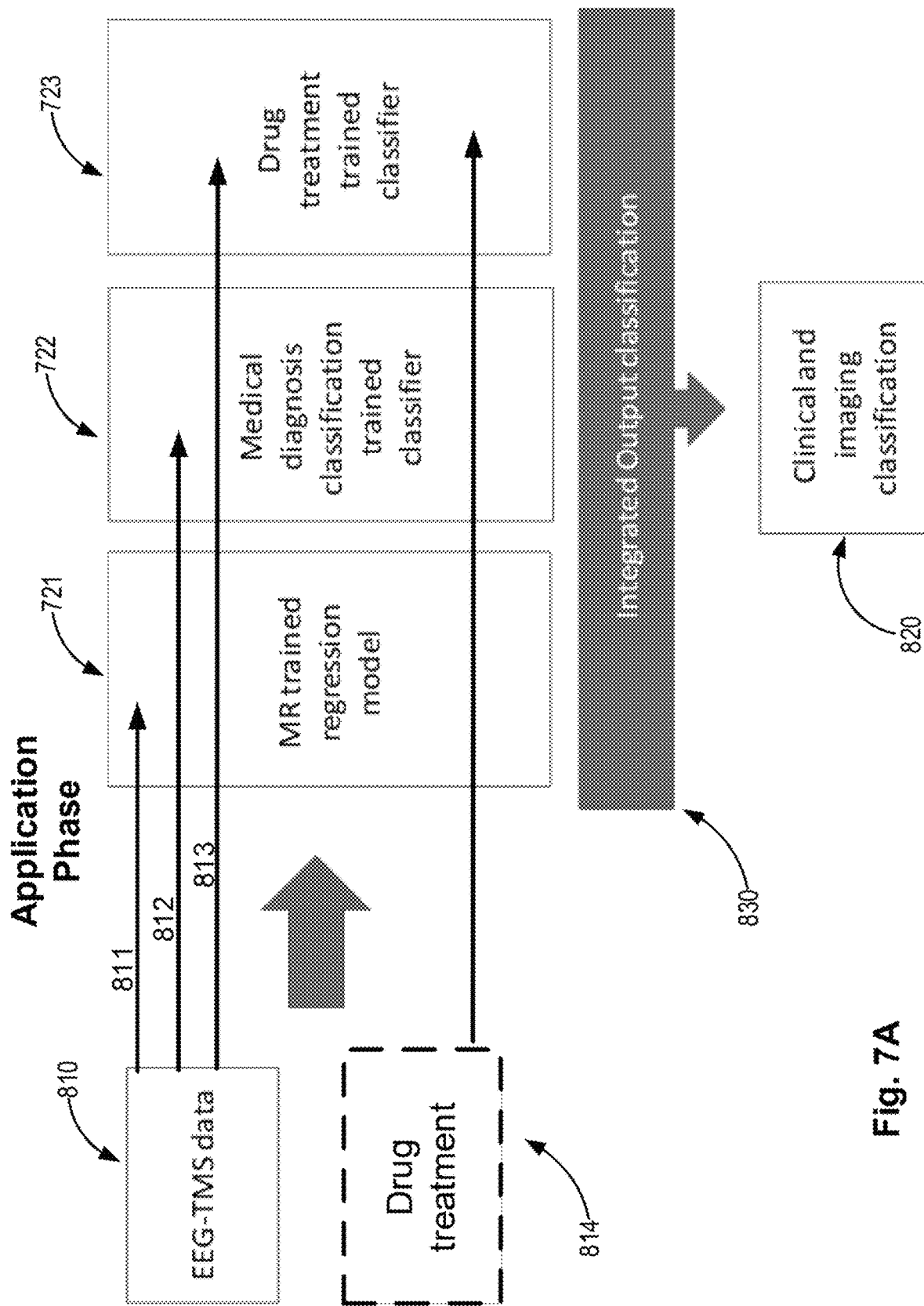
FIGS. 7A and 7B schematically demonstrate an example for the Application phase of integrated MLC modules (FIG. 7A) and their method steps (FIG. 7B), according to some embodiments of the invention.
Figure 7B:
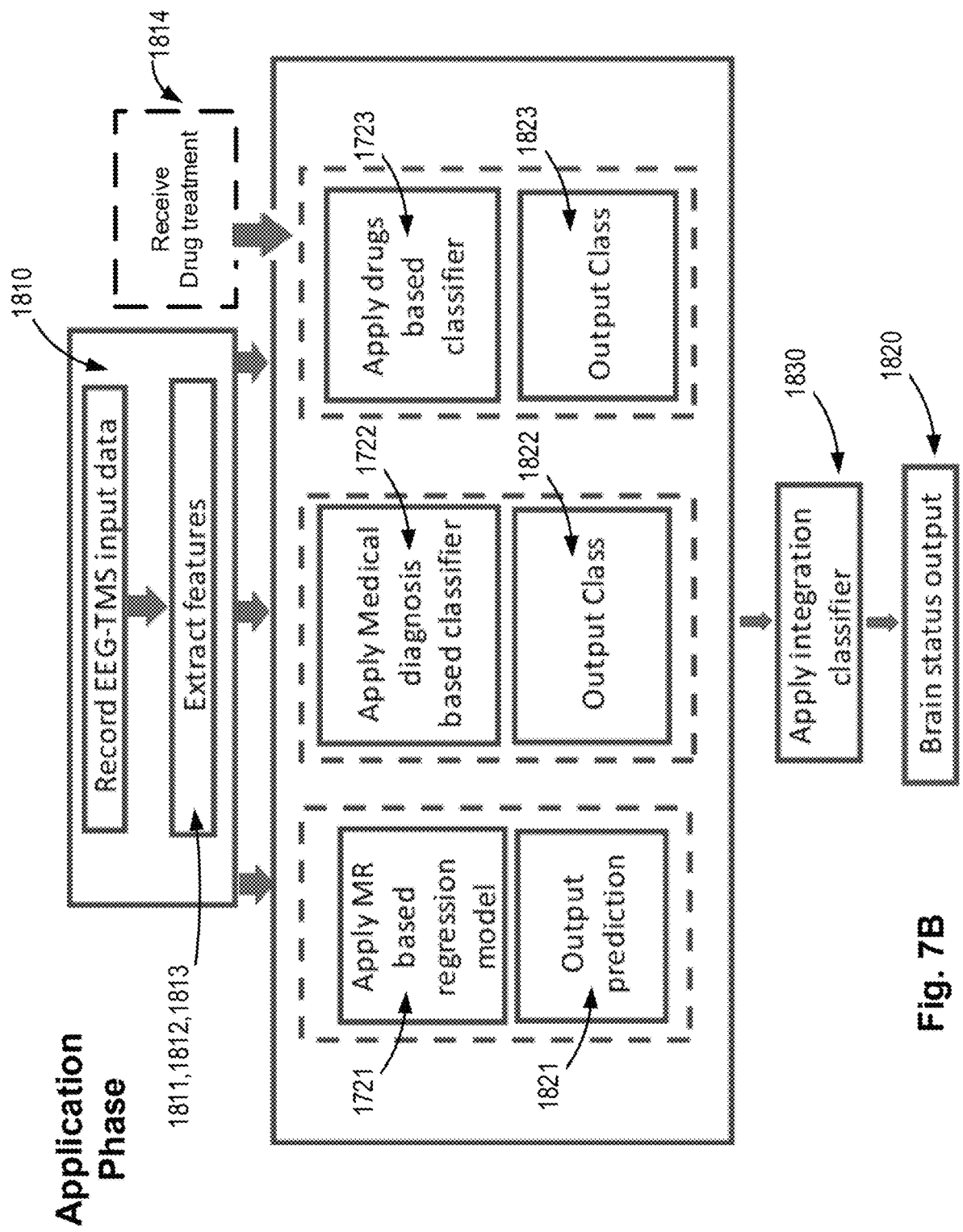

Reference is now made to FIGS. 7A and 7B schematically demonstrating an example for the Application phase of integrated MLC modules (FIG. 7A) and their method steps (FIG. 7B), according to some embodiments of the invention.

According to some embodiments, and as demonstrated in FIG. 7A, the trained MLC trained MLC modules 721,722, 723, following the training phase respectively demonstrated in FIGS. 6A-6C, are applied with selected input vectors 811,812,813 extracted from a subject's (a new subject with no identified classifications) the EEG signals 810 and optionally drug treatment 814; the outputs of the trained modules 721,722,723 is integrated in the integrated output classification module 830, which is configured to provide clinical and imaging classification 820.

FIG. 7B demonstrates the method steps for the integrated Application phase, using the MLC modules demonstrated in FIG. 7A, according to some embodiments of the invention. The method steps comprising:

recording/receiving 1810 EEG signals 810 and optionally receiving 1814 the drug treatment 814, of a subject (a new subject with no identified classifications);

extracting 1811,1812,1813,1814 input vectors from the received/recorded data 810,814, for each of the trained MLC modules 721,722,723;

selectively applying 1721,1722,1723 the trained MLC modules 721,722,723 on their respective input vectors 811,812,813,814 for obtaining 1821,1822,1823 their respective output classes 821,822,823;

applying 1830 an integrated classifier 830 on the obtained output classes 821,822,823, for obtaining 1820 an integrated brain status output 820.

According to some embodiments an apparatus 100 is provided configured to evaluate brain state of a subject, the apparatus comprising:

a directed inspective/diagnostic stimulation unit 202, configured to induce TMS diagnostic stimulation to a predetermined brain region of the subject;

a brain activity EEG sensor unit 203, configured to measure a neural activity response to the diagnostic stimulation induced by the directed brain stimulation unit; and at least one processing circuitry 201 and at least one memory unit, in wired or wireless communication with the brain activity sensor unit, the processing circuitry is configured to execute the method steps according to any one of the preceding method embodiments for classifying a brain status of a subject, from a neural activity response of the subject to an induced TMS stimulation.

According to some embodiments a transient and/or non-transient computer readable medium (CRM) is provided, such that when loaded into a memory of a computing device and executed by at least one processor of the computing device, is configured to execute at least the steps of the computer implemented method according to any one of the preceding method embodiments for classifying a brain status of a subject, from a neural activity response of the subject to an induced TMS stimulation.

In the following non-limiting examples are provided, to demonstrate at least some of the provided embodiments.

EXAMPLES

Experiment Methods
TRANSCRANIAL MAGNETIC STIMULATION: TMS was performed with a MagPro R30 stimulator (MagVenture, Denmark) and an MCF-B65-HO figure-8 Coil (Mag Venture, Denmark). Resting motor threshold (rMT) was obtained at the beginning of every session by stimulating the left motor cortex and defined as the intensity that produced a visible twitch in adductor policis brevis on 50% of stimulations (Rosanova et al.). Each test-run entailed about 420 pulses (biphasic pulses at 280 mSec pulse width) at ranging intensities, from 50% to 120% of the rMT Stimulation varied in frequency of continues stimulation of 0.1 Hz, 1 Hz and paired pulse stimulation on 20 Hz with inter-burst-interval of 30 seconds. A thin (0.5 mm) foam pad was attached to the TMS coil to minimize electrode movement and bone-conducted auditory artefact. Participants were instructed to keep their eyes closed throughout the examination. TMS coil was placed over the left side of the cortical motor (M1) region in the appropriate manner (The coil was held tangentially to the scalp at 45° to the midline) and rMT was measured to ensure proper placement of the stimulating coil. Intensities of stimulation increase gradually from 50% of the personalized determined resting motor threshold (rMT) up to 120% of the rMT in a specific and predetermined protocol of stimulation. Evoked response of the stimulated hotspot (weighted average of three sensors in the proximity of the point of stimulation: C3, C5, CP1) and contralateral to the stimulated hotspot (right M1: C4, C6, CP2) were analyzed and an I/O curve of regional response was described per individual. Clarification: the EEG response to TMS stimulation is calculated as the average signal recorded from three electrodes in the left motor area hemisphere. The electrodes are named: C3, C5 and CP1. The hotspot electrodes in the right motor area hemisphere are named: C4, C6 and CP2.

FIGS. 8B, 8C, 8D and 8E demonstrate examples for intensity dependent TMS evoked response in young healthy subjects; FIG. 8B demonstrates representative grand average traces of left M1 hotspot (upper bundle of subjects) and right M1 hotspot (lower bundle of same subjects); FIG. 8C demonstrates mean healthy population charge transfer change by stimuli intensity of left hotspot (green) and right hotspot (turquoise); FIG. 8D demonstrates mean healthy population P60-N100 Slope change by stimuli intensity of left hotspot (green) and right hotspot (turquoise); and FIG. 8E demonstrates mean healthy population N100-P180 slope change by stimuli intensity of left hotspot (green) and right hotspot (turquoise); in the examples 100%=2 Tesla.

SHAM STIMULATION: for sham (Placebo) TMS stimulation the 8-figure coil was placed over the left side of the cortical motor (M1) region, in the exact same orientation as for non-sham stimulation; the purpose is to demonstrate the lack of neuro-physiological response in the absence real TMS stimulation. After placement, the coil was moved 1 cm away from the scalp and a silicone cube (1 cm×3 cm) filled with artificial cerebral spinal fluid (ACSF) was placed in between. Stimulation protocol (duration, intensities and frequencies) was maintained the same as in non-sham. The purpose of the sham stimulation was to demonstrate the lack of neuro-physiological response in the absence real TMS stimulation.

ELECTROENCEPHALOGRAPHY: 32-channel EEG data was obtained using two 32-channel TMS compatible BrainAmp DC amplifiers (5 kHz sampling rate; ±16.384 milli-volt measurement range; analog low pass filter 1 kHz). These were attached to the Easy EEG cap (EasyCap GmbH, Germany) with Ag—AgCl electrodes. Electrode impedances were kept below 5 kilo-Ohm. The reference and ground electrodes were affixed to the ear lobes. EEG data was recorded using BrainVision Recorder software (Brain Products GmbH, Germany) All data was pre-processed and analyzed using the fully automated developed DELPhi algorithm and carried out on MATLAB (R2016b, The Mathworks Inc, MA).

Study Subjects Group 1:

Four study groups were evaluated, each group was defined as followed:
 (a) young and healthy 25-40 years old (yo),
 (b) healthy adults, 50-70 years old;
 (c) healthy adults over 70 years old;
 (d) early dementia diagnosed subjects, over 65 years old.

Healthy subjects in all ages were defined as follows: determined healthy by a physician, with a clear MRI scan, not taking any prescribed medication, normal computerized cognitive evaluation over 95 mean global score normalized to age related population, and clear neurocognitive evaluation by neuropsychologist.

According to some embodiments, mild Dementia subjects were defined as follows: determined having dementia diagnosis by a physician and neuropsychologist, Montreal cognitive assessment (MoCA) score between 11 and 21, Neurtrax BrainCare computerized testing memory test at least 1.5 standard deviations (STDV) below age related norm, and at least one other test of executive function, visual spatial memory or verbal function, with minimum of 1.5 STDV below norm.

All patients had MRI scans, 1-2 weeks before DELPhi evaluation. Imaging was done with a 3 Tesla system (20 channels, MAGNETOM Skyra, Siemens Medical Solutions). The MRI protocol included T2 weighted, T1 weighted, FLAIR and susceptibility weighted imaging (SWI) sequences. All scans were analyzed by a neuroradiologist.

Assessment of cognitive functions was performed by trained neuropsychologists using the standard Montreal cognitive assessment (MoCA) test and NeuroTrax computerized BrainCare cognitive battery tests (NeuroTrax Corp., TX) (Dwolatzky et al., 2003).

DATA ANALYSIS: The analysis was performed online automatically using the currently provided DELPhi acquisition and analysis methods. According to some embodiments, charge transfer was measured as the area under the curve between 30 and 300 mSec of the evoked response. According to some embodiments, Inhibition-excitation balance (relation) was determined by calculating the slopes of the evoked response. Slopes were measured between 60 mSec and 100 mSec (P60-N100) and between 100 mSec and 180 mSec (N100-P180) (as demonstrated in FIGS. 8D-8E); e.g. slop of a straight line connecting two points. According to some embodiments, short term plasticity, which corresponds to the network ability to change the ratio between excitation and inhibition, was expressed by the ratio between slopes evoked in different frequencies of stimulation (e.g. 0.1, 1, 20 Hz) (as demonstrated in FIGS. 9A-9D). Values are expressed as mean+/−standard error (SE).

FIGS. 9A, 9B, 9C and 9D demonstrate frequency dependent TMS evoked response in young healthy subjects. FIG. 9A demonstrates representative grand average traces of M1 left hotspot (upper) and right M1 hotspot (lower); green color for 0.1 Hz, orange color for 1 Hz, blue color for 20 Hz; FIG. 9B demonstrates representative charge transfer change by frequency of stimulation of M1 left hotspot (green) and M1 right hotspot (turquoise); FIG. 9C demonstrates representative N100-P180 Slope change by frequency of stimulation of M1 left hotspot (green) and M1 right hotspot (turquoise); and FIG. 9D demonstrates representative P60-N100 slope change by frequency of stimulation of M1 left hotspot (green) and M1 right hotspot (turquoise).

STATISTICAL ANALYSIS: Statistical data analysis was performed using GraphPad Prism 7. Test retest measures were compared by Pearson's correlation and Bland-Altman plot. Error bars shown in the figures represent standard error of the mean (s.e.m.). The number of subjects is defined by N. One-way ANOVA analysis with post hoc Tukey was used to compare subject groups. Student's un-paired t-test has been used were used to compare two. * p<0.05;  p<0.01; * p<0.001, ns—non-significant.

Experimental Results—Group 1

According to some embodiments, the above mentioned methods are provided to identify and characterize the physiological profile of brain network functionally in order to differentiate healthy populations, young, adult and aging, from brain network functionally characterizing pathologically abnormal brain functionality.

Neuronal network function is characterized by a tightly maintained balance of excitation and inhibition correlated with levels of activity. The balance between excitation and inhibition reflects the strength of the network. Response to TMS depends on the excitation-inhibition balance of the cortical network (Silvanto et al. 2008; Rogasch J Neurophysiol 2012). According to some embodiments, in order to assess the strength of the network an Input-Output (I/O) function curve is defined per individual subject, referring to the relationship between the excitatory input to the cortical region and the strength of the generated TMS evoked EEG response. A brain network I/O curve, mainly represents a sigmoidal function, which characterized according to so embodiments, by connecting its edge points (maximum and minimum) thereby defined by two components: the threshold and the gain (slope).

Reference is made again to FIGS. 8B-8E, which demonstrate intensity dependent TMS evoked response in young healthy subjects. Evaluating brain network strength in healthy population (25-45 years old, defined as healthy by a physician, with no abnormalities in an MRI, not taking any prescribed medication, normal cognitive evaluation) reveals an increase in the evoked response correlated with the increase in the intensity of stimulation (FIG. 8B, different colors for different intensities). A single TMS pulse delivered over the left primary motor cortex (M1) results in a sequence of positive and negative EEG peaks as previously reported (Ilmoniemi and Kicic 2010) at specific latencies in both hemispheres (left-ipsilateral to stimuli; right-contralateral to stimuli). Most pronounced features of response are the positive peaks at 60 mSec and 180 mSec and a negative peak at 100 mSec (P60, N100, P180) following stimuli, as demonstrated in FIG. 8B. Several electrophysiological parameters can be quantified from the evoked response. The first, well established electrophysiological parameter, is the charge transfer of evoked response (Q) calculated as the area under the curve.

As expected, the charge transfer, demonstrated in FIG. 8C, increases with the increased intensity of stimulation in both hemispheres. The left, stimulated hemisphere, shows a stronger intensity dependent increase in charge transfer with an average total increase of 180% in the 55% intensity compared to the 30% intensity (of maximal device intensity of stimulation), $p<0.0001$ in left hotspot linear regression slope 11,445 ($R^2=0.72$), and an average total increase of 130%, $p<0.05$ in right hotspot linear regression slope 4908 ($R^2=0.71$), $p<0.05$ N=33.

Intensity dependent effects on the three main peaks (P60, N100, P180) represent patterns of the individual physiological response giving an important understanding on changes in cortical excitability and inhibition, however, these peaks (P60, N100, P180) vary in their specific timing (50-70 mSec, 90-120 mSec, 150-210 mSec respectively) for example, due to any cortical changes as age dependent atrophy. Therefore, the slope of responses (P60-N100; N100-P180) were measured giving a more robust and reliable parameters to monitor, understanding any functional change in the network will be reflected as change in the measured slopes. P60-N100 slope, as demonstrated in FIG. 8D, is enhanced with the increased intensity of stimulation in both hemispheres, with an average total decrease of 376% in 55% compared to 30% $p<0.001$ in left hotspot linear regression slope −0.015 ($R^2=0.92$), and an average total decrease of 172%, $P<0.001$ in right hotspot linear regression slope −0.005 ($R^2=0.78$), $p<0.01$ N=33. N100-P180 slope as demonstrated in FIG. 8E, does not show any significant intensity dependent change above 30% intensity of stimulation with an average total decrease of 13% in 55% compared to 30% $p>0.05$ in left hotspot linear regression slope −0.0005 ($R^2=0.31$), and 15% increase, $P>0.05$ in right hotspot linear regression slope 0.0007 ($R^2=0.5$), $p<0.05$ N=33.

As mentioned above, a sham-placebo stimulation was performed as described in the methods section. Sham stimulation revealed that all referenced parameters are relevant brain network neuronal responses, as demonstrated in FIG. 10A.

FIGS. 10A, 10B, 10C, 10D and 10E demonstrate Sham Controlled TMS evoked stimulation in healthy subjects, displayed via frequency dependent behavior, indicating reliability of the measured parameters and therefore mechanisms of network short term plasticity (N=5; p<0.01). FIG. 10A demonstrates representative single pulse (0.1 Hz) with representative average traces of left M1 hotspot in healthy subjects; black color for real stimulation and green color for sham stimulation; FIG. 10B demonstrates representative inhibitory stimulation (1 Hz) representative grand average traces of left M1 hotspot; black color for real stimulation and green color for sham stimulation; FIG. 10C demonstrates representative excitatory (20 Hz) representative grand average traces of left hotspot healthy subjects; black color for real stimulation and green color for sham stimulation; FIG. 10D demonstrates representative grand average traces of real TMS stimulation at 0.1 Hz, 1 Hz, 20 Hz (black, green, blue respectively) over the left M1 hotspot; and FIG. 10E demonstrates representative grand average traces of sham TMS stimulation at 0.1 Hz, 1 Hz, 20 Hz (black, green, blue respectively) over the left M1 hotspot).

Short term plasticity is evaluated in electrophysiology by changing the frequency of stimulation and measuring the 'history dependency' of the evoked response. TMS stimulation were introduced in two intensities, sub and suprathreshold (80% and 120% of rMT respectively). Three stimulation frequencies were tested, 0.1 Hz (single pulse, showing no 'history dependency' (R. Chen May 1997; Neurology), 1 Hz (low frequency (LFrTMS)— evoking inhibition of response in a mechanisms that may by similar to long term depression —LTD (Muellbacher W, Clinical Neurophisiology 2000; R. Chen May 1997; Neurology; Fitzgerald et al, clinical neurophysiology 2006) and 20 Hz (high frequency (HFrTMS)—evoking excitation of evoked response (Fumiko Maeda et al, clinical neurophysiology, May 2000; MauroGarcia-Toro et al. Psychiatry Research: Neuroimaging 2006; Chul Kim et al. Ann Rehabil Med. 2014; Mansur C G, Neurology 2005; Fregni F, Stroke 2006; Peinemann A, Clin Neurophysiol 2004)).

Reference is made again to FIGS. 9A-9D, which demonstrate frequency dependent TMS evoked response in young healthy subjects. FIG. 9A demonstrates that both hemispheres (ipsi- and contra-lateral to stimuli) demonstrated a similar frequency dependent behavior of evoked response in both intensities of stimulation (sub- and supra-threshold, data not shown). A significant decrease in all measured parameters was recorded in 1 Hz stimulation compared to 0.1 Hz. Charge transfer, as demonstrated in FIG. 9B was reduced in 1 Hz by 39% in left hotspot and 54% in right hotspot in subthreshold intensity (p<0.001) and 30% in left hotspot and 38% in right hotspot in supra-threshold intensity (p<0.001; N=33); N100-P180 slope, as demonstrated in FIG. 9C, was reduced by 83% in 1 Hz stimulation in left hotspot and 73% in right hotspot in subthreshold intensity (p<0.001) and 78% in left hotspot and 51% in right hotspot in supra-threshold intensity (p<0.01; N=20). P60-N100 slope, as demonstrated in FIG. 9D, was reduced in 1 Hz by 40% in left hotspot and 80% in right hotspot in subthreshold intensity (p<0.001) and 32% in left hotspot and 42% in right hotspot in supra-threshold intensity (p<0.001; N=20. The reduction in response evoked in 1 Hz compared to 0.1 Hz reflect network inhibition. 20 Hz stimulation shows no significant change in charge transfer compared to 0.1 Hz and a significant increase in response of 150% in left hotspot and 255% in right hotspot compared to 1 Hz in subthreshold intensity (P<0.001, N=20) (FIG. 6B). N100-P180 slope was not significantly changed compared to 0.1 Hz or 1 Hz; P60-N100 slope significantly changed from negative to positive evoked by 20 Hz stimulation both hemispheres hotspots in subthreshold and suprathreshold intensities compared to 1 Hz and 0.1 Hz (p<0.001; N=20) (FIGS. 9C, 9D) reflecting the mechanism of excitatory response evoked by high frequency of stimulation. The most prominent frequency dependent change in evoked response was demonstrated between 0.1 Hz and 1 Hz of stimulation.

In order to establish system credibility, measured data reproducibility test was performed. Test-retest, evaluation of the collected and analyzed parameters (charge transfer, slopes of evokes response and short-term plasticity (STP) calculated as the ratio between measured parameters in 1 Hz and 0.1 Hz) was performed. Results demonstrate high reliability and reproducibility of the DELPhi analyzed physiological parameters displaying Pearson's correlation r significantly higher than 0.9 in all measured parameters (FIG. 11A-E) and a Bland-Altamn plot with 95% limits of agreement for each parameter.

Figure 11A:
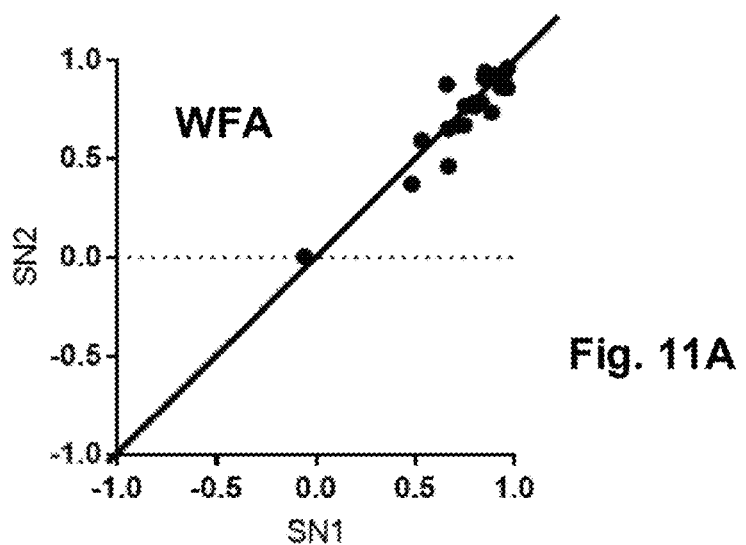
FIGS. 11A, 11B, 11C, 11D and 11E demonstrate representative test vs. re-test of TMS evoked response, according to some embodiments of the invention.
Figure 11B:
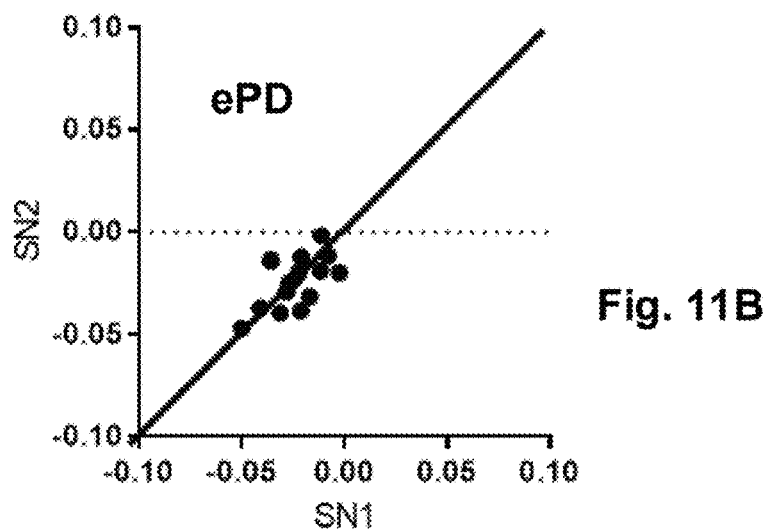
Figure 11C:
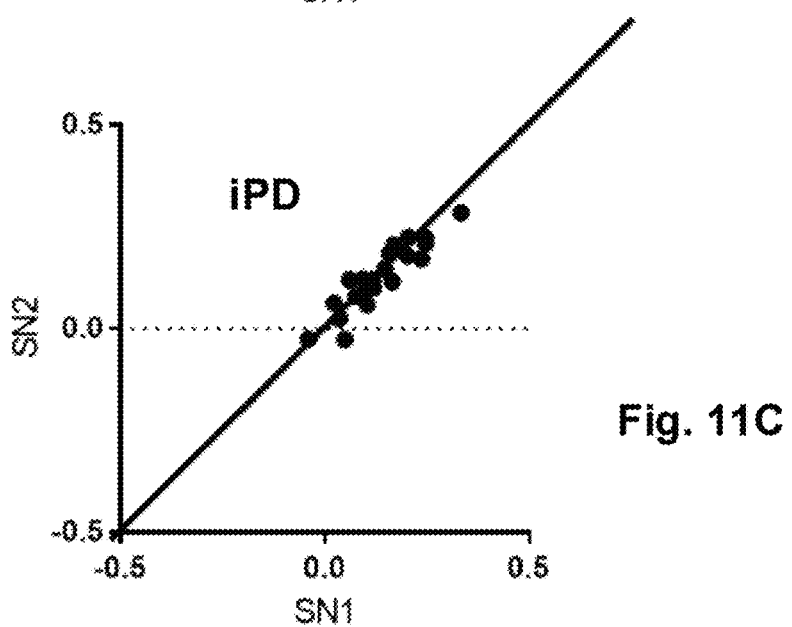
Figure 11D:
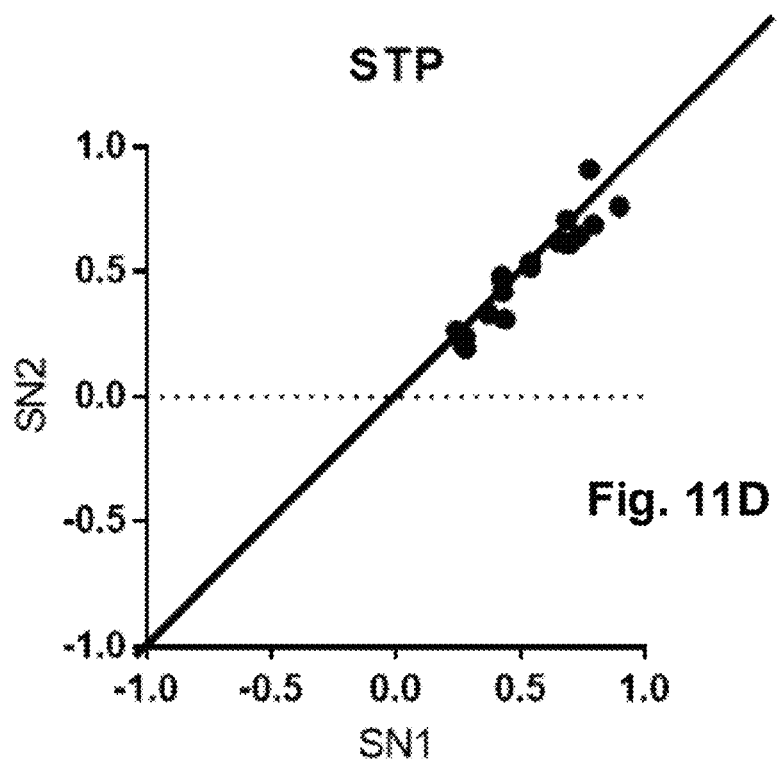
Figure 11E:
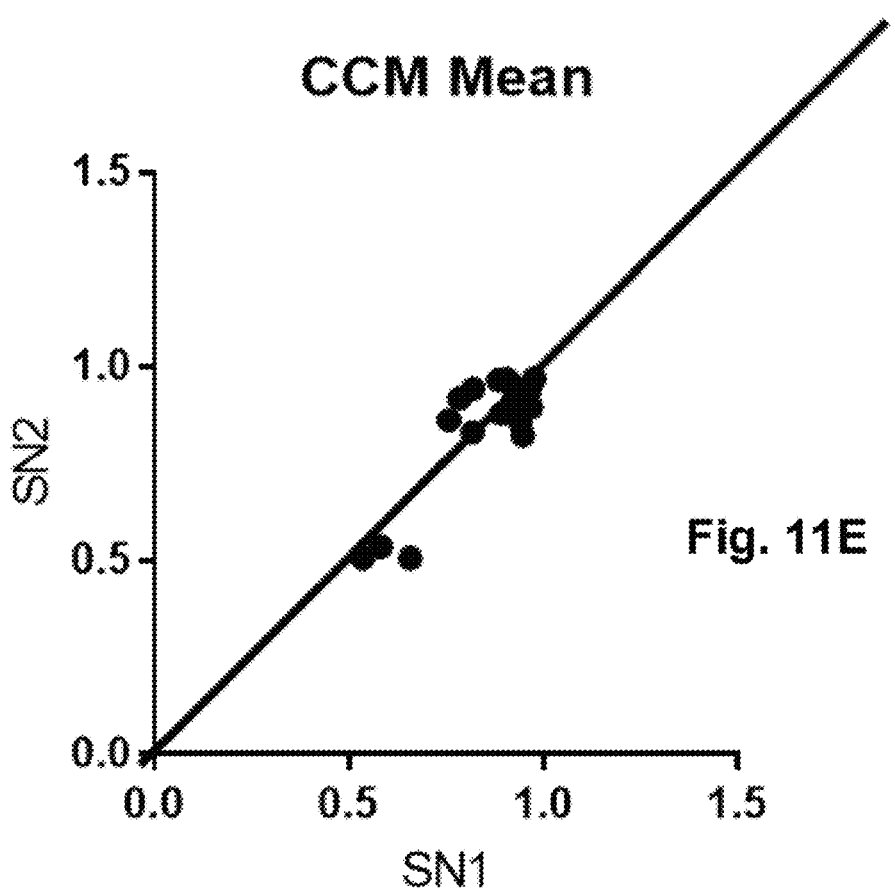

FIGS. 11A-11E demonstrate representative test (SN1) vs. re-test (SN2) of TMS evoked response. 12 healthy subjects (N=12) were evaluated in two sessions (session 1—SN1; session 2—SN2), performed at least 24 hours apart and up to one week; black dots represent the ratio between the two sessions of the same subject. FIG. 11A demonstrates mean wave form adherence (WFA)-correlation to healthy of a subject's SN1 versus SN2 r=0.92, p<0.0001. FIG. 11B demonstrates mean early phase deflection/early slope (ePD) of a subject's SN1 versus SN2 r=0.93, p<0.0001. FIG. 11C demonstrates mean late phase deflection/late slope (LPD) of a subject's SN1 versus SN2 r=0.95, p<0.0001. FIG. 11D demonstrates mean short term plasticity (STP) of a subject's SN1 versus SN2 r=0.9, p<0.0001. FIG. 11E demonstrates mean connectivity coherence map (CCM) of a subject's SN1 versus SN2 r=0.85, p<0.001. Accordingly, FIGS. 8A-8E demonstrate the high reproducibility and reliability of the measurement performed by DELPhi.

Figure 12A:
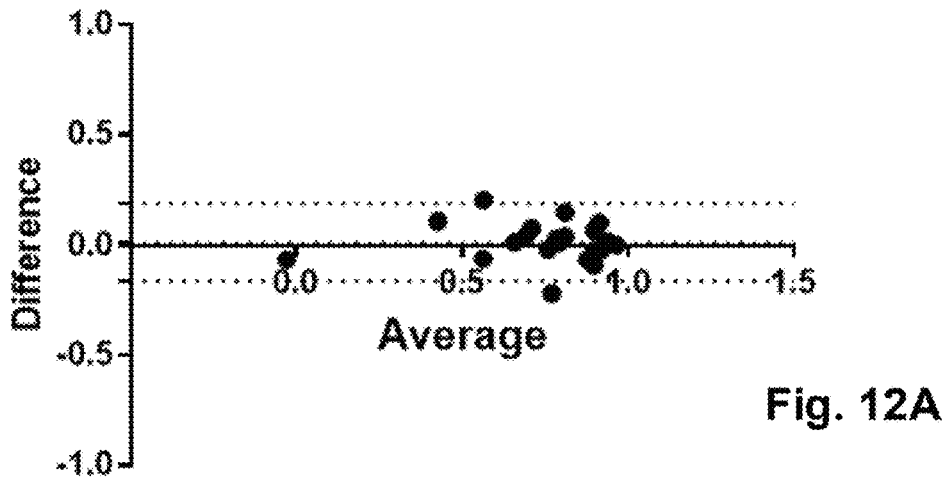
FIGS. 12A, 12B, 12C, 12D and 12E demonstrate representative test vs. re-test of TMS evoked response according to Bland-Altman plot, according to some embodiments of the invention.
Figure 12B:
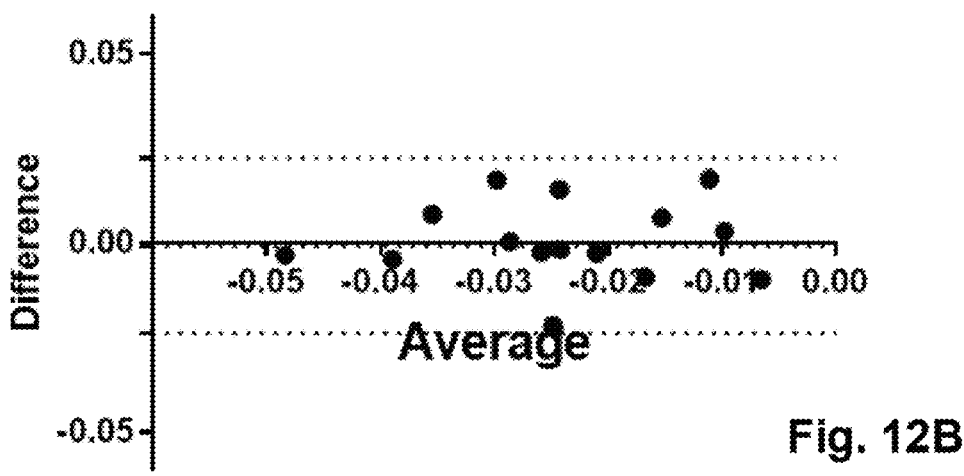
Figure 12C:
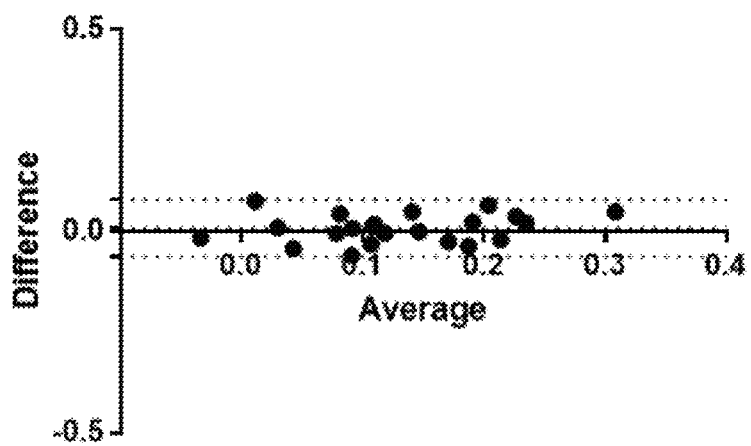
Figure 12D:
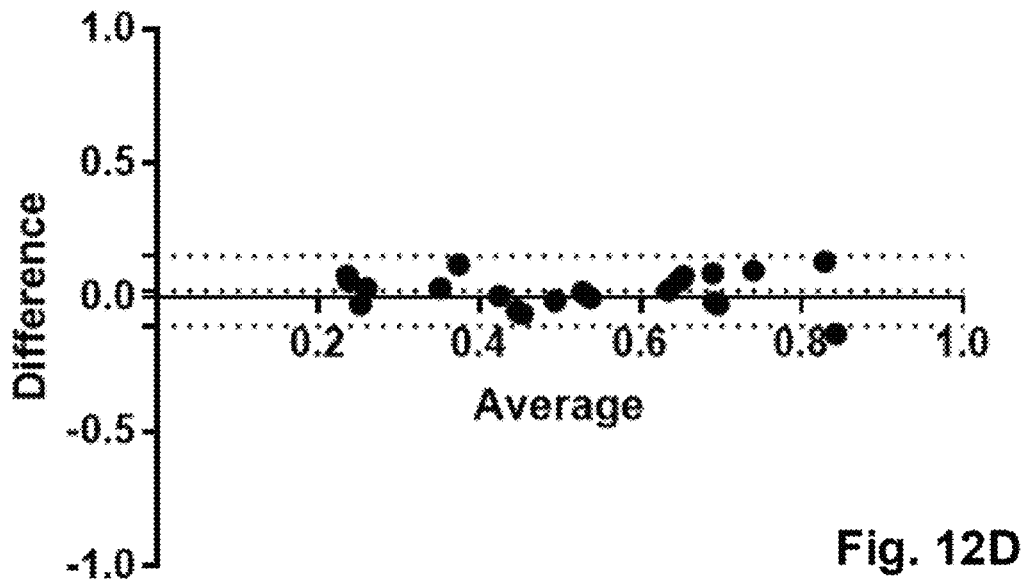
Figure 12E:
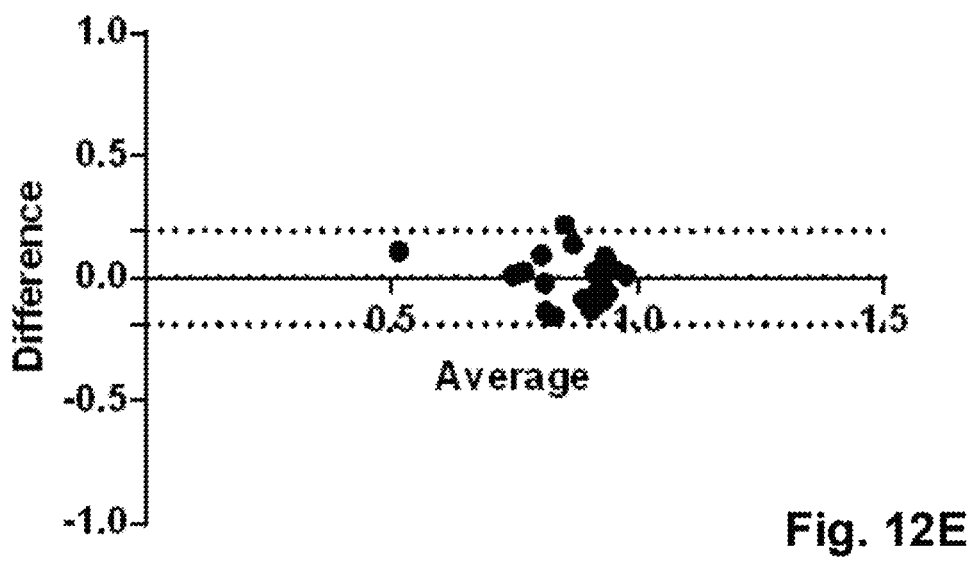

FIGS. 12A-12E demonstrate representative test (SN1) vs. re-test (SN2) of TMS evoked response according to Bland-Altman plot. The black dots represent 12 different subjects. The difference between values measured at the two sessions are plotted against their mean (the middle dotted-line), for each subject (black dots). The dotted lines represent the mean (middle dotted line) and limits (upper/lower) of agreement (LoA) of the differences between the two sessions across subjects. FIG. 12A demonstrates mean wave form adherence (WFA)-correlation to healthy of a subject's SN1 versus the subject's SSN2, per each subject; FIG. 12B demonstrates mean early phase deflection/early slope (ePD) of a subject SN1 versus the subject's SN2, per each subject; FIG. 12C demonstrates late phase deflection/late slope (LPD) of a subject's SN1 versus the subject's SN2, per each subject; FIG. 12D. demonstrates mean short term plasticity (STP) of a subject's SN1 versus the subject's SN2, per each subject; FIG. 12E demonstrates mean connectivity coherence map (CCM) of a subject's SN1 versus the subject's SN2, per each subject.

Based on the provided ability to measure physiological properties of cortical brain network functionality, in a reliable manner, according to some embodiments a tool is provided configured to examine these parameters' change with age, and differentiate this normal-healthy physiological process from an abnormal, pathological, degenerative deterioration on brain network functionality. Accordingly, the present invention provides a new clinical tool for evaluating and monitoring brain aging and health. The same paradigm of data acquisition and analysis was performed on four populations:

(a) healthy young, 25-40 years old;
(b) healthy elderly, 50-70 years old;
(c) healthy elderly, over 70 years old; and
(d) early dementia diagnosed, over 65 years old.

According to some embodiments, the ratio between the measured slopes of the evoked response (P60-N100; N100-P180) reflect the balance between excitation and inhibition in the regional cortical network. Cortical excitation-inhibition balance changes during normal aging and neurodegenerative pathological deterioration (Legon W et al, *Cerebral Cortex*, 2016; Grady C L et al, 2003, *Hippocampus*; Wang L, 2010, *Neuroimage;* Mormino E C, 2011, *Cereb Cortex*). Hence, examination of the regional slopes ratio is provided as a significant physiological measurement tool for monitoring brain health through aging.

Reference is made to FIGS. 13A-13D, which demonstrate a significant age dependent change in the excitation-inhibition balance (relation), which was measured in all the measured cortical regions, and is reflected as a change in the ratio between slopes of the evoked response. FIGS. 13A-13D demonstrate representative N100-P180 slope vs. P60-N100 slope. FIG. 13A demonstrates representative temporal hotspot; FIG. 13B demonstrates representative parietal hotspot; FIG. 13C demonstrates representative frontal hotspot; and FIG. 13D demonstrates representative occipital hotspot; full circle—left hotspot; empty circle—right hotspot; blue color for young healthy subjects (25-45 years old; N=40); green color for adult healthy subjects (50-70 years old; N=34); yellow color for old healthy subjects (over 70, N=18); and red color early Dementia subjects (over 70; N=20).

Figure 14A:
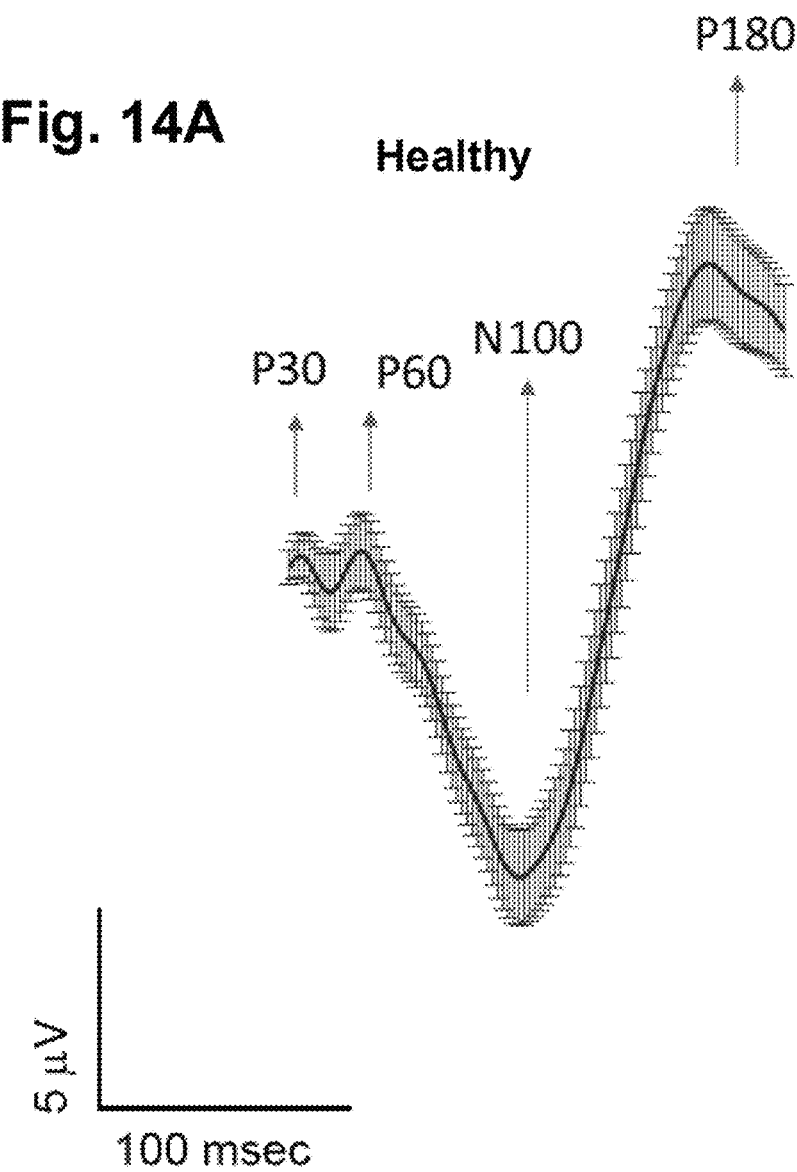
FIGS. 14A, 14B and 14C demonstrate representative measurement of EEG signal [μv] in time [msec]
Figure 14B:
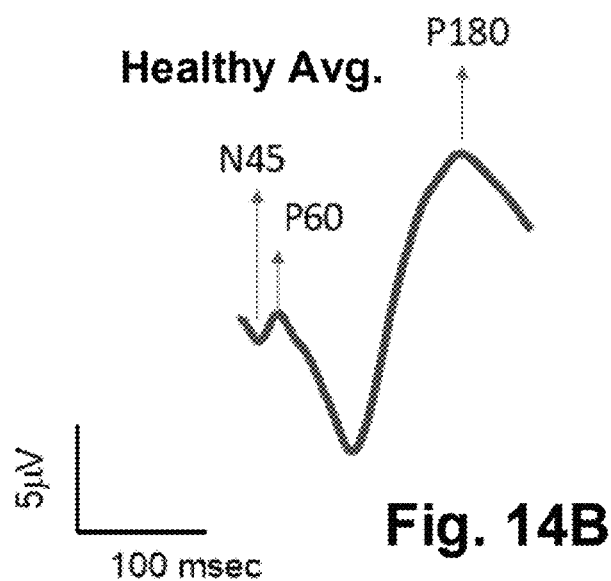
Figure 14C:
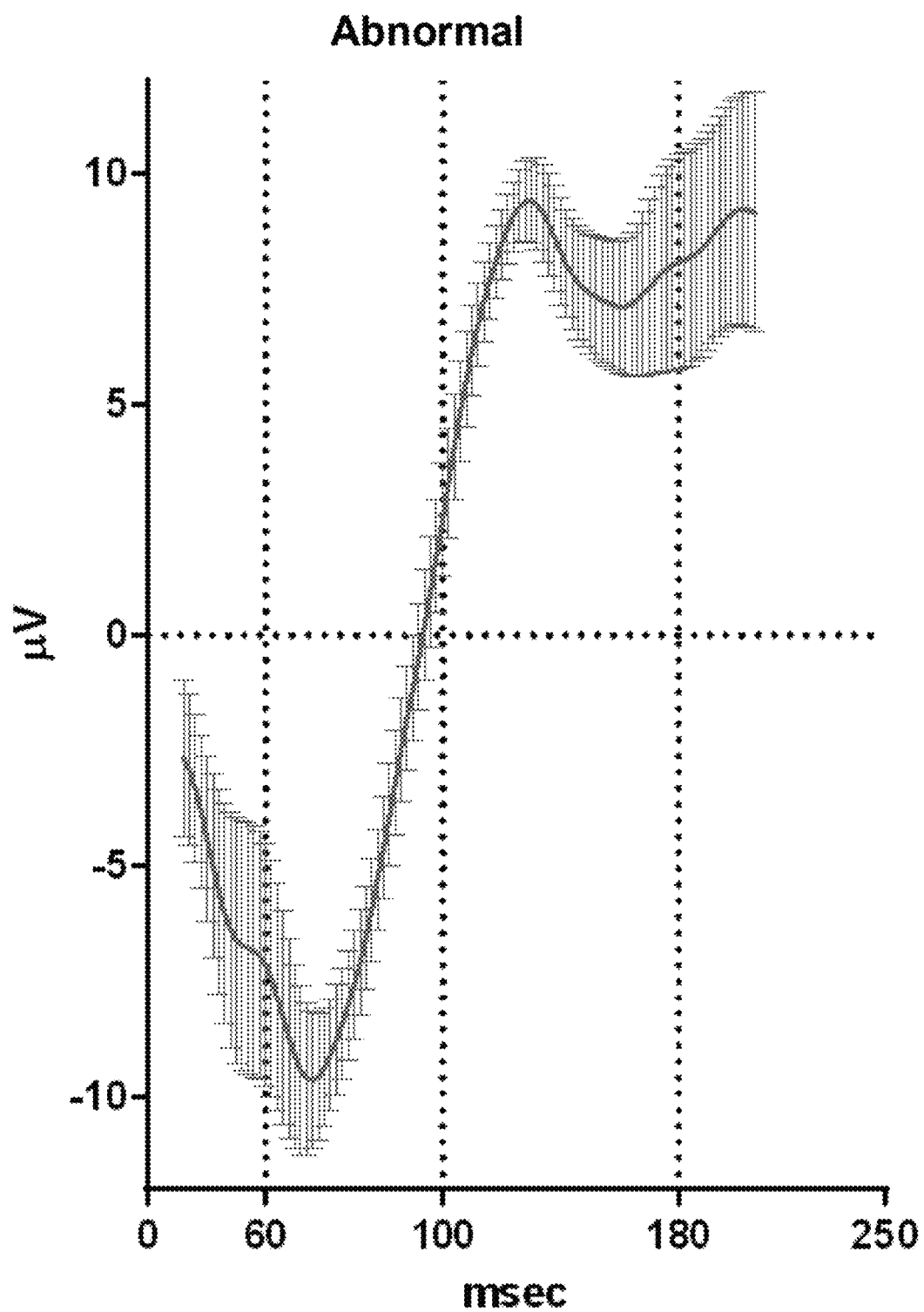

Subject population clustering demonstrates that the P60-N100 slope parameter is a significant indicator for Dementia in both right- and left-frontal and parietal areas. Dementia subjects display a significant change of the slope from positive to negative values (p<0.001) versus the healthy population (all ages), with a 420% change in frontal areas (FIG. 13C) and 480% change in parietal areas (FIG. 13B), relative to its age related control group of healthy subjects over 70. The change of P60 for healthy population to N60 for the demented population is illustrated in FIGS. 14A-14C.

The N100-P180 slope displays a significant change in demented population compared to all healthy groups, with a decrease of 60% to 95% in all areas, most pronounced in frontal (FIG. 13C) and parietal (FIG. 13B) areas ($p<0.0001$). Another significant difference is demonstrated between young and old (over 70) population, in the frontal and temporal areas ($p<0.01$). Taken together the slopes P60-N100 and N100-P180 provide a robust clustering tool for defining brain health and age dependent changes, where slopes ratio of evoked response is used for evaluating age dependent brain functional changes.

Reference is made to FIGS. 15A-15D, which demonstrate the Ratio between STP of charge transfer (STP-Q) and STP of the N100-P180 slope, measured over the four cortical regions (Temporal, parietal, frontal and occipital). FIGS. 15A-15D demonstrate representative short term plasticity of charge transfer as a function of short term plasticity of N100-P180 Slope; FIG. 15A demonstrates representative temporal hotspot; FIG. 15B demonstrates representative parietal hotspot; FIG. 15C demonstrates representative frontal hotspot; and FIG. 15D demonstrates representative occipital hotspot; full circle—left hotspot; empty circle—right hotspot; blue color for young healthy subjects (25-45 years old; N=40); green color for adult healthy subjects (50-70 years old; N=34); yellow-color for old healthy subjects (over 70, N=18); and red color for early Dementia subjects (over 70; N=20).

According to FIG. 15A-15D the STP-Q reveals significant reduction in left and right temporal areas (FIG. 15A) of demented population compared to healthy groups of all ages ($p<0.05$), while the other areas (FIGS. 15B-15D) reveal significant reduction in demented subject only compared to young and elderly population (50-70) ($p<0.01$), suggesting that STP-Q changes are age dependent in all brain areas, but increase in temporal areas during dementia. As demonstrated, the N100-P180 STP is reduced in demented population compared to all healthy groups, most significantly in frontal and temporal areas (FIGS. 15A and 15C) with a significant change from age related healthy controls ($p<0.001$), age dependent changes are less pronounced and non-significant. Therefore, according to some embodiments, STP measures are provided as indicators of frontal and temporal plasticity changes, related specifically to dementia.

According to some embodiments, the invention provides to a system and methods for evaluation of brain abnormalities, such as structural damage of grey or white matter. The system comprises EEG and Magnetic stimulation for the evaluation of evoked brain response provoked by TMS pulse. By measuring EEG response to single pulse TMS stimulation onto certain brain areas (one or more), a brain network signature response is acquired that can be compared to healthy normal brain response, for evaluation of brain structural damage of grey or white matter.

According to some embodiments, the TMS stimulation may be delivered to different brain circuits, at frequency of 0.1 to 100 Hz in varying intensities from 0.05 to 5 Tesla.

According to some embodiments, the EEG response evoked by TMS is measured at a time step selected between 0-400 milliseconds from TMS stimulation end.

According to some embodiments, the EEG response contains negative and positive peaks that are consistent between individuals with healthy brain structure.

According to some embodiments, the EEG response peaks to the TMS stimulation contain the peaks of P30, N45, P60, N100 and P180 and/or other consistent peaks.

According to some embodiments, the EEG response from normally structured brain has consistent signature in a peak timing amplitude and slopes, in the range of +/−standard deviation from average normal healthy population in each recording EEG electrode.

According to some embodiments, the EEG response from abnormally structured brain, caused either by abnormalities in the white matter or the grey matter of different brain area or intra-cranial pressure induced activity changes, is inconsistent with normal healthy brain signature and can vary in peak timing, amplitude or slope.

According to some embodiments, the EEG response from abnormal structured, in the grey or white matter or changes in intracranial pressure in different electrodes can display inconsistent response and can vary in peak timing, amplitude or slope.

Reference is made to FIGS. 16A-16B, which demonstrate the correlation between the mean N100-P180 slope and the mean P60-N100 slope. FIG. 16A demonstrates the stimulation of the left motor cortex and FIG. 16B demonstrates the stimulation of the right motor cortex, both in healthy 25-45 years old, healthy 50-70 years old, healthy over 70 years old, and CVA cases with a brain injury in either the left corticospinal track, left frontal lobe and left temporal lobe.

Figure 17B:
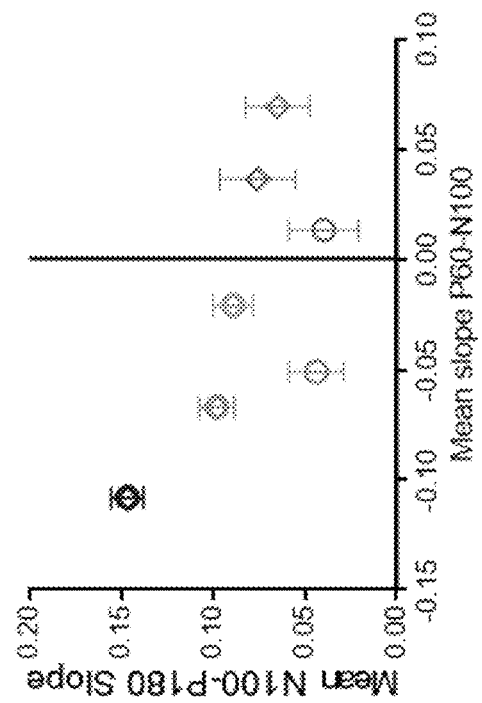
FIGS. 17A and 17B demonstrate connectivity differences between healthy intact brain and specific brain injuries in midbrain and brain stem, according to some embodiments of the invention.
Figure 17A:
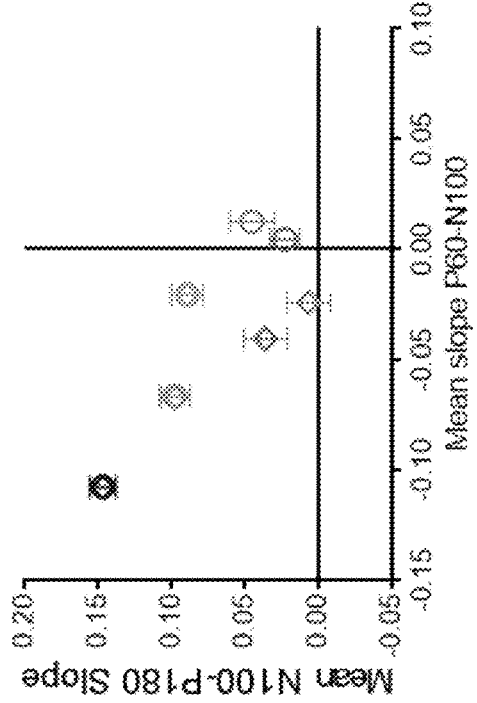

Reference is made to FIGS. 17A-17B, which demonstrate the correlation between the mean N100-P180 slope and the mean P60-N100 slope. FIG. 17A demonstrates the stimulation of the left motor cortex and FIG. 17B demonstrates the stimulation of the right motor cortex, both in healthy 25-45 years old, healthy 50-70 years old, healthy over 70 years old, and CVA cases with a brain injury in either the basal ganglia or the brain stem.

Reference is made to FIGS. 18A-18B, demonstrate the correlation between the mean N100-P180 slope and the mean P60-N100 slope. FIG. 18A demonstrates the stimulation of the left motor cortex and FIG. 18B demonstrates the stimulation of the right motor cortex, both in healthy 25-45 years old, healthy 50-70 years old, healthy over 70 years old, and CVA cases with a brain injury in either the left corticospinal track, left frontal lobe and left temporal lobe.

Figures 19A, 19B:
FIGS. 19A and 19B demonstrate short term plasticity differences between healthy intact brain and specific brain injuries at the left side, according to some embodiments of the invention.

Reference is made to FIGS. 19A-19B, which demonstrate the correlation between the area under the plasticity curve and N100-P180 slope of plasticity. FIG. 19A demonstrates the stimulation of the left motor cortex and FIG. 19B demonstrates the stimulation of the right motor cortex; both in healthy 25-45 years old, healthy 50-70 years old, healthy over 70 years old, and CVA cases with a brain injury in either the left corticospinal track, left frontal lobe and left temporal lobe.

Figure 20A:
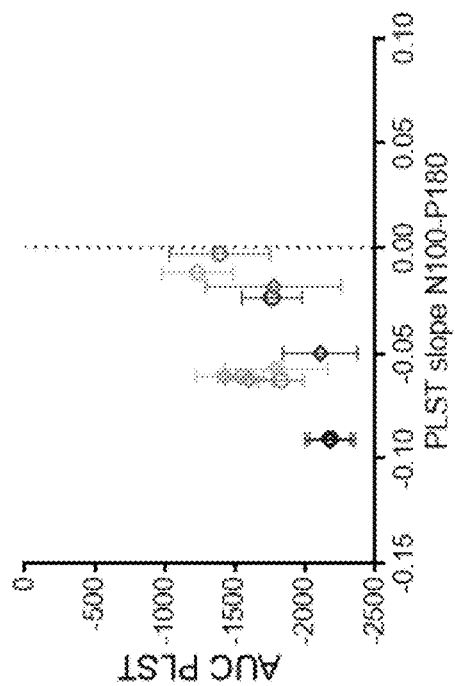
FIGS. 20A and 20B demonstrate short term plasticity differences between healthy intact brain and specific brain injuries in midbrain and brain stem, according to some embodiments of the invention.
Figure 20B:
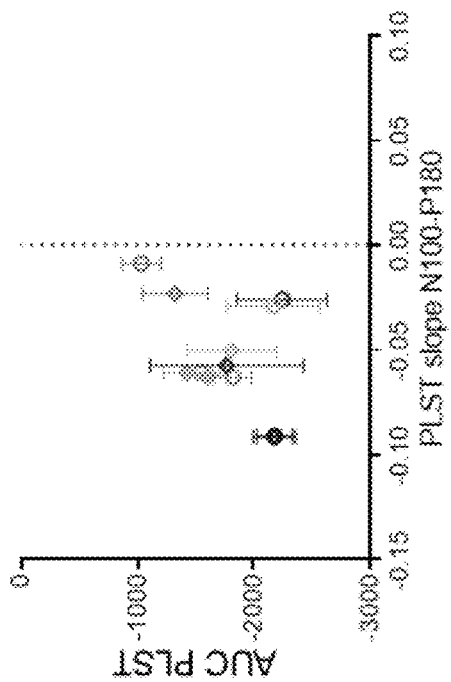

FIGS. 20A and 20B demonstrate short term plasticity differences between healthy intact brain and specific brain injuries in midbrain and brain stem, according to some embodiments of the invention;

FIGS. 21A and 21B demonstrate short term plasticity differences between healthy intact brain and specific brain injuries in right side, according to some embodiments of the invention.

STUDY SUBJECTS GROUP 2: Four groups were included in the following demonstrations. Groups are defined as follows:
   (a) young and health, 25-45 years old, (N=30; mean age: 35, standard deviation (STDV): 6.6);
   (b) healthy adults, 50-70 years old, (N=30 mean age: 61; STDV: 5.9);
   (c) healthy elderly, >70 years old; (N=17; mean age: 75.4; STDV: 6.6);
   (d) patients diagnosed with MCI/mild dementia, >65 years old, (N=20; mean age: 75.2, STDV: 4.3).

According to some embodiments, healthy subjects were determined per: a physician assessment, absence of significant abnormal findings in MRI scan, no central nerve system (CNS) directed prescribed medication treatment, and a neurocognitive evaluation by neuropsychologist, which includes a normal computerized cognitive evaluation (over 95 mean global score normalized to age related population).

According to some embodiments, MCI/mild dementia was defined as follows: neuropsychologist evaluation, Montreal Cognitive Assessment (MoCA) score between 11 and 22, Neurotrax BrainCare computerized testing memory index score at least 1.5 standard deviations (STDV) below age related norm and at least one more cognitive domain (out of 5 attention/memory/Information processing speed/motor function/Executive function) index score with minimum of 1.5 STDV below norm. All patients underwent a brain MRI scan 1-2 weeks before DELPHI evaluation. Imaging was performed with a 3 Tesla system (20 channels, MAGNETOM Skyra, Siemens Medical Solutions). The MRI protocol included T2 weighted, T1 weighted, FLAIR and susceptibility weighted imaging (SWI) sequences. All scans were analyzed at a central lab by a neuro-radiologist. Assessment of cognitive functions was performed by trained neuropsychologists using the MoCA test and NeuroTrax computerized BrainCare cognitive battery tests (NeuroTrax Corp., TX).

Experimental Results—Group 2

AGE DEPENDENT CHANGES IN BRAIN NETWORK FUNCTIONALITY: The purpose is to examine whether the electrophysiological parameters described above change during aging in humans and differentiate normal-healthy physiological process from pathological, degenerative deterioration of brain network functionality. It is known that cortical excitation-inhibition balance changes with normal aging and during neurodegenerative pathological deterioration. According to some embodiments, by examining the regional excitatory-inhibitory components of evoked response can provide a significant physiological measure for monitoring brain health through aging.

According to some embodiments, physiological patterns of network functionality that best distinguished between groups (aging and MCI/mild dementia) cab be automatically identified by the DELPHI algorithm analysis and are presented in the following.

According to some embodiments, evaluation of age dependent changes in network strength is provided. The DELPHI analysis of single pulse response is displayed as connectivity matrixes of averaged age groups, as demonstrated in FIGS. 22A-22D. The data in FIGS. 22A-22D presents averaged population response of:

(a) 25-45 years old (yo) healthy group;
(b) 50-70 years old healthy group;
(c) over 70 years old healthy group;
(d) over 70 years old diagnosed with Mild dementia.

Figure 22A:
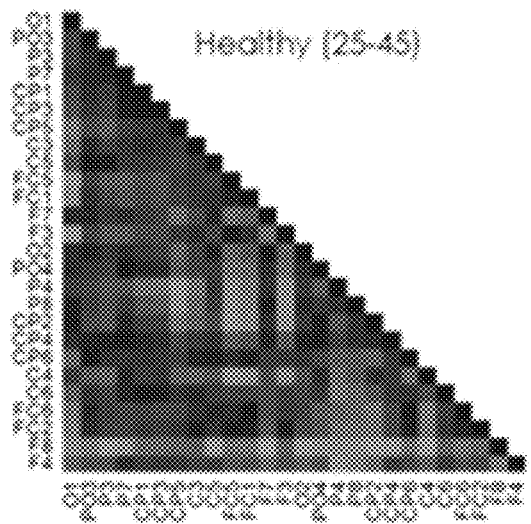
FIGS. 22A, 22B, 22C and 22D demonstrate evaluation of age dependent changes, and brain health changes in connectivity maps and network strength, according to some embodiments of the invention.
Figure 22B:
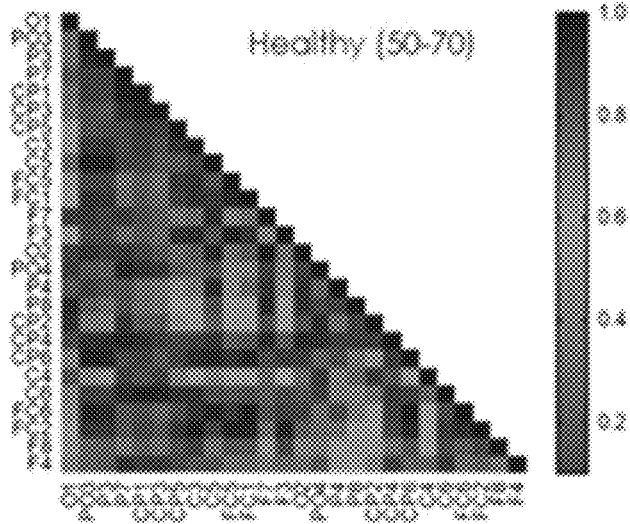
Figure 22C:
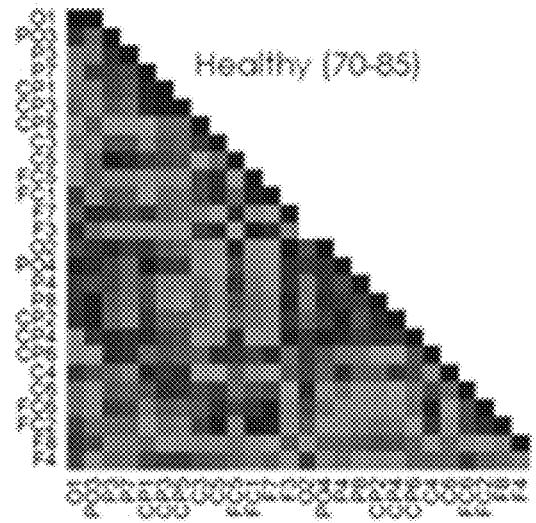
Figure 22D:
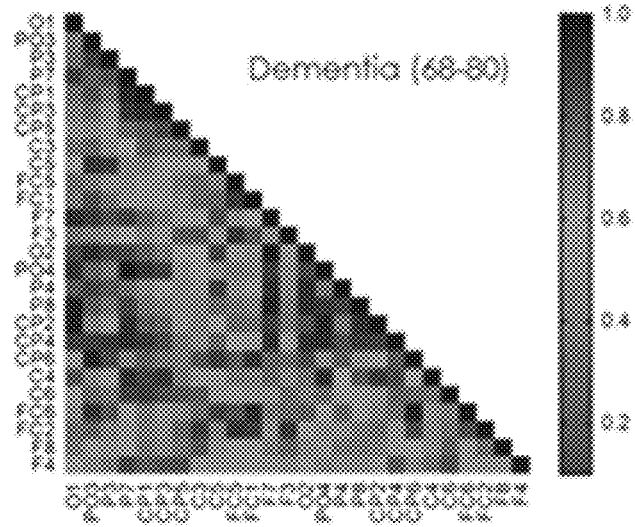

Correlation values are presented as consecutive color-coded bar, blue color demonstrates high correlation, while red color demonstrates low correlation. According to some embodiments, a decrease in signal coherence is observed with age. FIG. 22A demonstrate young 25-45 yo. matrix it displays high correlation values, which are slightly decreased in the 50-70 yo. group as demonstrated in FIG. 22B, and further decreases in the 70-85 yo. group as demonstrated in FIG. 22C. A significant difference is observed in the MCI/mild dementia patients demonstrated in FIG. 22D, which display a sparse connectivity map with pronounced decrease in interhemispheric and regional coherence between frontal and temporal and parietal areas.

According to some embodiments, and as demonstrated in FIGS. 23A-23F, DELPHI is configured to identify two features that display a significant age dependent decrease in both early (as in FIG. 23A for P60-N100) and late (as FIG. 23B for N100-P180) components of evoked response (data displayed for right hemisphere, contralateral to stimulation, parietal cortex).

Figure 23A:
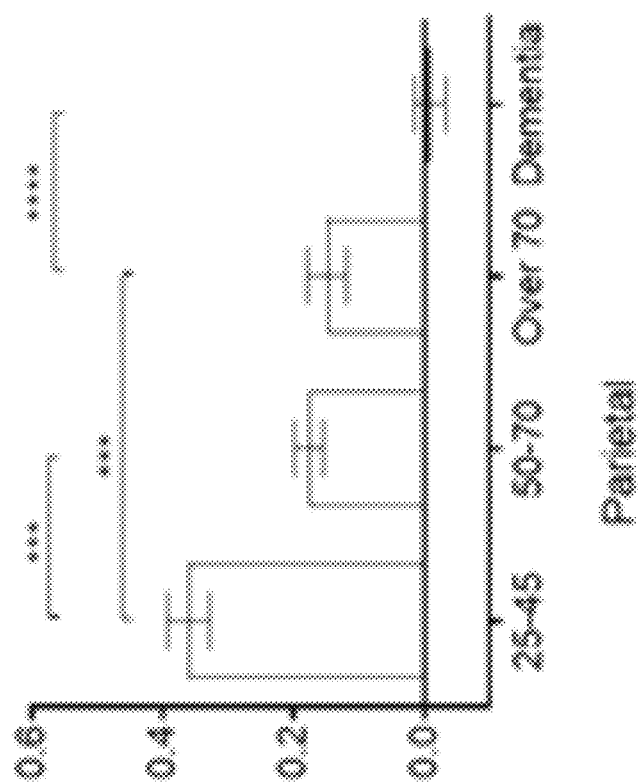
Figure 23B:
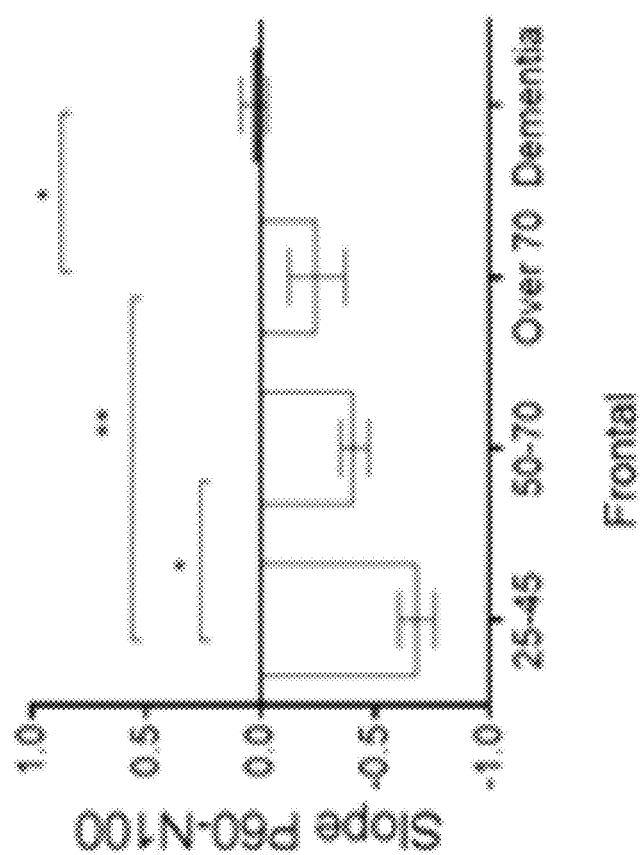

According to some embodiments, the comparison of the two age comparable groups of healthy elderly and patients diagnosed with MCI/mild dementia, demonstrates a significant difference in both components, particularly in the late slope of evoked response (N100-P180), as demonstrated in FIG. 23B.

According to some embodiments, the group averaged regional ratio, between these two slopes (early and late) of evoked response, displays a significant, age dependent, change with pronounced differentiation between normal healthy aging, and MCI/mild dementia, over the frontal, parietal, temporal and occipital cortical areas, as respectively demonstrated in FIGS. 23C-23F demonstrate color-coded images of subjects from the representative four study groups. FIG. 23C demonstrates a 38-year-old healthy subject with high and uniform ratio between the late and early slope of evoked response reflected as a homogeneous blue colored brain. FIG. 23D demonstrates a decline in the measured ratio is demonstrated with age, translated into light blue colored brain of a 58-year-old subject, representing the healthy 50-70 age group, and a green-yellow colored brain for a 75-year-old representing the healthy 70-85 years old group, as demonstrated in FIG. 23E. The MCI/mild dementia group, represented by a 71 years-old subject, displays a negative high ratio between late and early slopes of evoked response, reflected as orange colored cortical brain network functionality, as demonstrated in FIG. 23F.

Figure 24B:
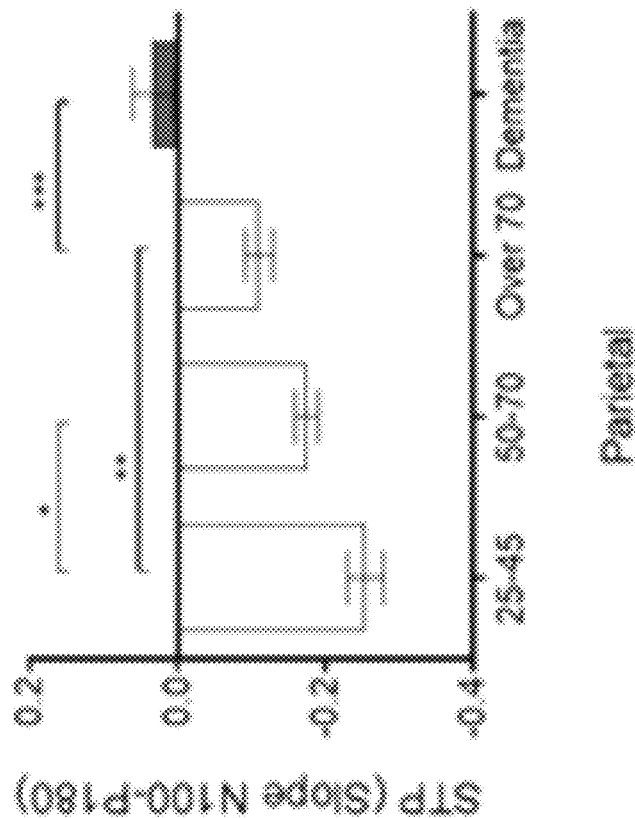
Figure 24A:
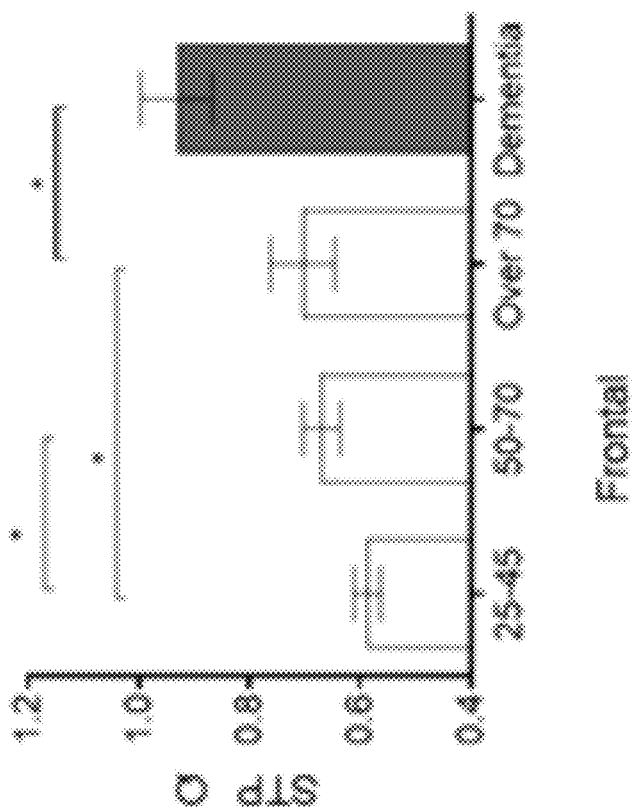
Figure 24C:
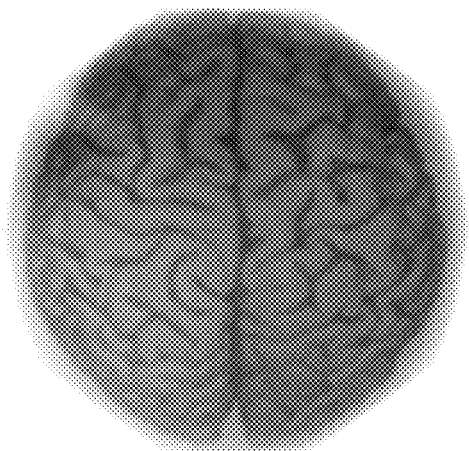
Figure 24D:

AGE DEPENDENT CHANGES IN NETWORK SHORT TERM PLASTICITY: the brain network plasticity is known to change with age. Moreover, progression of degenerative disorders as AD, correlate with decrease in brain network plasticity. According to some embodiments, DELPHI's analysis of the history dependency is configured to identify two physiological parameters of network functionality that best distinguishes between groups (healthy aging vs. MCI/mild dementia). According to some embodiments, the ratio between the total charge transfer of response (Q) evoked to an inhibitory protocol of stimulation (STP-Q), as demonstrated in FIG. 24A, and the ratio between the late slope component of evoked response to an inhibitory protocol of stimulation (STP-slope N100-P180), as demonstrated in FIG. 24B. According to some embodiments, a significant age dependent increases in the charge transfer STP and a decrease in the late slope STP, as demonstrated in FIGS. 24A and 24B (data from the right hemisphere (contralateral to stimulation) parietal cortex is displayed).

According to some embodiments, the comparison of the two age comparable groups of healthy elderly and patients with MCI/mild dementia, demonstrates a significant difference in both parameters. According to some embodiments, the most significant change in STP between the two groups is observed in the STP of the late slope, in which the MCI/mild dementia group displays positive values (FIG. 24B) reflecting a significant change in inhibitory response ($P<0.001$).

According to some embodiments, the ratio between these STP calculated parameters demonstrates lower age dependency. According to some embodiments, these extracted cortical plasticity ratio values can be displayed as individual pseudo-color-coded images. FIG. 24C-24F, demonstrate the significant differentiation between normal, healthy aging and early stages of dementia, implicating that while single pulse analysis of evoked response demonstrates strong correlation with normal aging (as demonstrated in FIGS. 23A-23F), plasticity measures seem to provide a robust parameter for separating normal from abnormal-pathological aging, as in the current case of early stages of dementia (as demonstrated in FIGS. 24A-24F).

Figure 25:
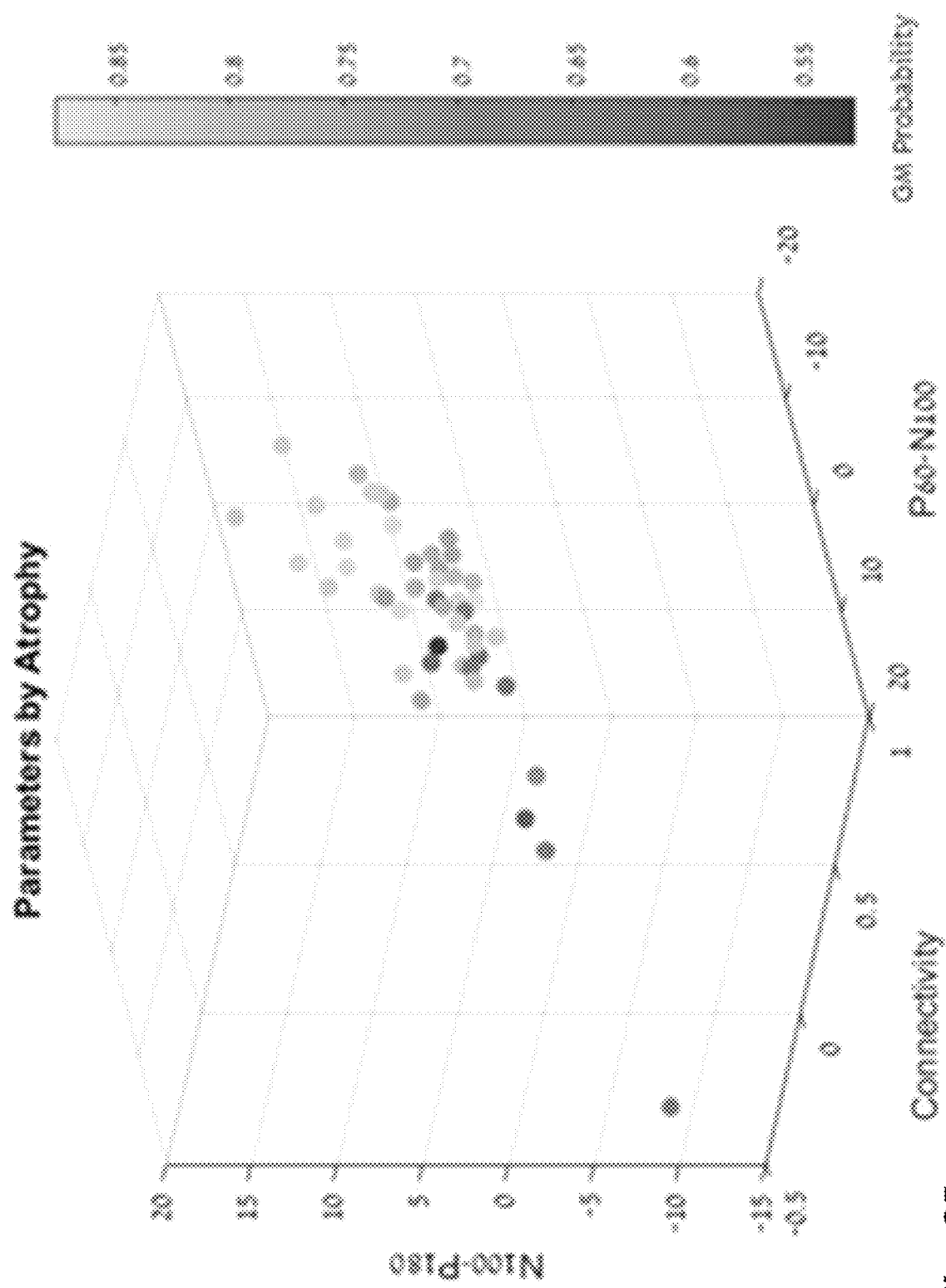
FIG. 25 demonstrate correlation between brain atrophy of grey matter as measured by MRI in healthy subjects with parameters of network short term plasticity and connectivity, according to some embodiments of the invention.
Figure 26:
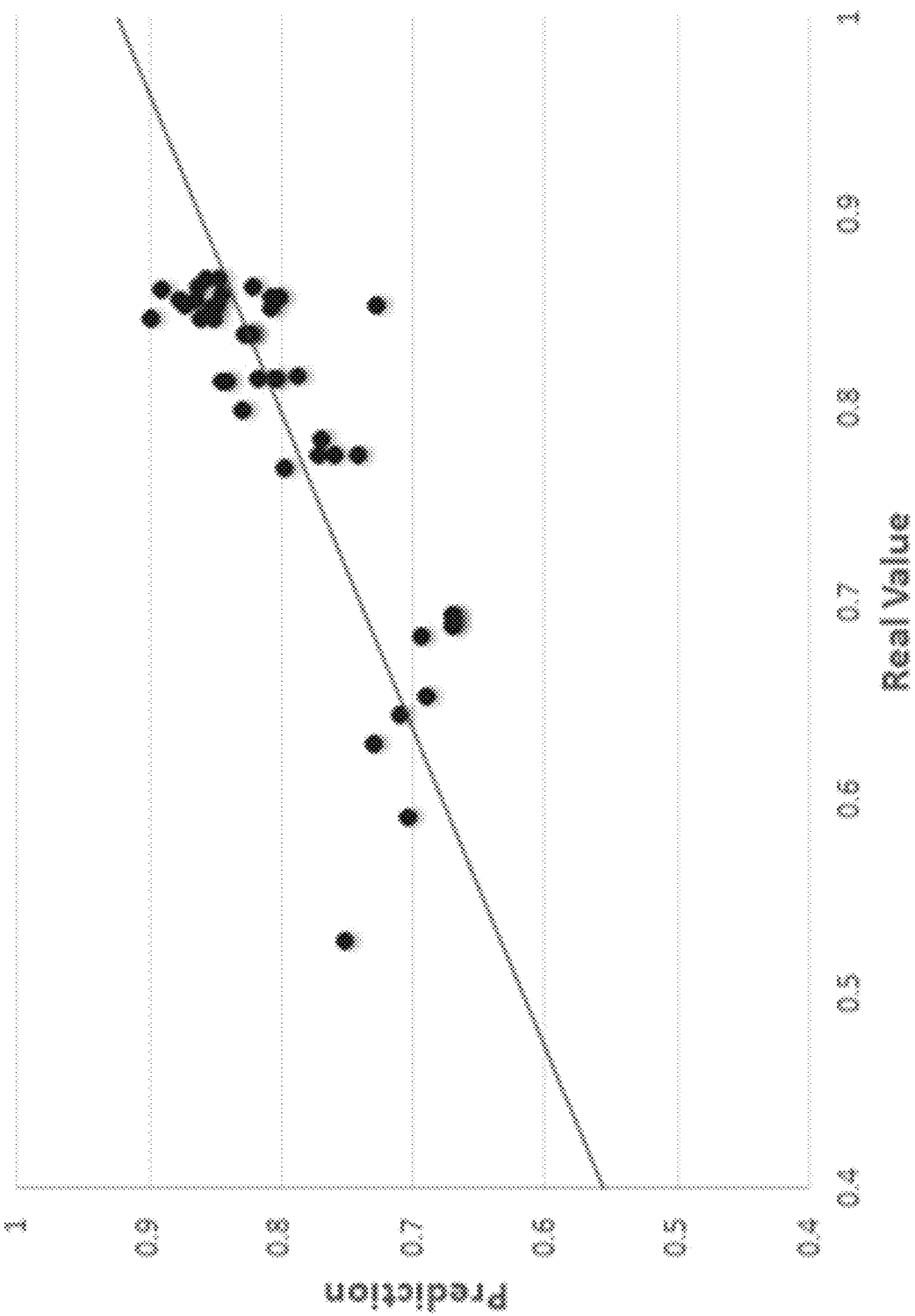
FIG. 26 demonstrate prediction model for brain atrophy of grey matter as measured by MRI in healthy subjects by parameters of network short term plasticity and connectivity, according to some embodiments of the invention.

FIG. 25 demonstrate correlation between brain atrophy of grey matter as measured by MRI in healthy subjects with parameters of network short term plasticity and connectivity, according to some embodiments of the invention; and FIG. 26 demonstrate prediction model for brain atrophy of grey matter as measured by MRI in healthy subjects by parameters of network short term plasticity and connectivity, according to some embodiments of the invention.

CONCLUSION

The human brain is a highly complexed network, comprised of physical and logical topology. Physical topology defines how nodes in a network are physically linked and includes aspects such as location and physical distance between nodes. Logical topology describes the network hierarchy and data flow, or how signals behave in the network (D. S. Bassett et al., *Efficient physical embedding of topologically complex information processing networks in brains and computer circuits*. PLoS Comput Biol 6, e1000748 (2010). V. M. Eguíluz, D. R. Chialvo, G. A. Cecchi, M Baliki, A. V. Apkarian, *Scale-free brain functional networks*. Phys Rev Lett 94, 018102 (2005)). In neuronal network context, physical topology refers to the location and morphology of different brain regions, while the logical topology refers to the nature of communication within and between the different brain regions. While every structural-physical change in brain topology is always manifested as functional-logical change, the opposite does not always stand. Thus, it is highly important to monitor brain network logical topology in order to evaluate brain status and "health" throughout life, in the developing brain, during aging, in the progression of neurodegenerative disorders and pathological deterioration.

Current study results display the ability of DELPHI using TMS-EEG technology for measuring crucial brain network parameters of connectivity and plasticity and its relevance for monitoring brain health. Network connectivity measures displayed in this study, indicate monitorable changes that occur with age and point to the ability of this technology to monitor subtle structural and functional changes, as well as the ability to differentiate normal and abnormal aging. Connectivity maps display changes in connectivity between healthy and mild dementia subjects mainly relating frontal areas, indicating a decrease in inter-hemispheric synchronicity, as well as decreased synchronicity between frontal and temporal or parietal areas (FIGS. 22A-22D).

These results are consistent with several structural and functional studies demonstrating intercortical disconnect such as changes in the corpus callosum (CC) in early stages of AD and MCI (Di Paola et al., 2010a; Di Paola et al., 2010b; Frederiksen et al., 2011). Changes in transcallosal connectivity have also been displayed using TMS in a study differentiating between demented and cognitively impaired non demented patients (Lanza et al., 2013). TEP slopes, which provide a description of TEP form and an excitation/inhibition reference (Rossi et al., 2009; Tremblay et al., 2019), display an age dependent decrease in both early and late slopes of response (FIGS. 23A-23B). This decrease may be associated with atrophy of gray and white matter or changes in excitation/inhibition balance as supported by anatomical MRI and EEG studies which indicate reduced fiber tracks in frontal and temporal areas and front-occipital reduced synchronicity (Dipasquale and Cercignani, 2016; Sexton et al., 2011; Teipel et al., 2016). In addition, TEP slopes display a clear separation of pathological mild dementia group from healthy control which includes a phase shift represented by slope changes, these may be accounted by severe brain atrophy and/or excitation/inhibition balance shift. Short term plasticity measures (FIGS. 24A-24B), which evaluates the changes in excitation/inhibition balance, are shown to provide discrete parameter which display a sort of binary step function for differentiating the healthy and diseased brain. These results may indicate as to the nature of significant changes in pathological population that results from shifting in excitation/inhibition mechanisms as opposed to connectivity and structural changes that may account for age related changes displayed here. This study results support the significance and value of TMS in understanding and monitoring brain health and pathological aging including neurodegenerative disorders such as Alzheimer's disease (AD) and vascular dementia. Studies of connectivity, excitability and plasticity utilizing TMS have provided evidence suggesting cortical excitability changes in the early stages of the disease, as well as altered cortical inhibition and cholinergic mechanisms (Bella et al., 2016; Bella et al., 2013; Ferreri et al., 2017; Lanza et al., 2017; Ni and Chen, 2015). It has also been shown that TMS-EEG evoked potentials (TEP) poses major advantages as: (a) high reproducibility of evoked response within individuals over occipital, parietal, premotor, motor and prefrontal regions (Casarotto et al., 2010; Kerwin et al., 2018; Lioumis et al., 2009). (b) ability to measure TEP at sub MT intensities. Stimulating the M1 at intensities as low as 40% of the MEP threshold, exemplifying the sensitivity of the measure (Komssi and Kähkönen, 2006; Komssi et al., 2004). (c) Recorded both locally, and in distal electrodes, allowing for the study of the spreading of activation over cortical areas (Ilmoniemi et al., 1997; Komssi et al., 2002).

As demonstrated above, using DELPhi allows to characterize functional properties of normal-healthy brains in a reproducible way. Moreover being reliable, DELPhi shows high sensitivity to changes in brain functionality, related with age or pathology. These finding have a major significant clinical importance as the new tool presented here provides clinicians not only with the ability to determine whether an individual brain is healthy to his age group, in the evaluated physiological parameters, but also with the potential ability to detect pathological-degenerative process at a very early stage, with regards to any current available clinical tool. In addition, DELPhi has a huge potential as a monitoring tool, evaluating brain directed drug effects on the individual brain network functionality. This understanding is highly relevant to the psychiatric clinical practice, determining the optimal course of pharmacological treatment for a patient, as well as for monitoring the efficacy of rehabilitation process post stroke or traumatic brain injuries.

To make the DELPhi technology accessible to clinicians, the numeric data matrix collected during the evaluation procedure can be presented as a color coded map brain image displaying absolute and relative to healthy quantitative measures of network's connectivity and plasticity. This new expression of brain functional status completes current existing technologies as MRI and CT scan, which provide only limited understanding focused on anatomical or prefusion changes but do not provided the fundamentally needed direct understanding of brain functionality.

The clinical work presented herein describe the physiological characterization of brain functionality by stimulating a single cortical location (left M1). It is important to note that simulation in multiple sites will most probably enable better mapping of brain functionality moreover in pathological conditions and brain insults as traumatic brain injuries and stroke, allowing early evaluation of the severity of damage and assessment of rehabilitation potential.

The extent of functional changes during brain aging varies among individuals in a way that cannot be quantified using current available clinical tools. Early identification of abnormal brain aging is extensively researched, scanning genetic, biochemical, and neuropsychological aspects of the transition from normal to pathologic aging. The development of drug therapies or behavioral modifications to slow or possibly halt the complex processes involved in abnormal aging requires the earliest possible intervention. Hence researchers are searching for biochemical or imaging markers that might be used to predict the clinical course of early phases of dementia versus normal aging patterns or to monitor treatment progress.

The provided results demonstrate that evaluating electrophysiological properties, as network connectivity, strength and plasticity, enable the characterization of age dependent brain functional changes and the monitoring of abnormal aging processes. It also presents the ability of the system in tracking changes in brain structure of grey matter and white matter that are known to affect connectivity and plasticity. As desaturated, single pulse connectivity parameters demonstrate an age dependent behavior that is significantly changed during abnormal aging, brain atrophy and structure, these parameters are supported by network short term plasticity data, shown to be significantly different in pathological aging. The data presented herein supports the understanding that direct electrophysiological imaging is clinically efficient in evaluating brain functionality and provides a clinical tool for monitoring brain network function and brain health. The current demonstrations show that the DELPHI automated acquisition and analysis system can be used in order to monitor brain health throughout aging and may enable early detection of abnormal physiological changes leading to neurodegeneration, and evaluate brain structural changes.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. Apparatus comprising:
   at least one coil;
   a plurality of electrodes configured to be placed in contact with a subject's head; and
   at least one computer processor configured to:
      drive the at least one coil to apply a magnetic stimulation to the subject's brain;
      receive a magnetic-stimulation-evoked-potential signal from the plurality of electrodes;
      process the magnetic-stimulation-evoked-potential signal so as to identify, in the magnetic-stimulation-evoked-potential signal, a negative peak at about 100 ms after the stimulation and a positive peak at about 180 ms after the stimulation;
      measure a slope between the negative peak and the positive peak;
      drive the at least one coil to apply an inhibitory protocol of magnetic stimulation to the subject's brain;
      receive an inhibitory-magnetic-stimulation-evoked-potential signal from the plurality of electrodes;
      compute a slope of a late portion of the inhibitory-magnetic-stimulation-evoked-potential signal;
      at least partially in response to the slope between the negative peak and the positive peak and to the slope of the late portion of the inhibitory-magnetic-stimulation-evoked-potential signal, evaluate whether the subject is at risk of dementia; and
      generate an output in response to evaluating whether the subject is at risk of dementia.

2. The apparatus according to claim 1,
   wherein the at least one computer processor is further configured to determine a slope of an early portion of the magnetic-stimulation-evoked-potential signal; and
   wherein the at least one computer processor is configured to evaluate that the subject is at risk of dementia at least partially in response to detecting that a ratio between the slope of the early portion of the magnetic-stimulation-evoked-potential signal and the slope between the negative peak and the positive peak is below a given threshold.

3. The apparatus according to claim 2, wherein the signal further includes another positive peak at about 60 ms after the stimulation, and wherein the at least one computer processor is configured to measure the slope of the early portion of the magnetic-stimulation-evoked-potential signal by measuring a slope between the other positive peak and the negative peak.

4. The apparatus according to claim 1,
   wherein the at least one computer processor is further configured to
      measure a total charge transfer of the inhibitory-magnetic-stimulation-evoked-potential signal; and
   wherein the at least one computer processor is configured to evaluate whether the subject is at risk of dementia at least partially in response to the total charge transfer.

5. The apparatus according to claim 4,
   wherein the at least one computer processor is configured to evaluate that the subject is at risk of dementia in response to detecting that a ratio between the total charge transfer and the slope of the late portion of the inhibitory-magnetic-stimulation-evoked-potential signal is above a given threshold.

6. The apparatus according to claim 4, wherein the at least one computer processor is configured to evaluate that the subject is at risk of dementia in response to the total charge transfer being above a given threshold.

7. The apparatus according to claim 1, wherein the at least one computer processor is configured to measure the slope of the late portion of the inhibitory-magnetic-stimulation-evoked-potential signal by measuring the slope between another negative peak at about 100 ms after the application of the inhibitory protocol of magnetic stimulation and another positive peak at about 180 ms after the application of the inhibitory protocol of magnetic stimulation.

8. The apparatus according to claim 1, wherein the at least one computer processor is configured to evaluate that the subject is at risk of dementia in response to the slope between the negative peak and the positive peak being below a given threshold.

9. A method comprising:
using at least one computer processor:
  driving a coil to apply a magnetic stimulation to a subject's brain;
  receiving a magnetic-stimulation-evoked-potential signal from electrodes that are placed in contact with the subject's head;
  processing the magnetic-stimulation-evoked-potential signal so as to identify, in the magnetic-stimulation-evoked-potential signal, a negative peak at about 100 ms after the stimulation and a positive peak at about 180 ms after the stimulation;
  measuring a slope between the negative peak and the positive peak;
  driving the coil to apply an inhibitory protocol of magnetic stimulation to the subject's brain;
  receiving an inhibitory-magnetic-stimulation-evoked-potential signal from the electrodes;
  computing a slope of a late portion of the inhibitory-magnetic-stimulation-evoked-potential signal;
  at least partially in response to the slope between the negative peak and the positive peak and to the slope of the late portion of the inhibitory-magnetic-stimulation-evoked-potential signal, evaluating whether the subject is at risk of dementia; and
  generating an output in response to evaluating whether the subject is at risk of dementia.

10. The method according to claim 9, further comprising determining a slope of an early portion of the magnetic-stimulation-evoked-potential signal,
  wherein evaluating whether the subject is at risk of dementia comprises evaluating that the subject is at risk of dementia at least partially in response to detecting that a ratio between the slope of the early portion of the magnetic-stimulation-evoked-potential signal and the slope between the negative peak and the positive peak is below a given threshold.

11. The method according to claim 10, wherein the signal further includes another positive peak at about 60 ms after the stimulation, and wherein measuring the slope of the early portion of the magnetic-stimulation-evoked-potential signal comprises measuring a slope between the other positive peak and the negative peak.

12. The method according to claim 9, further comprising measuring a total charge transfer of the inhibitory-magnetic-stimulation-evoked-potential signal,
  wherein evaluating whether the subject is at risk of dementia comprises evaluating whether the subject is at risk of dementia in response to the total charge transfer.

13. The method according to claim 12,
  wherein evaluating whether the subject is at risk of dementia comprises evaluating that the subject is at risk of dementia in response to detecting that a ratio between the total charge transfer and the slope of the late portion of the inhibitory-magnetic-stimulation-evoked-potential signal is above a given threshold.

14. The method according to claim 12, wherein evaluating whether the subject is at risk of dementia comprises evaluating that the subject is at risk of dementia in response to the total charge transfer being above a given threshold.

15. The method according to claim 9, wherein measuring the slope of the late portion of the inhibitory-magnetic-stimulation-evoked-potential signal comprises measuring the slope between another negative peak at about 100 ms after the application of the inhibitory protocol of magnetic stimulation and another positive peak at about 180 ms after the application of the inhibitory protocol of magnetic stimulation.

16. The method according to claim 9, wherein evaluating whether the subject is at risk of dementia comprises evaluating that the subject is at risk of dementia in response to the slope between the negative peak and the positive peak being below a given threshold.

* * * * *